(12) United States Patent
Sheth et al.

(10) Patent No.: US 11,464,245 B2
(45) Date of Patent: Oct. 11, 2022

(54) FERMENTED BEVERAGES AND METHODS OF PRODUCTION THEREOF

(71) Applicant: Imvela Corp., Brooklyn, NY (US)

(72) Inventors: Ravi Sheth, Brooklyn, NY (US); Kendall Dabaghi, Brooklyn, NY (US); Felix Ekness, Brooklyn, NY (US); Miriam Shiffman, Pittsburgh, PA (US)

(73) Assignee: Imvela Corp., Brooklyn, NY (US)

( * ) Notice: Subject to any disclaimer, the term of this patent is extended or adjusted under 35 U.S.C. 154(b) by 0 days.

(21) Appl. No.: 17/687,563

(22) Filed: Mar. 4, 2022

(65) Prior Publication Data

US 2022/0183326 A1 Jun. 16, 2022

Related U.S. Application Data

(63) Continuation of application No. 17/515,358, filed on Oct. 29, 2021, now Pat. No. 11,311,033.

(60) Provisional application No. 63/108,189, filed on Oct. 30, 2020.

(51) Int. Cl.
   *A23L 33/135* (2016.01)
   *A23L 2/38* (2021.01)

(52) U.S. Cl.
   CPC ............. *A23L 2/382* (2013.01); *A23L 33/135* (2016.08); *A23V 2002/00* (2013.01)

(58) Field of Classification Search
   CPC .... A23L 2/382; A23L 33/135; A23V 2002/00
   USPC .......................................................... 426/61
   See application file for complete search history.

(56) References Cited

FOREIGN PATENT DOCUMENTS

| | | |
|---|---|---|
| CA | 2833764 A1 | 10/2012 |
| CN | 102100250 A | 6/2011 |
| CN | 104116110 A | 10/2014 |
| CN | 106174258 A | 12/2016 |
| CN | 106418061 A | 2/2017 |
| CN | 109007148 A | 12/2018 |
| DE | 19920236 A1 | 11/2000 |
| DE | 19921561 A1 | 11/2000 |
| DE | 102004045500 A1 | 3/2006 |
| DE | 202009010718 U1 | 12/2009 |
| DE | 202019005003 U1 | 5/2020 |
| EP | 0223705 A1 | 5/1987 |
| EP | 2412251 B1 | 2/2012 |
| ES | 2309587 T3 | 12/2008 |
| JP | 2008-245587 A | 10/2008 |
| KR | 20200038199 A | 4/2020 |
| RU | 2081911 C1 | 6/1997 |
| WO | WO 1995/022911 A1 | 8/1995 |
| WO | WO 2010/125193 A1 | 11/2010 |
| WO | WO 2016/187021 A1 | 11/2016 |
| WO | WO 2020/010421 A1 | 1/2020 |

OTHER PUBLICATIONS

International Search Report and Written Opinion dated Feb. 8, 2022 for Application No. PCT/US2021/057456.
[No Author Listed], Fresh Kombucha with Original Flavor. Accessed at Database GNPD [Online] Mintel, www.gnpd.com, Accession No. 1563396. Jun. 2, 2011. 4 pages.
Belloso-Morales et al.. Manufacture of a beverage from cheese whey using a "tea fungus" fermentation. Rev Latinoam Microbiol. Jan.-Jun. 2003;45(1-2):5-11.
Deppenmeier et al., Biochemistry and biotechnological applications of Gluconobacter strains. Appl Microbiol Biotechnol 60, 233-242 (2002).

*Primary Examiner* — Hamid R Badr

(74) *Attorney, Agent, or Firm* — Wolf, Greenfield & Sacks, P.C.

(57) ABSTRACT

Provided herein are fermented beverages comprising symbiotic microbial communities, and methods of production thereof.

30 Claims, 9 Drawing Sheets

Specification includes a Sequence Listing.

Sugar (time of bottling)

Sugar (14d after bottling)

Sugar (14d after bottling)

SEQUENCE LISTING

```
<160> NUMBER OF SEQ ID NOS: 24

<210> SEQ ID NO 1
<211> LENGTH: 132
<212> TYPE: DNA
<213> ORGANISM: Artificial Sequence
<220> FEATURE:
<223> OTHER INFORMATION: Synthetic

<400> SEQUENCE: 1
tacgaagggg gctagcgttg ctcggaatga ctgggcgtaa agggcgtgta ggcggtttgt     60
acagtcagat gtgaaatccc cgggcttaac ctgggagctg catttgatac gtgcagacta    120
gagtgtgaga ga                                                        132

<210> SEQ ID NO 2
<211> LENGTH: 132
<212> TYPE: DNA
<213> ORGANISM: Artificial Sequence
<220> FEATURE:
<223> OTHER INFORMATION: Synthetic

<400> SEQUENCE: 2
tacgaagggg gctagcgttg ctcggaatga ctgggcgtaa agggcgcgta ggcggttgtt     60
acagtcagat gtgaaatccc cgggcttaac ctgggaactg catttgatac gtgacgacta    120
gagttcgaga ga                                                        132

<210> SEQ ID NO 3
<211> LENGTH: 132
```

```
<212> TYPE: DNA
<213> ORGANISM: Artificial Sequence
<220> FEATURE:
<223> OTHER INFORMATION: Synthetic

<400> SEQUENCE: 3
tacgaagggg gctagcgttg ctcggaatga ctgggcgtaa agggcgcgta ggcggttgat    60
gcagtcagat gtgaaatccc cgggcttaac ctgggaactg catttgagac gcattgacta   120
gagttcgaga ga                                                       132

<210> SEQ ID NO 4
<211> LENGTH: 132
<212> TYPE: DNA
<213> ORGANISM: Artificial Sequence
<220> FEATURE:
<223> OTHER INFORMATION: Synthetic

<400> SEQUENCE: 4
tacgtaggtg gcaagcgttg tccggattta ttgggcgtaa agcgagcgca ggcggttttt    60
taagtctgat gtgaaagcct tcggcttaac cggagaagtg catcggaaac tgggagactt   120
gagtgcagaa ga                                                       132

<210> SEQ ID NO 5
<211> LENGTH: 132
<212> TYPE: DNA
<213> ORGANISM: Artificial Sequence
<220> FEATURE:
<223> OTHER INFORMATION: Synthetic

<400> SEQUENCE: 5
tacgtatgtc ccgagcgtta tccggattta ttgggcgtaa agcgagcgca gacggtttat    60
taagtctgat gtgaaagccc ggagctcaac tccggaatgg cattggaaac tggttaactt   120
gagtgcagta ga                                                       132

<210> SEQ ID NO 6
<211> LENGTH: 132
<212> TYPE: DNA
<213> ORGANISM: Artificial Sequence
<220> FEATURE:
<223> OTHER INFORMATION: Synthetic

<400> SEQUENCE: 6
tacgtaggtg gcaagcgttg tccggattta ttgggcgtaa agcgagcgca ggcggttttt    60
taggtctgat gtgaaagcct tcggcttaac cggagaagtg catcggaaac cgggagactt   120
gagtgcagaa ga                                                       132

<210> SEQ ID NO 7
<211> LENGTH: 132
<212> TYPE: DNA
<213> ORGANISM: Artificial Sequence
<220> FEATURE:
<223> OTHER INFORMATION: Synthetic

<400> SEQUENCE: 7
tacgtaggtg gcaagcgttg tccggattta ttgggcgtaa agcgagcgca ggcggttttt    60
taagtctgat gtgaaagcct tcggctcaac cgaagaagtg catcggaaac tgggaaactt   120
gagtgcagaa ga                                                       132

<210> SEQ ID NO 8
```

```
<211> LENGTH: 132
<212> TYPE: DNA
<213> ORGANISM: Artificial Sequence
<220> FEATURE:
<223> OTHER INFORMATION: Synthetic

<400> SEQUENCE: 8
tacgtaggtg gcaagcgtta tccggaatta ttgggcgtaa agcgcgcgca ggcggtttct    60
taagtctgat gtgaaagccc acggctcaac cgtggagggt cattggaaac tgggaacttt    120
gagtgcagaa ga                                                       132

<210> SEQ ID NO 9
<211> LENGTH: 132
<212> TYPE: DNA
<213> ORGANISM: Artificial Sequence
<220> FEATURE:
<223> OTHER INFORMATION: Synthetic

<400> SEQUENCE: 9
tacggagggt gcaagcgtta atcggaatta ctgggcgtaa agcgcacgca ggcggttgat    60
taagtcagat gtgaaatccc cgagcttaac ttgggaactg catttgaaac tggtcagcta    120
gagtcttgta ga                                                       132

<210> SEQ ID NO 10
<211> LENGTH: 132
<212> TYPE: DNA
<213> ORGANISM: Artificial Sequence
<220> FEATURE:
<223> OTHER INFORMATION: Synthetic

<400> SEQUENCE: 10
tacgtaggtc ccgagcgttg tccggattta ttgggcgtaa agcgagcgca ggtggtttat    60
taagtctggt gtaaaaggca gtggctcaac cattgtatgc attggaaact ggtagacttg    120
agtgcaggag ag                                                       132

<210> SEQ ID NO 11
<211> LENGTH: 132
<212> TYPE: DNA
<213> ORGANISM: Artificial Sequence
<220> FEATURE:
<223> OTHER INFORMATION: Synthetic

<400> SEQUENCE: 11
tacgtaggtg gcaagcgtta tccggattta ttgggcgtaa agcgagcgca ggcggttttt    60
taagtctgat gtgaaagccc tcggcttaac cgaggaagcg catcggaaac tgggaaactt   120
gagtgcagaa ga                                                       132

<210> SEQ ID NO 12
<211> LENGTH: 132
<212> TYPE: DNA
<213> ORGANISM: Artificial Sequence
<220> FEATURE:
<223> OTHER INFORMATION: Synthetic

<400> SEQUENCE: 12
tacgtaggtg gcaagcgtta tccggattta ttgggcgtaa agcgagcgca ggcggtcttt    60
taagtctaat gtgaaagcct tcggctcaac cgaagaagtg cattggaaac tgggagactt   120
gagtgcagaa ga                                                       132
```

```
<210> SEQ ID NO 13
<211> LENGTH: 132
<212> TYPE: DNA
<213> ORGANISM: Artificial Sequence
<220> FEATURE:
<223> OTHER INFORMATION: Synthetic

<400> SEQUENCE: 13
tacgaagggg gctagcgttg ctcggaatga ctgggcgtaa agggcgcgta ggcggtatgg      60
acagtcagat gtgaaattcc tgggcttaac ctgggggctg catttgatac gtccaaacta     120
gagtgtgaga ga                                                         132

<210> SEQ ID NO 14
<211> LENGTH: 132
<212> TYPE: DNA
<213> ORGANISM: Artificial Sequence
<220> FEATURE:
<223> OTHER INFORMATION: Synthetic

<400> SEQUENCE: 14
tacgtaggtg gcaagcgttg tccggattta ttgggcgtaa agcgagcgca ggcggtttct      60
taagtctgat gtgaaagcct tcggcttaac cggagaagtg catcggaaac tgggtaactt     120
gagtgcagaa ga                                                         132

<210> SEQ ID NO 15
<211> LENGTH: 132
<212> TYPE: DNA
<213> ORGANISM: Artificial Sequence
<220> FEATURE:
<223> OTHER INFORMATION: Synthetic

<400> SEQUENCE: 15
tacgtaggtg gcaagcgttg tccggattta ttgggcgtaa agcgagcgca ggcggtttct      60
taggtctgat gtgaaagcct tcggcttaac cggagaagtg catcggaaac caggagactt     120
gagtgcagaa ga                                                         132

<210> SEQ ID NO 16
<211> LENGTH: 132
<212> TYPE: DNA
<213> ORGANISM: Artificial Sequence
<220> FEATURE:
<223> OTHER INFORMATION: Synthetic

<400> SEQUENCE: 16
tacgtatgtc ccgagcgtta tccggattta ttgggcgtaa agcgagcgca gacggttgat      60
taagtctgat gtgaaagccc ggagctcaac tccggaatgg cattggaaac tggttaactt     120
gagtgttgta ga                                                         132

<210> SEQ ID NO 17
<211> LENGTH: 132
<212> TYPE: DNA
<213> ORGANISM: Artificial Sequence
<220> FEATURE:
<223> OTHER INFORMATION: Synthetic

<400> SEQUENCE: 17
tacgtaggtg gcaagcgttg tccggattta ttgggcgtaa agggaacgca ggcggtctttt     60 taagtctgat gtgaaagcct tcggcttaac cgaagtcgtg cattggaaac tgggagactt     120
gagtgcagaa ga                                                         132
```

<210> SEQ ID NO 18
<211> LENGTH: 132
<212> TYPE: DNA
<213> ORGANISM: Artificial Sequence
<220> FEATURE:
<223> OTHER INFORMATION: Synthetic

<400> SEQUENCE: 18

```
tacgaagggg gctagcgttg ctcggaatga ctgggcgtaa agggcgtgta ggcggttttg      60
acagtcagat gtgaaatccc cgggcttaac ctgggagctg catttgagac gttaagacta     120
gagtgtgaga ga                                                         132
```

<210> SEQ ID NO 19
<211> LENGTH: 132
<212> TYPE: DNA
<213> ORGANISM: Artificial Sequence
<220> FEATURE:
<223> OTHER INFORMATION: Synthetic

<400> SEQUENCE: 19

```
tacgaagggg gctagcgttg ctcggaatga ctgggcgtaa agggcgcgta ggcggtttgg      60
acagtcagat gtgaaattcc tgggcttaac ctgggggctg catttgatac gtccagacta     120
gagtgtgaga ga                                                         132
```

<210> SEQ ID NO 20
<211> LENGTH: 1548
<212> TYPE: DNA
<213> ORGANISM: Artificial Sequence
<220> FEATURE:
<223> OTHER INFORMATION: Synthetic

<400> SEQUENCE: 20

```
attgagagtt tgatcctggc tcaggatgaa cgctggcggc gtgcctaata catgcaagtc      60
gaacgcacag cgaaaggtgc ttgcacctttt caagtgagtg gcgaacgggt gagtaacacg    120
tggacaacct gcctcaaggc tggggataac atttggaaac agatgctaat accgaataaa    180
acttagtgtc gcatgacaca agttaaaaag gcgcttcggc gtcacctaga gatggatccg    240
cggtgcatta gttagttggt ggggtaaagg cctaccaaga caatgatgca tagccgagtt    300
gagagactga tcggccacat tgggactgag acacggccca aactcctacg ggaggctgca    360
gtagggaatc ttccacaatg gcgaaagcc tgatggagca acgccgcgtg tgtgatgaag    420
gctttcgggt cgtaaagcac tgttgtatgg gaagaacagc tagaatagga atgattttta    480
gtttgacggt accataccag aaagggacgg ctaaatacgt gccagcagcc gcggtaatac    540
gtatgtcccg agcgttatcc ggatttattg ggcgtaaagc gagcgcagac ggtttattaa    600
gtctgatgtg aaagcccgga gctcaactcc ggaatggcat tggaaactgg ttaacttgag    660
tgcagtagag gtaagtggaa ctccatgtgt agcggtggaa tgcgtagata tatggaagaa    720
caccagtggc gaaggcggct tactggactg caactgacgt tgaggctcga aagtgtgggt    780
agcaaacagg attagatacc ctggtagtcc acaccgtaaa cgatgaacac taggtgttag    840
gaggtttccg cctcttagtg ccgaagctaa cgcattaagt gttccgcctg ggagtacga    900 ccgcaaggtt gaaactcaaa ggaattgacg ggacccgca caagcggtgg agcatgtggt    960
ttaattcgaa gcaacgcgaa gaaccttacc aggtcttgac atcctttgaa gcttttagag   1020
atagaagtgt tctcttcgga gacaaagtga caggtggtgc atggtcgtcg tcagctcgtg   1080
tcgtgagatg ttgggttaag tcccgcaacg agcgcaaccc ttattgttag ttgccagcat   1140
```

```
tcagatgggc actctagcga gactgccggt gacaaaccgg aggaaggcgg ggacgacgtc    1200
agatcatcat gccccttatg acctgggcta cacacgtgct acaatggcgt atacaacgag    1260
ttgccagccc gcgagggtga gctaatctct taaagtacgt ctcagttcgg attgtagtct    1320
gcaactcgac tacatgaagt cggaatcgct agtaatcgcg gatcagcacg ccgcggtgaa    1380
tacgttcccg ggtcttgtac acaccgcccg tcacaccatg ggagtttgta atgcccaaag    1440
ccggtggcct aaccttttag gaaggagccg tctaaggcag acagatgac tggggtgaag    1500 tcgtaacaag gtagccgtag gagaacctgc ggctggatca cctcctttt               1548
```

<210> SEQ ID NO 21
<211> LENGTH: 1480
<212> TYPE: DNA
<213> ORGANISM: Artificial Sequence
<220> FEATURE:
<223> OTHER INFORMATION: Synthetic

<400> SEQUENCE: 21

```
ctgagagttt gatcctggct cagagcgaac gctggcggca tgcttaacac atgcaagtcg    60
cacgaaggtt tcggccttag tggcggacgg gtgagtaacg cgtagggatc tatccacggg    120 tggggacaa cttcgggaaa ctggagctaa taccgcatga tacctgaggg tcaaaggcgc    180
aagtcgcctg tggaggaacc tgcgttcgat tagctagttg gtggggtaaa ggcctaccaa    240
ggcgatgatc gatagctggt ttgagaggat gatcagccac actgggactg agacacggcc    300
cagactccta cgggaggcag cagtggggaa tattggacaa tgggcgaaag cctgatccag    360
caatgccgcg tgtgtgaaga aggtcttcgg attgtaaagc actttcgacg gggacgatga    420
tgacggtacc cgtagaagaa gccccggcta acttcgtgcc agcagccgcg gtaatacgaa    480
gggggctagc gttgctcgga atgactgggc gtaaagggcg cgtaggcggt tgttacagtc    540
agatgtgaaa tccccgggct taacctggga actgcatttg atacgtgacg actagagttc    600
gagagagggt tgtggaattc ccagtgtaga ggtgaaattc gtagatattg ggaagaacac    660
cggtggcgaa ggcggcaacc tggctcgata ctgacgctga ggcgcgaaag cgtgggagc    720 aaacaggatt agataccctg gtagtccacg ctgtaaacga tgtgtgctgg atgttgggaa    780
acttagtttt tcagtgtcga agctaacgcg ctaagcacac cgcctgggga gtacggccgc    840
aaggttgaaa ctcaaaggaa ttgacggggg cccgcacaag cggtggagca tgtggtttaa    900
ttcgaagcaa cgcgcagaac cttaccaggg cttgcatggg gaggaccggt tcagagatgg    960
accttttctt ggacctcccg cacaggtgct gcatggctgt cgtcagctcg tgtcgtgaga    1020
tgttgggtta agtcccgcaa cgagcgcaac ccttgtcttt agttgccagc actttcaggt    1080
gggcactcta gagagactgc cggtgacaag ccggaggaag gtgggatga cgtcaagtcc    1140 tcatggccct tatgtcctgg gctacacacg tgctacaatg gcggtgacag tgggaagcta    1200
catggtgaca tggtgctgat ctctaaaagc cgtctcagtt cggattgtac tctgcaactc    1260
gagtacatga aggtggaatc gctagtaatc gcggatcagc atgccgcggt gaatacgttc    1320
ccgggccttg tacaccgcc cgtcacacc atgggagttg gttcgacctt aagccggtga    1380
gcgaaccgta aggacgcagc cgaccacgga cgggtcagcg actggggtga agtcgtaaca    1440
aggtagccgt aggggaacct gcggctggat cacctccttt                         1480
```

<210> SEQ ID NO 22
<211> LENGTH: 1570
<212> TYPE: DNA

<213> ORGANISM: Artificial Sequence
<220> FEATURE:
<223> OTHER INFORMATION: Synthetic

<400> SEQUENCE: 22

```
atgagagttt gatcctggct caggacgaac gctggcggcg tgcctaatac atgcaagtcg      60
aacgcgtctt ggtcaatgat tttaggtgct tgcacttgac tgatttgaca ttgagacgag     120
tggcgaactg gtgagtaaca cgtgggtaac ctgcccttga agtagaggat aacacttgga     180
aacaggtgct aatactgcat aacaacgaaa accgcctggt tttcgtttga agatggctt      240
cggctatcgc tttaggatgg acccgcggcg tattagctag ttggtgaggt aacggctcac     300
caaggcaatg atacgtagcc gacctgagag ggtaatcggc cacattggga ctgagacacg     360
gcccaaactc ctacgggagg cagcagtagg gaatcttcca caatggacga aagtctgatg     420
gagcaacgcc gcgtgagtga tgaagggttt cggctcgtaa aactctgttg ttggagaaga     480
acgggtgtca gagtaactgt tgacatcgtg acggtatcca accagaaagc cacggctaac     540
tacgtgccag cagccgcggt aatacgtagg tggcaagcgt tgtccggatt tattgggcgt     600
aaagcgagcg caggcggttt tttaggtctg atgtgaaagc cttcggctta accggagaag     660
tgcatcggaa accgggagac ttgagtgcag aagaggacag tggaactcca tgtgtagcgg     720
tgaaatgcgt agatatatgg aagaacacca gtggcgaagg cggctgtctg gtctgcaact     780
gacgctgagg ctcgaaagca tgggtagcga acaggattag ataccctggt agtccatgcc     840
gtaaacgatg agtgctaagt gttggagggt ttccgccctt cagtgctgca gctaacgcat     900
taagcactcc gcctggggag tacgaccgca aggttgaaac tcaaaggaat tgacggggc      960
ccgcacaagc ggtggagcat gtggtttaat tcgatgctac gcgaagaacc ttaccaggtc    1020
ttgacatctt ctgccaacct aagagattag gcgttccctt cggggacaga atgacaggtg    1080
gtgcatggtt gtcgtcagct cgtgtcgtga tgttgggt taagtcccgc aacgagcgca      1140
acccttattg ttagttgcca gcatttagtt gggcactcta gcaagactgc cggtgacaaa    1200
ccggaggaag gtggggatga cgtcaaatca tcatgcccct tatgacctgg gctacacacg    1260
tgctacaatg gacggtacaa cgagtcgcga accgcgagg tcaagctaat ctcttaaagc     1320
cgttctcagt tcggattgta ggctgcaact cgcctacatg aagttggaat cgctagtaat    1380
cgtggatcag catgccacgg tgaatacgtt cccgggcctt gtacaccg cccgtcacac      1440
catgagagtt tgtaacaccc aaagccggtg aggtaaccct cggggccag ccgtctaagg     1500
tgggacagat gattagggtg aagtcgtaac aaggtagccg taggagaacc tgcggctgga    1560
tcacctcctt                                                           1570
```

<210> SEQ ID NO 23
<211> LENGTH: 1561
<212> TYPE: DNA
<213> ORGANISM: Artificial Sequence
<220> FEATURE:
<223> OTHER INFORMATION: Synthetic

<400> SEQUENCE: 23

```
atgagagttt gatcctggct caggacgaac gctggcggca tgcctaatac atgcaagtcg      60
aacgagcttc cgttgaatga cgtgcttgca ctgatttcaa caatgaagcg agtggcgaac     120
tggtgagtaa cacgtgggga atctacccag aagcagggga taacttgg aaacaggtgc       180
taataccgta taacaacaaa atccgcatgg attttgtttg aaaggtggct tcggctatca     240
cttctggatg atcccgcggc gtattagtta gttggtgagg taaaggccca ccaagacgat     300
```

```
gatacgtagc cgacctgaga gggtaatcgg ccacattggg actgagacac ggcccaaact    360
cctacgggag gcagcagtag ggaatcttcc acaatggacg aaagtctgat ggagcaatgc    420
cgcgtgagtg aagaagggtt tcggctcgta aaactctgtt gttaagaag aacacctttg     480 agagtaactg ttcaagggtt gacggtattt aaccagaaag ccacggctaa ctacgtgcca    540
gcagccgcgg taatacgtag gtggcaagcg ttgtccggat ttattgggcg taaagcgagc    600
gcaggcggtt ttttaagtct gatgtgaaag ccttcggctt aaccggagaa gtgcatcgga    660
aactgggaga cttgagtgca agaggacag tggaactcc atgtgtagcg gtggaatgcg      720
tagatatatg gaagaacacc agtggcgaag gcggctgtct agtctgtaac tgacgctgag    780
gctcgaaagc atgggtagca acaggatta gataccctgg tagtccatgc cgtaaacgat     840
gagtgctaag tgttggaggg tttccgccct cagtgctgc agctaacgca ttaagcactc     900
cgcctgggga gtacgaccgc aaggttgaaa ctcaaaggaa ttgacggggg cccgcacaag    960
cggtggagca tgtggtttaa ttcgaagcta cgcgaagaac cttaccaggt cttgacatct    1020
tctgccaatc ttagagataa gacgttccct tcggggacag aatgacaggt ggtgcatggt    1080
tgtcgtcagc tcgtgtcgtg agatgttggg ttaagtcccg caacgagcgc aacccttatt    1140
atcagttgcc agcattcagt tgggcactct ggtgagactg ccggtgacaa accggaggaa    1200 ggtgggggatg acgtcaaatc atcatgcccc ttatgacctg gctacacac gtgctacaat    1260 ggacggtaca acgagtcgcg aagtcgtgag gctaagctaa tctcttaaag ccgttctcag    1320
ttcggattgt aggctgcaac tcgcctacat gaagttggaa tcgctagtaa tcgcggatca    1380
gcatgccgcg gtgaatacgt tcccgggcct tgtacacacc gcccgtcaca ccatgagagt    1440
ttgtaacacc caaagccggt gagataacct tcgggagtca gccgtctaag gtgggacaga    1500
tgattagggt gaagtcgtaa caaggtagcc gtaggagaac ctgcggctgg atcacctcct    1560
t                                                                    1561

<210> SEQ ID NO 24
<211> LENGTH: 1563
<212> TYPE: DNA
<213> ORGANISM: Artificial Sequence
<220> FEATURE:
<223> OTHER INFORMATION: Synthetic

<400> SEQUENCE: 24
tttgagagtt tgatcctggc tcaggacgaa cgctggcggc gtgcctaata catgcaagtc    60
gaacgaactc tggtattgat tggtgcttgc atcatgattt acatttgagt gagtggcgaa    120
ctggtgagta acacgtggga aacctgccca gaagcggggg ataacacctg gaaacagatg    180
ctaataccgc ataacaactt ggaccgcatg gtccgagctt gaaagatggc ttcagctatc    240 actttggat ggtcccgcgg cgtattagct agatggtggg gtaacggctc accatggcaa    300
tgatacgtag ccgacctgag agggtaatcg gccacattgg gactgagaca cggcccaaac    360
tcctacggga ggcagcagta gggaatcttc acaatggacg aaagtctga tggagcaacg     420 ccgcgtgagt gaagaagggt tcggctcgt aaaactctgt tgttaaagaa gaacatatct     480
gagagtaact gttcaggtat tgacggtatt taaccagaaa gccacggcta actacgtgcc    540
agcagccgcg gtaatacgta ggtggcaagc gttgtccgga tttattgggc gtaaagcgag    600
cgcaggcggt tttttaagtc tgatgtgaaa gccttcggct caaccgaaga agtgcatcgg    660
aaactgggaa acttgagtgc agaagaggac agtggaactc catgtgtagc ggtgaaatgc    720
```

```
gtagatatat ggaagaacac cagtggcgaa ggcggctgtc tggtctgtaa ctgacgctga    780
ggctcgaaag tatgggtagc aaacaggatt agataccctg gtagtccata ccgtaaacga    840
tgaatgctaa gtgttggagg gtttccgccc ttcagtgctg cagctaacgc attaagcatt    900
ccgcctgggg agtacggccg caaggctgaa actcaaagga attgacgggg gcccgcacaa    960
gcggtggagc atgtggttta attcgaagct acgcgaagaa ccttaccagg tcttgacata   1020
ctatgcaaat ctaagagatt agacgttccc ttcggggaca tggatacagg tggtgcatgg   1080
ttgtcgtcag ctcgtgtcgt gagatgttgg gttaagtccc gcaacgagcg caacccttat   1140
tatcagttgc cagcattaag ttgggcactc tggtgagact gccggtgaca aaccggagga   1200
aggtggggat gacgtcaaat catcatgccc cttatgacct gggctacaca cgtgctacaa   1260
tggatggtac aacgagttgc gaactcgcga gagtaagcta atctcttaaa gccattctca   1320
gttcggattg taggctgcaa ctcgcctaca tgaagtcgga atcgctagta atcgcggatc   1380
agcatgccgc ggtgaatacg ttcccgggcc ttgtacacac cgcccgtcac accatgagag   1440
tttgtaacac ccaaagtcgg tggggtaacc ttttaggaac cagccgccta aggtgggaca   1500
gatgattagg gtgaagtcgt aacaaggtag ccgtaggaga acctgcggct ggatcacctc   1560
ctt                                                                 1563
```

FERMENTED BEVERAGES AND METHODS OF PRODUCTION THEREOF

RELATED APPLICATION

This application is a continuation of U.S. non-provisional application Ser. No. 17/515,358, filed on Oct. 29, 2021, which claims the benefit under 35 U.S.C. 119(e) of U.S. provisional application No. 63/108,189, filed Oct. 30, 2020, both of which are incorporated by reference herein in their entireties.

GOVERNMENT SUPPORT

This invention was made with government support under Award Number 1940409 from the National Science Foundation. The government has certain rights in the invention.

BACKGROUND OF INVENTION

Kombucha is a fermented beverage produced by fermenting sweetened tea using a symbiotic culture of bacteria and yeast, referred to as a SCOBY. The composition of bacterial and yeast strains in a SCOBY used to produce fermented products varies and is typically serially passaged between fermentation batches. Such passaging leads to potential variation between batches and the resulting fermented beverage. Consumption of kombucha and the availability of commercial kombucha and other fermented products has recently increased and is thought to be associated with a range of beneficial health effects, such as aiding in digestion, metabolism, immunity, liver function, through delivering living microbial cultures.

SUMMARY OF INVENTION

Aspects of the present disclosure provide fermented beverages comprising a symbiotic microbial community comprising at least one bacterial strain having a 16S rDNA sequence comprising at least 95% sequence identity to a nucleic acid sequence provided by SEQ ID NOs: 1-3, and at least one bacterial strain having a16S rDNA sequence comprising at least 95% sequence identity to a nucleic acid sequence provided by SEQ ID NOs: 4-7, and at least one additional microbial strain, a sugar content that is less than 20 grams per liter (g/L), and an ethanol level that is less than 0.5% alcohol by volume (abv, v/v).

In some embodiments, the symbiotic microbial community comprises at least two, at least three, or at least four additional microbial strains. In some embodiments, at least one of the additional microbial strains is a bacterial strain. In some embodiments, each of the additional microbial strains is a bacterial strain. In some embodiments, the additional bacterial strain belongs to the genus *Lactobacillus, Gluconobacter, Leuconostoc, Acetobacter, Hafnia/Obesumbacterium, Lactococcus, Pediococcus*, or *Bacillus*. In some embodiments, the additional bacterial strain belongs to the species *Acetobacter pasteurianus, A. ghanesis, A. orientalis, A. tropicalis, Gluconobacter oxydans, G. roseus, G. japonicus, G. frateurii, Leuconostoc mesenteroides, Lactobacillus senmaizukei, L. brevis, L. parakefiri, L. hilgardii, L. diolivorans, L. rapi, L. kisonesis, L. buchneri, L. fuchuensis, L. plantarum, L. paraplantarum, L. fabifermentans, L. pentosus, L. graminis, L. composti, Bacillus zanthoxyli, B. qingshengii, B. aryabhattai, B. flexus, B. megaterium, Hafnia alvei, Obesumbacterium proteus, Lactococcus taiwanensis, L. lactis, Lactobacillus casei, L. paracasei, Pediococcus claussenii, P. stilesii, P. pentosaceus, P. acidilactici, Gluconacetobacter liquefaciens, Lactobacillus cerevisiae, L. kefiri, L. sunkii, L. otakiensis, L. parabuchneri, Leuconostoc lactis, L. palmae, L. holzapfelii, L. citreum, Lactobacillus nagelii, L. satsumensis, Acetobacter papayae, A. suratthaniensis, A. peroxydans, Gluconacetobacter takamatsuzukensis*, or *G. asukensis*. In some embodiments, the additional bacterial strain has a 16S rDNA sequence comprising at least 95% sequence identity to a nucleic acid sequence provided by SEQ ID NOs: 8-19.

In some embodiments, the symbiotic microbial community comprises bacterial strains having a 16S rDNA sequence comprising at least 95% sequence identity to a nucleic acid sequence provided by SEQ ID NOs: 2, 4, 5, 6, 7, and 20-24. In some embodiments, the symbiotic microbial community consists of bacterial strains having a 16S rDNA sequence comprising at least 95% sequence identity to a nucleic acid sequence provided by SEQ ID NOs: 2, 5, 6, and 7.

In some embodiments, the symbiotic microbial community comprises bacterial strains having a 16S rDNA sequence comprising at least 95% sequence identity to a nucleic acid sequence provided by SEQ ID NOs: 2, 4, and 5. In some embodiments, the symbiotic microbial community consists of bacterial strains having a 16S rDNA sequence comprising at least 95% sequence identity to a nucleic acid sequence provided by SEQ ID NOs: 2, 4, and 5.

In some embodiments, the symbiotic microbial community comprises bacterial strains having a 16S rDNA sequence comprising at least 95% sequence identity to a nucleic acid sequence provided by SEQ ID NOs: 21, 20, 22, and 24. In some embodiments, the symbiotic microbial community comprises bacterial strains having a 16S rDNA sequence comprising at least 95% sequence identity to a nucleic acid sequence provided by SEQ ID NOs: 21, 23, and 20.

In some embodiments, the symbiotic microbial community consists of bacterial strains having a 16S rDNA sequence comprising at least 95% sequence identity to a nucleic acid sequence provided by SEQ ID NOs: 21, 20, 22, and 24. In some embodiments, the symbiotic microbial community consists of bacterial strains having a 16S rDNA sequence comprising at least 95% sequence identity to a nucleic acid sequence provided by SEQ ID NOs: 21, 23, and 20.

In some embodiments, the symbiotic microbial community comprises bacterial strains having a 16S rDNA sequence comprising at least 95% sequence identity to a nucleic acid sequence provided by SEQ ID NOs: 2, 4, 5, and 7. In some embodiments, the symbiotic microbial community consists of bacterial strains having a 16S rDNA sequence comprising at least 95% sequence identity to a nucleic acid sequence provided by SEQ ID NOs: 2, 4, 5, and 7.

In some embodiments, the symbiotic microbial community comprises bacterial strains having a 16S rDNA sequence comprising at least 95% sequence identity to a nucleic acid sequence provided by SEQ ID NOs: 21, 23, 20, and 24. In some embodiments, the symbiotic microbial community consists of bacterial strains having a 16S rDNA sequence comprising at least 95% sequence identity to a nucleic acid sequence provided by SEQ ID NOs: 21, 23, 20, and 24.

In some embodiments, the symbiotic microbial community does not comprise a yeast strain. In some embodiments, the symbiotic microbial community comprises at least $2 \times 10^7$ colony forming units of each bacterial strain and each additional microbial strain per milliliter of the fermented beverage.

In some embodiments, the fermented beverage comprises a level of acetic acid less than 1 gram per liter (g/L). In some embodiments, the fermented beverage comprises a level of organic acid that is greater than 1 gram per liter (g/L), wherein the organic acid is not acetic acid. In some embodiments, the organic acid is lactic acid, gluconic acid, keto-gluconic acid, or a combination thereof.

In some embodiments, the fermented beverage is shelf stable for at least 2 weeks at a temperature of about 20° C. In some embodiments, the fermented beverage is shelf stable for at least 1 week at a temperature of about 40° C. In some embodiments, the pH of the fermented beverage is less than about 3.5.

In some embodiments, the fermented beverage is kombucha, seltzer, soda, gut shot, water kefir, jun, fruit juice, vegetable juice, ginger beer, a flavored water product, or a probiotic beverage. In some embodiments, at least one of the microbial strains is derived from a fermented food product. In some embodiments, each of the microbial strains is derived from a fermented food product.

In some embodiments, the bacterial strains and the additional microbial strains are live in the fermented beverage. In some embodiments, the fermented beverage further comprises one or more additional components. In some embodiments, the additional component is a vitamin, mineral, or flavoring additives. In some embodiments, the one or more additional component is selected from the group consisting of black tea, green tea, fruit juice, and vegetable juice.

Aspects of the present disclosure provide methods of producing a fermented food beverage, comprising (i) providing a medium comprising a fermentable sugar at an initial sugar level; (ii) adding a symbiotic microbial community to the medium to produce a culture, wherein the symbiotic microbial community comprises at least one bacterial strain having a 16S rDNA sequence comprising at least 95% sequence identity to a nucleic acid sequence provided by SEQ ID NOs: 1-3, and at least one bacterial strain having a16S rDNA sequence comprising at least 95% sequence identity to a nucleic acid sequence provided by SEQ ID NOs: 4-7, and at least one additional microbial strain; and (iii) fermenting the culture under conditions to produce a fermented beverage.

In some embodiments, the symbiotic microbial community comprises at least two, at least three, or at least four additional microbial strains. In some embodiments, at least one of the additional microbial strains is a bacterial strain. In some embodiments, each of the additional microbial strains is a bacterial strain. In some embodiments, the additional bacterial strain belongs to the genus *Lactobacillus, Gluconobacter, Leuconostoc, Acetobacter, Hafnia/Obesumbacterium, Lactococcus, Pediococcus*, or *Bacillus*. In some embodiments, the additional bacterial strain belongs to the species *Acetobacter pasteurianus, A. ghanesis, A. orientalis, A. tropicalis, Gluconobacter oxydans, G. roseus, G. japonicus, G. frateurii, Leuconostoc mesenteroides, Lactobacillus senmaizukei, L. brevis, L. parakefiri, L. hilgardii, L. diolivorans, L. rapi, L. kisonesis, L. buchneri, L. fuchuensis, L. plantarum, L. paraplantarum, L. fabifermentans, L. pentosus, L. graminis, L. composti, Bacillus zanthoxyli, B. qingshengii, B. aryabhattai, B. flexus, B. megaterium, Hafnia alvei, Obesumbacterium proteus, Lactococcus taiwanensis, L. lactis, Lactobacillus casei, L. paracasei, Pediococcus claussenii, P. stilesii, P. pentosaceus, P. acidilactici, Gluconacetobacter liquefaciens, L. cerevisiae, L. kefiri, L. sunkii, L. otakiensis, L. parabuchneri, Leuconostoc lactis, L. palmae, L. holzapfelii, L. citreum, Lactobacillus nagelii, L. satsumensis, Acetobacter papayae, A. suratthaniensis, A. peroxydans, Gluconacetobacter takamatsuzukensis*, or *G. asukensis*. In some embodiments, the additional bacterial strain has a 16S rDNA sequence comprising at least 95% sequence identity to a nucleic acid sequence provided by SEQ ID NOs: 8-19. In some embodiments, the symbiotic microbial community comprises bacterial strains having a 16S rDNA sequence comprising at least 95% sequence identity to a nucleic acid sequence provided by SEQ ID NOs: 2, 4, 5, 6, 7, and 20-24.

In some embodiments, the symbiotic microbial community comprises bacterial strains having a 16S rDNA sequence comprising at least 95% sequence identity to a nucleic acid sequence provided by SEQ ID NOs: 2, 5, 6, and 7. In some embodiments, the symbiotic microbial community consists of bacterial strains having a 16S rDNA sequence comprising at least 95% sequence identity to a nucleic acid sequence provided by SEQ ID NOs: 2, 5, 6, and 7.

In some embodiments, the symbiotic microbial community comprises bacterial strains having a 16S rDNA sequence comprising at least 95% sequence identity to a nucleic acid sequence provided by SEQ ID NOs: 2, 4, and 5. In some embodiments, the symbiotic microbial community consists of bacterial strains having a 16S rDNA sequence comprising at least 95% sequence identity to a nucleic acid sequence provided by SEQ ID NOs: 2, 4, and 5.

In some embodiments, the symbiotic microbial community comprises bacterial strains having a 16S rDNA sequence comprising at least 95% sequence identity to a nucleic acid sequence provided by SEQ ID NOs: 21, 20, 22, and 24. In some embodiments, the symbiotic microbial community consists of bacterial strains having a 16S rDNA sequence comprising at least 95% sequence identity to a nucleic acid sequence provided by SEQ ID NOs: 21, 20, 22, and 24.

In some embodiments, the symbiotic microbial community comprises bacterial strains having a 16S rDNA sequence comprising at least 95% sequence identity to a nucleic acid sequence provided by SEQ ID NOs: 21, 23, and 20. In some embodiments, the symbiotic microbial community consists of bacterial strains having a 16S rDNA sequence comprising at least 95% sequence identity to a nucleic acid sequence provided by SEQ ID NOs: 21, 23, and 20.

In some embodiments, the symbiotic microbial community comprises bacterial strains having a 16S rDNA sequence comprising at least 95% sequence identity to a nucleic acid sequence provided by SEQ ID NOs: 2, 4, 5, and 7. In some embodiments, the symbiotic microbial community consists of bacterial strains having a 16S rDNA sequence comprising at least 95% sequence identity to a nucleic acid sequence provided by SEQ ID NOs: 2, 4, 5, and 7.

In some embodiments, the symbiotic microbial community comprises bacterial strains having a 16S rDNA sequence comprising at least 95% sequence identity to a nucleic acid sequence provided by SEQ ID NOs: 21, 23, 20, and 24. In some embodiments, the symbiotic microbial community consists of bacterial strains having a 16S rDNA sequence comprising at least 95% sequence identity to a nucleic acid sequence provided by SEQ ID NOs: 21, 23, 20, and 24.

In some embodiments, the symbiotic microbial community does not comprise a yeast strain. In some embodiments, the symbiotic microbial community comprises at least $2 \times 10^7$ colony forming units of each bacterial strain and each additional microbial strain per milliliter of the fermented beverage.

In some embodiments, the fermented beverage comprises a level of acetic acid less than 1 gram per liter (g/L). In some embodiments, the fermented beverage comprises a level of organic acid that is greater than 1 gram per liter (g/L), wherein the organic acid is not acetic acid. In some embodiments, the organic acid is lactic acid, gluconic acid, ketogluconic acid, or a combination thereof.

In some embodiments, the fermented beverage is shelf stable for at least 2 weeks at a temperature of about 20° C. In some embodiments, the fermented beverage is shelf stable for at least 1 week at a temperature of about 40° C. In some embodiments, the pH of the fermented beverage is less than about 3.5.

In some embodiments, the fermented beverage is kombucha, seltzer, soda, gut shot, water kefir, jun, fruit juice, vegetable juice, ginger beer, a flavored water product, or a probiotic beverage.

In some embodiments, at least one of the microbial strains is derived from a fermented food product. In some embodiments, each of the microbial strains is derived from a fermented food product. In some embodiments, the bacterial strains and the additional microbial strains are live in the fermented beverage.

In some embodiments, the fermented beverage further comprises one or more additional components. In some embodiments, the additional component is a vitamin, mineral, or flavoring additives. In some embodiments, the one or more additional component is selected from the group consisting of black tea, green tea, fruit juice, and vegetable juice. In some embodiments, the fermented beverage has a pH less than about 3.5.

In some embodiments, the fermenting is performed in a batch reactor. In some embodiments, the fermenting is performed at about 18-37° C. In some embodiments, the fermenting is performed for at least 6 days at about 20° C.

In some embodiments, the initial sugar level is 2.5-20 grams per liter (g/L) of a sugar source. In some embodiments, the initial sugar level is about 10 grams per liter (g/L) of a sugar source. In some embodiments, the sugar source is a cane sugar, palm sugar, maple syrup, fruit juice, vegetable juice, brown sugar, molasses, agave nectar, honey, date syrup, date paste, date sugar, coconut sugar, or coconut water.

In some embodiments, the bacterial strains and the additional microbial strain(s) replicate faster when in the symbiotic microbial community compared to when not in the symbiotic microbial community. In some embodiments, the bacterial strains and the additional microbial strain(s) grow to a higher biomass when in the symbiotic microbial community compared to when not in the symbiotic microbial community. In some embodiments, the symbiotic microbial community comprises at least $2 \times 10^5$ colony forming units. In some embodiments, the biomass of the symbiotic microbial community is stable over at least 60 days. In some embodiments, the symbiotic microbial community reduces or prevents growth of undesired microbial strains.

In some embodiments, the method further comprises carbonating the fermented beverage to produce a carbonated fermented beverage.

Aspects of the present disclosure provide fermented beverage obtained or obtainable by any of the methods described herein.

BRIEF DESCRIPTION OF DRAWINGS

It is to be understood that the Figures are not necessarily to scale, emphasis instead being placed upon generally illustrating the various concepts discussed herein.

FIGS. 5A and 5B show terminal sugar levels as the total sugar per 8 oz serving. Each plot shows mean and standard deviation of 3 biological replicates. The dotted line indicates 0.5 g, which corresponds to the threshold to be considered a "zero-sugar" food or beverage product for the U.S. Food and Drug Administration.

DETAILED DESCRIPTION OF INVENTION

Figure 1B:
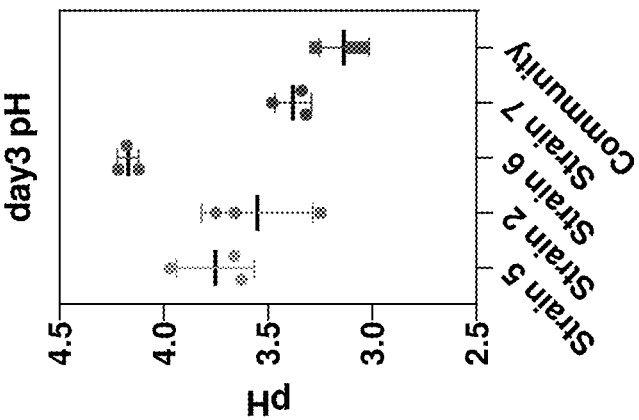
FIG. 1B shows the pH of fermentation reactions performed using the indicated individual microbial strains or the microbial community ("Community") at day 3. Each plot shows mean and standard deviation of 3 biological replicates. Strain 5 corresponds to SEQ ID NO: 5; Strain 2 corresponds to SEQ ID NO: 2; Strain 6 corresponds to SEQ ID NO: 6; and Strain 7 corresponds to SEQ ID NO: 7. Community corresponds to a microbial community containing Strains 5, 2, 6, and 7.

Kombucha and other fermented beverages, such as kefirs and ginger beers, that contain living cultures are often considered "health beverages" and alternatives to other non-alcoholic or low alcohol content beverages. However, these products, like many soda products, are frequently high in sugar with upwards of 12-15 grams per serving. The fermentation process used for kombucha production is not highly scalable to large scale bioreactors and typically must be fermented in batch in small reactors/containers. The microbial communities utilized to produce kombucha are not defined and typically include hundreds of microbial strains. These communities can vary batch to batch, resulting in fluctuations in taste, flavor and inability to scale production in a rational and predictable manner. The organisms used to produce Kombucha also can result in final products with relatively high levels of alcohol that may be higher than the U.S. federal limit for non-alcoholic products (i.e., 0.5% ABV).

Additionally, kombucha must be maintained at reduced (refrigerated) temperatures for storage prior to consumption. The need for cold-chain distribution vastly increases the cost associated with commercially available kombucha products and limits the ability of manufacturers to successfully compete in the soda market, which is estimated to be a much larger market by at least two orders of magnitude.

In addition, the fermentation process for producing kombucha involves culturing a symbiotic culture of bacterial and yeast, referred to as a SCOBY, and passaging the SCOBY between serial fermentation batches. A frequent product of the fermentation process using a SCOBY is acetic acid, which can impart an undesired flavor profile characterized as "vinegar-like." This strong, sometimes off-putting, flavor may also limit consumer acceptability and correspondingly the size of the target market.

The present disclosure is based, at least in part, on the development of symbiotic microbial communities and fermentation methods of using such microbial communities to produce fermented products having desired properties. In contrast to typical microbial communities used in the production of fermented beverages such as kombucha as well as single strain fermentation approaches, the symbiotic microbial communities described herein provide a number of advantages, including fermenting sugars more quickly; increased resistance to invasion of the fermentation culture by environmental pathogens/contaminants; imparting complex and appealing flavor profiles to the fermented beverage, including low to no acetic acid and high levels of lactic acid and gluconic acids; producing a fermented beverage with very low to no ethanol in the finished product; and providing a diverse population of living microbial cultures in the fermented beverage for consumption. The fermented products described herein may be characterized as having a more fruity and appealing taste profile as compared to vinegar-like and strong flavor typically associated with kombucha products. The synergistic interactions between the microbial strains of the symbiotic microbial communities described herein are particularly unexpected as each of the microbial strains were obtained from and evolved in different naturally fermented food sources.

Provided herein are fermented beverages comprising a symbiotic microbial community and having reduced sugar content and reduced levels of alcohol. Also provided herein are methods of producing fermented beverages involving providing a medium comprising a fermentable sugar and adding any of the symbiotic microbial community described herein and fermenting the culture to produce a fermented beverage.

Symbiotic Microbial Communities

Aspects of the present disclosure provide symbiotic microbial communities, fermented beverages comprising such microbial communities, and methods of producing fermented beverages involving a fermentation process using the microbial communities. As used herein, the term "symbiotic microbial community" refers to a plurality of microbial strains that when grown or cultured together have a symbiotic relationship, which leads to the production of a fermented product having desired properties. As used herein, the term "symbiotic relationship" refers to a relationship between two or more microbial strains that have a positive interaction in which at least one of the microbial strains benefits from the relationship. In some embodiments, the symbiotic relationship is a mutualistic relationship in which both microbial strains (or in the context of more than two microbial strains, all microbial strains) benefit from the relationship.

In contrast to fermented beverages that are produced using naturally occurring microbial communities, such as a SCOBY, which are typically undefined communities and/or have varying microbial composition that may change during passaging, the composition of the microbial communities of the present disclosure are defined and rationally designed to achieve fermented beverages having desired properties (e.g., reduced sugar content, low alcohol content, complex flavor profiles, shelf stability). For example, the microbial species are obtained from distinct sources and relative amounts of each of the microbial strains are controlled and relatively uniform between disparate fermentation batches.

In some embodiments, the symbiotic microbial communities described herein comprise two or more microbial strains. In some embodiments, the compositions described herein comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or up to 20 total microbial strains.

It will be appreciated that the terms "microbial strains," "microbes," "microbial cells" and "microorganisms" are used interchangeably herein. In some embodiments, one or more (e.g., 1, 2, 3, 4, 5, or more) of the microbial strains of the symbiotic microbial community are bacterial strains. In some embodiments, all of the microbial strains of the symbiotic microbial community are bacterial strains. In some embodiments, one or more (e.g., 1, 2, 3, 4, 5, or more) of the microbial strains of the symbiotic microbial community are yeast strains. In some embodiments, the symbiotic microbial community does not contain yeast strains. In some embodiments, the symbiotic microbial community does not contain a yeast strain of the Brettanomyces genus. In some embodiments, the symbiotic microbial community does not contain a yeast strain of the *Saccharomyces* genus. In some embodiments, the symbiotic microbial community does not contain a yeast strain of the *Starmerella* genus.

The symbiotic microbial communities of the present disclosure comprise at least one microbial strain (e.g., 1, 2, 3, 4, 5, or more) having a 16S rDNA sequence comprising at least 95% sequence identity to the nucleic acid sequence provided by SEQ ID NOs: 1-3 and at least one microbial strain (e.g., 1, 2, 3, 4, 5, or more) having a 16S rDNA sequence comprising at least 95% sequence identity to the nucleic acid sequence provided by SEQ ID NOs: 4-7. The symbiotic microbial communities of the present disclosure comprise at least one microbial strain (e.g., 1, 2, 3, 4, 5, or more) having a 16S rDNA sequence comprising at least 95% sequence identity to the nucleic acid sequence provided by SEQ ID NOs: 1-3 and one microbial strain having a 16S rDNA sequence comprising at least 95% sequence identity to the nucleic acid sequence provided by SEQ ID NOs: 4-7. The symbiotic microbial communities of the present disclosure comprise one microbial strain having a 16S rDNA sequence comprising at least 95% sequence identity to the nucleic acid sequence provided by SEQ ID NOs: 1-3 and at least one microbial strain (e.g., 1, 2, 3, 4, 5, or more) having a 16S rDNA sequence comprising at least 95% sequence identity to the nucleic acid sequence provided by SEQ ID NOs: 4-7.

In some embodiments, the symbiotic microbial communities of the present disclosure consist of at least one microbial strain (e.g., 1, 2, 3, 4, 5, or more) having a 16S rDNA sequence comprising at least 95% sequence identity to the nucleic acid sequence provided by SEQ ID NOs: 1-3 and at least one microbial strain (e.g., 1, 2, 3, 4, 5, or more) having a 16S rDNA sequence comprising at least 95% sequence identity to the nucleic acid sequence provided by SEQ ID NOs: 4-7.

Microbial strains used to produce the fermented beverages in the methods described herein were classified into operational taxonomic units (OTUs) on the basis of sequence similarity. Representative sequences from each OTU were compared with sequences in publicly available nucleic acid databases, such as Basic Local Alignment Search Tool (BLAST) to determine closely related genera and species and were analyzed using taxonomic assignment tools, such as RDP Classifier, which assign bacterial taxonomy to representative sequences. Ribosomal 16S DNA sequences are provided below for representative microbial strains.

In some embodiments, the symbiotic microbial communities of the present disclosure comprise at least one microbial strain having a 16S rDNA sequence comprising at least 95% sequence identity to the nucleic acid sequence provided by SEQ ID NOs: 1-3 and at least one microbial strain having a 16S rDNA sequence comprising at least 95% sequence identity to the nucleic acid sequence provided by SEQ ID NOs: 4-7 and at least two, at least three, at least four, at least five, at least six, at least seven, at least eight, at least nine, at least ten or more additional microbial strains.

In some embodiments, the symbiotic microbial communities of the present disclosure consist of at least one microbial strain having a 16S rDNA sequence comprising at least 95% sequence identity to the nucleic acid sequence provided by SEQ ID NOs: 1-3 and at least one microbial strain having a 16S rDNA sequence comprising at least 95% sequence identity to the nucleic acid sequence provided by SEQ ID NOs: 4-7 and at least two, at least three, at least four, at least five, at least six, at least seven, at least eight, at least nine, at least ten or more additional microbial strains.

Any of the symbiotic microbial communities described herein may further comprise one or more additional microbial strain, such as a microbial strain belonging to the genus *Leuconostoc, Obseumbacterium, Lactococcus, Bacillus, Lactobacillus, Acetobacter*, or *Gluconobacter*. In some embodiments, the symbiotic microbial communities of the present disclosure comprise at least one microbial strain having a 16S rDNA sequence comprising at least 95% sequence identity to the nucleic acid sequence provided by SEQ ID NOs: 1-3 and at least one microbial strain having a 16S rDNA sequence comprising at least 95% sequence identity to the nucleic acid sequence provided by SEQ ID NOs: 4-7 and one or more additional microbial strain, such as a microbial strain belonging to the genus *Leuconostoc, Obseumbacterium, Lactococcus, Bacillus, Lactobacillus, Acetobacter*, or *Gluconobacter*. In some embodiments, the symbiotic microbial communities of the present disclosure comprise at least one microbial strain having a 16S rDNA sequence comprising at least 95% sequence identity to the nucleic acid sequence provided by SEQ ID NOs: 1-3 and 21 and at least one microbial strain having a 16S rDNA sequence comprising at least 95% sequence identity to the nucleic acid sequence provided by SEQ ID NOs: 4-7, 20, 22, 23, and 24 and additional microbial strains belonging to the genus *Leuconostoc, Obseumbacterium, Hafnia, Lactococcus, Bacillus, Lactobacillus, Acetobacter, Pediococcus*, or *Gluconobacter*.

Any of the symbiotic microbial communities described herein may further comprise one or more additional microbial strain, such as a microbial strain having a 16S rDNA sequence provided by any one of the nucleic acid sequences of SEQ ID NOs: 8-19. In some embodiments, the symbiotic microbial communities of the present disclosure comprise at least one microbial strain having a 16S rDNA sequence comprising at least 95% sequence identity to the nucleic acid sequence provided by SEQ ID NOs: 1-3 and 21 and at least one microbial strain having a 16S rDNA sequence comprising at least 95% sequence identity to the nucleic acid sequence provided by SEQ ID NOs: 4-7, 20, 22, 23, and 24 and one or more additional microbial strain, such as a microbial strain having a 16S rRNA sequence provided by any one of the nucleic acid sequences of SEQ ID NOs: 8-19. In some embodiments, the symbiotic microbial communities of the present disclosure comprise at least one microbial strain having a 16S rDNA sequence comprising at least 95% sequence identity to the nucleic acid sequence provided by SEQ ID NOs: 1-3 and 21 and at least one microbial strain having a 16S rDNA sequence comprising at least 95% sequence identity to the nucleic acid sequence provided by SEQ ID NOs: 4-7, 20, 22, 23, and 24 such as a microbial strain having a 16S rRNA sequence provided by any one of the nucleic acid sequences of SEQ ID NOs: 8-18.

Ribosomal 16S DNA sequences are provided below for representative microbial strains. The closest related identified bacterial species were determined based on whole genome sequence analysis and a combination of analysis of full length 16S rDNA sequences and the sequences of several housekeeping genes (e.g., dnaK, dnaJ, mutL) compared to publicly available sequence databases. It should be appreciated that multiple bacterial strains disclosed herein may have the highest homology with the same species. It should further be appreciated that the bacterial strains disclosed herein that have a 16S rDNA sequence with a nucleic acid sequence selected from the group consisting of SEQ ID NOs:1-24, are also homologous to other strains based on their whole genome sequence, or subset of their whole genome sequence.

The bacterial strain comprising a 16S rDNA sequence provided by SEQ ID NO: 1 (also referred to herein as "strain 1") has the highest homology with a bacterial strain of the species *Acetobacter pasteurianus, A. ghanesis, A. orientalis*, or *A. tropicalis*:

Strain 1
(SEQ ID NO: 1)
TACGAAGGGGGCTAGCGTTGCTCGGAATGACTGGGCGTAAAGGGCGTGT
AGGCGGTTTGTACAGTCAGATGTGAAATCCCCGGGCTTAACCTGGGAGC
TGCATTTGATACGTGCAGACTAGAGTGTGAGAGA The bacterial strain comprising a 16S rDNA sequence provided by SEQ ID NO: 2 (also referred to herein as "strain 2") has the highest homology with a bacterial strain of the species *Gluconobacter oxydans* or *G. roseus*.

Strain 2
(SEQ ID NO: 2)
TACGAAGGGGGCTAGCGTTGCTCGGAATGACTGGGCGTAAAGGGCGCGT
AGGCGGTTGTTACAGTCACATGTGAAATCCCCGGGCTTAACCTGGGAAC
TGCATTTGATACGTGACGACTAGAGTTCGAGAGA The bacterial strain comprising a 16S rDNA sequence provided by SEQ ID NO: 3 (also referred to herein as "strain 3") has the highest homology with a bacterial strain of the species *Gluconobacter japonicus*, or *G. frateurii*.

Strain 3
(SEQ ID NO: 3)
TACGAAGGGGGCTAGCGTTGCTCGGAATGACTGGGCGTAAAGGGCGCGT
AGGCGGTTGATGCAGTCAGATGTGAAATCCCCGGGCTTAACCTGGGAAC
TGCATTTGAGACGCATTGACTAGAGTTCGAGAGA The bacterial strain comprising a 16S rDNA sequence provided by SEQ ID NO: 4 (also referred to herein as "strain 4") has the highest homology with a bacterial strain of the species *Lactobacillus senmaizukei* or *L. brevis*.

Strain 4
(SEQ ID NO: 4)
TACGTAGGTGGCAAGCGTTGTCCGGATTTATTGGGCGTAAAGCGAGCGC
AGGCGGTTTTTTAAGTCTGATGTGAAAGCCTTCGGCTTAACCGGAGAAG
TGCATCGGAAACTGGGAGACTTGAGTGCAGAAGA The bacterial strain comprising a 16S rDNA sequence provided by SEQ ID NO: 5 (also referred to herein as "strain 5") has the highest homology with a bacterial strain of the species *Leuconostoc mesenteroides*.

Strain 5
(SEQ ID NO: 5)
TACGTATGTCCCGAGCGTTATCCGGATTTATTGGGCGTAAAGCGAGCGC
AGACGGTTTATTAAGTCTGATGTGAAAGCCCGGAGCTCAACTCCGGAAT
GGCATTGGAAACTGGTTAACTTGAGTGCAGTAGA The bacterial strain comprising a 16S rDNA sequence provided by SEQ ID NO: 6 (also referred to herein as "strain 6") has the highest homology with a bacterial strain of the species *Lactobacillus parakefiri, L. hilgardii, L. diolivorans, L. rapi, L. kisonesis*, or *L. buchneri*.

Strain 6
(SEQ ID NO: 6)
TACGTAGGTGGCAAGCGTTGTCCGGATTTATTGGGCGTAAAGCGAGCG

CAGGCGGTTTTTTAGGTCTGATGTGAAAGCCTTCGGCTTAACCGGAGA

AGTGCATCGGAAACCGGGAGACTTGAGTGCAGAAGA

The bacterial strain comprising a 16S rDNA sequence provided by SEQ ID NO: 7 (also referred to herein as "strain 7") has the highest homology with a bacterial strain of the species *Lactobacillus fuchuensis, L. plantarum, L. paraplantarum, L. fabifermentans, L. pentosus, L. graminis*, or *L. composti*.

Strain 7
(SEQ ID NO: 7)
TACGTAGGTGGCAAGCGTTGTCCGGATTTATTGGGCGTAAAGCGAGCG

CAGGCGGTTTTTTAAGTCTGATGTGAAAGCCTTCGGCTCAACCGAAGA

AGTGCATCGGAAACTGGGAAACTTGAGTGCAGAAGA

The bacterial strain comprising a 16S rDNA sequence provided by SEQ ID NO: 8 (also referred to herein as "strain 8") has the highest homology with a bacterial strain of the species *Bacillus zanthoxyli, B. qingshengii, B. aryabhattai, B. flexus*, or *B. megaterium*:

Strain 8
(SEQ ID NO: 8)
TACGTAGGTGGCAAGCGTTATCCGGAATTATTGGGCGTAAAGCGCGCG

CAGGCGGTTTCTTAAGTCTGATGTGAAAGCCCACGGCTCAACCGTGGA

GGGTCATTGGAAACTGGGGAACTTGAGTGCAGAAGA

The bacterial strain comprising a 16S rDNA sequence provided by SEQ ID NO: 9 (also referred to herein as "strain 9") has the highest homology with a bacterial strain of the species *Hafnia alvei* or *Obesumbacterium proteus*.

Strain 9
(SEQ ID NO: 9)
TACGGAGGGTGCAAGCGTTAATCGGAATTACTGGGCGTAAAGCGCACG

CAGGCGGTTGATTAAGTCAGATGTGAAATCCCCGAGCTTAACTTGGGA

ACTGCATTTGAAACTGGTCAGCTAGAGTCTTGTAGA

The bacterial strain comprising a 16S rDNA sequence provided by SEQ ID NO: 10 (also referred to herein as "strain 10") has the highest homology with a bacterial strain of the species *Lactococcus taiwanensis* or *L. lactis*:

Strain 10
(SEQ ID NO: 10)
TACGTAGGTCCCGAGCGTTGTCCGGATTTATTGGGCGTAAAGCGAGCG

CAGGTGGTTTATTAAGTCTGGTGTAAAAGGCAGTGGCTCAACCATTGT

ATGCATTGGAAACTGGTAGACTTGAGTGCAGGAGAG

The bacterial strain comprising a 16S rDNA sequence provided by SEQ ID NO: 11 (also referred to herein as "strain 11") has the highest homology with a bacterial strain of the species *Lactobacillus casei*, or *L. paracasei*.

Strain 11
(SEQ ID NO: 11)
TACGTAGGTGGCAAGCGTTATCCGGATTTATTGGGCGTAAAGCGAGCG

CAGGCGGTTTTTTAAGTCTGATGTGAAAGCCCTCGGCTTAACCGAGGA

AGCGCATCGGAAACTGGGAAACTTGAGTGCAGAAGA

The bacterial strain comprising a 16S rDNA sequence provided by SEQ ID NO: 12 (also referred to herein as "strain 12") has the highest homology with a bacterial strain of the species *Pediococcus claussenii, P. stilesii, P. pentosaceus*, or *P. acidilactici*.

Strain 12
(SEQ ID NO: 12)
TACGTAGGTGGCAAGCGTTATCCGGATTTATTGGGCGTAAAGCGAGCG

CAGGCGGTCTTTTAAGTCTAATGTGAAAGCCTTCGGCTCAACCGAAGA

AGTGCATTGGAAACTGGGAGACTTGAGTGCAGAAGA

The bacterial strain comprising a 16S rDNA sequence provided by SEQ ID NO: 13 (also referred to herein as "strain 13") has the highest homology with a bacterial strain of the species *Gluconacetobacter liquefaciens*.

Strain 13
(SEQ ID NO: 13)
TACGAAGGGGGCTAGCGTTGCTCGGAATGACTGGGCGTAAAGGGCGCG

TAGGCGGTATGGACAGTCAGATGTGAAATTCCTGGGCTTAACCTGGGG

GCTGCATTTGATACGTCCAAACTAGAGTGTGAGAGA

The bacterial strain comprising a 16S rDNA sequence provided by SEQ ID NO: 14 (also referred to herein as "strain 14") has the highest homology with a bacterial strain of the species *Lactobacillus cerevisiae*.

Strain 14
(SEQ ID NO: 14)
TACGTAGGTGGCAAGCGTTGTCCGGATTTATTGGGCGTAAAGCGAGCG

CAGGCGGTTTCTTAAGTCTGATGTGAAAGCCTTCGGCTTAACCGGAGA

AGTGCATCGGAAACTGGGTAACTTGAGTGCAGAAGA

The bacterial strain comprising a 16S rDNA sequence provided by SEQ ID NO: 15 (also referred to herein as "strain 15") has the highest homology with a bacterial strain of the species *Lactobacillus kefiri, L. sunkii, L. otakiensis*, or *L. parabuchneri*.

Strain 15
(SEQ ID NO: 15)
TACGTAGGTGGCAAGCGTTGTCCGGATTTATTGGGCGTAAAGCGAGCG

CAGGCGGTTTCTTAGGTCTGATGTGAAAGCCTTCGGCTTAACCGGAGA

AGTGCATCGGAAACCAGGAGACTTGAGTGCAGAAGA

The bacterial strain comprising a 16S rDNA sequence provided by SEQ ID NO: 16 (also referred to herein as "strain 16") has the highest homology with a bacterial strain of the species *Leuconostoc lactis, L. palmae, L. holzapfelii*, or *L. citreum*.

Strain 16
(SEQ ID NO: 16)
TACGTATGTCCCGAGCGTTATCCGGATTTATTGGGCGTAAAGCGAGCG

CAGACGGTTGATTAAGTCTGATGTGAAAGCCCGGAGCTCAACTCCGGA

ATGGCATTGGAAACTGGTTAACTTGAGTGTTGTAGA

The bacterial strain comprising a 16S rDNA sequence provided by SEQ ID NO: 17 (also referred to herein as "strain 17") has the highest homology with a bacterial strain of the species *Lactobacillus nagelii* or *L. satsumensis*.

Strain 17

(SEQ ID NO: 17)

TACGTAGGTGGCAAGCGTTGTCCGGATTTATTGGGCGTAAAGGGAACG

CAGGCGGTCTTTTAAGTCTGATGTGAAAGCCTTCGGCTTAACCGAAGT

CGTGCATTGGAAACTGGGAGACTTGAGTGCAGAAGA

The bacterial strain comprising a 16S rDNA sequence provided by SEQ ID NO: 18 (also referred to herein as "strain 18") has the highest homology with a bacterial strain of the species *Acetobacter papayae*, *A. suratthaniensis*, or *A. peroxydans*.

Strain 18

(SEQ ID NO: 18)

TACGAAGGGGGCTAGCGTTGCTCGGAATGACTGGGCGTAAAGGGCGTG

TAGGCGGTTTTGACAGTCAGATGTGAAATCCCCGGGCTTAACCTGGGA

GCTGCATTTGAGACGTTAAGACTAGAGTGTGAGAGA

The bacterial strain comprising a 16S rDNA sequence provided by SEQ ID NO: 19 (also referred to herein as "strain 19") has the highest homology with a bacterial strain of the species *Gluconacetobacter takamatsuzukensis* or *G. asukensis*:

Strain 19

(SEQ ID NO: 19)

TACGAAGGGGGCTAGCGTTGCTCGGAATGACTGGGCGTAAAGGGCGCG

TAGGCGGTTTGGACAGTCAGATGTGAAATTCCTGGGCTTAACCTGGGG

GCTGCATTTGATACGTCCAGACTAGAGTGTGAGAGA

It should further be appreciated that the bacterial species described herein may be identified based on the nucleotide sequence of the full length 16S rDNA, as provided below. Alternatively or in addition, the bacterial species described herein may be identified based on identification of 16S sequences through whole genome sequencing, and by comparing the sequences with 16S databases, or comparing the whole genome sequence, or a subset of their whole genome sequence to sequence databases.

Full length 16S rDNA sequences are provided below for representative species.

Strain 5 - 16S ribosomal DNA (SEQ ID NO: 20) - *Leuconostoc mesenteroides*.
ATTGAGAGTTTGATCCTGGCTCAGGATGAACGCTGGCGGCGTGCCTAATACATGCAAGTCGAACGCACAGCGAAA

GGTGCTTGCACCTTTCAAGTGAGTGGCGAACGGGTGAGTAACACGTGGACAACCTGCCTCAAGGCTGGGGATAAC

ATTTGGAAACAGATGCTAATACCGAATAAAACTTAGTGTCGCATGACACAAAGTTAAAAGGCGCTTCGGCGTCAC

CTAGAGATGGATCCGCGGTGCATTAGTTAGTTGGTGGGGTAAAGGCCTACCAAGACAATGATGCATAGCCGAGTT

GAGAGACTGATCGGCCACATTGGGACTGAGACACGGCCCAAACTCCTACGGGAGGCTGCAGTAGGGAATCTTCCA

CAATGGGCGAAAGCCTGATGGAGCAACGCCGCGTGTGTGATGAAGGCTTTCGGGTCGTAAAGCACTGTTGTATGG

GAAGAACAGCTAGAATAGGAAATGATTTTAGTTTGACGGTACCATACCAGAAAGGGACGGCTAAATACGTGCCAG

CAGCCGCGGTAATACGTATGTCCCGAGCGTTATCCGGATTTATTGGGCGTAAAGCGAGCGCAGACGGTTTATTAA

GTCTGATGTGAAAGCCCGGAGCTCAACTCCGGAATGGCATTGGAAACTGGTTAACTTGAGTGCAGTAGAGGTAAG

TGGAACTCCATGTGTAGCGGTGGAATGCGTAGATATATGGAAGAACACCAGTGGCGAAGGCGGCTTACTGGACTG

CAACTGACGTTGAGGCTCGAAAGTGTGGGTAGCAAACAGGATTAGATACCCTGGTAGTCCACACCGTAAACGATG

AACACTAGGTGTTAGGAGGTTTCCGCCTCTTAGTGCCGAAGCTAACGCATTAAGTGTTCCGCCTGGGGAGTACGA

CCGCAAGGTTGAAACTCAAAGGAATTGACGGGACCCGCACAAGCGGTGGAGCATGTGGTTTAATTCGAAGCAAC

GCGAAGAACCTTACCAGGTCTTGACATCCTTTGAAGCTTTTAGAGATAGAAGTGTTCTCTTCGGAGACAAAGTGA

CAGGTGGTGCATGGTCGTCGTCAGCTCGTGTCGTGAGATGTTGGGTTAAGTCCCGCAACGAGCGCAACCCTTATT

GTTAGTTGCCAGCATTCAGATGGGCACTCTAGCGAGACTGCCGGTGACAAACCGGAGGAAGGCGGGGACGACGTC

AGATCATCATGCCCCTTATGACCTGGGCTACACACGTGCTACAATGGCGTATACAACGAGTTGCCAGCCCGCGAG

GGTGAGCTAATCTCTTAAAGTACGTCTCAGTTCGGATTGTAGTCTGCAACTCGACTACATGAAGTCGGAATCGCT

AGTAATCGCGGATCAGCACGCCGCGGTGAATACGTTCCCGGGTCTTGTACACACCGCCCGTCACACCATGGGAGT

TTGTAATGCCCAAAGCCGGTGGCCTAACCTTTTAGGAAGGAGCCGTCTAAGGCAGGACAGATGACTGGGGTGAAG

TCGTAACAAGGTAGCCGTAGGAGAACCTGCGGCTGGATCACCTCCTTT

Strain 2 - 16S ribosomal DNA (SEQ ID NO: 21) - *Gluconobacter oxydans*
CTGAGAGTTTGATCCTGGCTCAGAGCGAACGCTGGCGGCATGCTTAACACATGCAAGTCGCACGAAGGTTTCGGC

CTTAGTGGCGGACGGGTGAGTAACGCGTAGGGATCTATCCACGGGTGGGGGACAACTTCGGGAAACTGGAGCTAA

TACCGCATGATACCTGAGGGTCAAAGGCGCAAGTCGCCTGTGGAGGAACCTGCGTTCGATTAGCTAGTTGGTGGG

GTAAAGGCCTACCAAGGCGATGATCGATAGCTGGTTTGAGAGGATGATCAGCCACACTGGGACTGAGACACGGCC

-continued

```
CAGACTCCTACGGGAGGCAGCAGTGGGGAATATTGGACAATGGGCGAAAGCCTGATCCAGCAATGCCGCGTGTGT

GAAGAAGGTCTTCGGATTGTAAAGCACTTTCGACGGGGACGATGATGACGGTACCCGTAGAAGAAGCCCCGGCTA

ACTTCGTGCCAGCAGCCGCGGTAATACGAAGGGGGCTAGCGTTGCTCGGAATGACTGGGCGTAAAGGGCGCGTAG

GCGGTTGTTACAGTCAGATGTGAAATCCCCGGGCTTAACCTGGGAACTGCATTTGATACGTGACGACTAGAGTTC

GAGAGAGGGTTGTGGAATTCCCAGTGTAGAGGTGAAATTCGTAGATATTGGGAAGAACACCGGTGGCGAAGGCGG

CAACCTGGCTCGATACTGACGCTGAGGCGCGAAAGCGTGGGGAGCAAACAGGATTAGATACCCTGGTAGTCCACG

CTGTAAACGATGTGTGCTGGATGTTGGGAACTTAGTTTTTCAGTGTCGAAGCTAACGCGCTAAGCACACCGCCT

GGGGAGTACGGCCGCAAGGTTGAAACTCAAAGGAATTGACGGGGGCCCGCACAAGCGGTGGAGCATGTGGTTTAA

TTCGAAGCAACGCGCAGAACCTTACCAGGGCTTGCATGGGGAGGACCGGTTCAGAGATGGACCTTTCTTCGGACC

TCCCGCACAGGTGCTGCATGGCTGTCGTCAGCTCGTGTCGTGAGATGTTGGGTTAAGTCCCGCAACGAGCGCAAC

CCTTGTCTTTAGTTGCCAGCACTTTCAGGTGGGCACTCTAGAGAGACTGCCGGTGACAAGCCGGAGGAAGGTGGG

GATGACGTCAAGTCCTCATGGCCCTTATGTCCTGGGCTACACACGTGCTACAATGGCGGTGACAGTGGGAAGCTA

CATGGTGACATGGTGCTGATCTCTAAAAGCCGTCTCAGTTCGGATTGTACTCTGCAACTCGAGTACATGAAGGTG

GAATCGCTAGTAATCGCGGATCAGCATGCCGCGGTGAATACGTTCCCGGGCCTTGTACACACCGCCCGTCACACC

ATGGGAGTTGGTTCGACCTTAAGCCGGTGAGCGAACCGTAAGGACGCAGCCGACCACGGACGGGTCAGCGACTGG

GGTGAAGTCGTAACAAGGTAGCCGTAGGGGAACCTGCGGCTGGATCACCTCCTTT
```

Strain 6 - 16S ribosomal DNA (SEQ ID NO: 22) - Lactobacillus parakefiri
```
ATGAGAGTTTGATCCTGGCTCAGGACGAACGCTGGCGGCGTGCCTAATACATGCAAGTCGAACGCGTCTTGGTCA

ATGATTTTAGGTGCTTGCACTTGACTGATTTGACATTGAGACGAGTGGCGAACTGGTGAGTAACACGTGGGTAAC

CTGCCCTTGAAGTAGAGGATAACACTTGGAAACAGGTGCTAATACTGCATAACAACGAAAACCGCCTGGTTTTCG

TTTGAAAGATGGCTTCGGCTATCGCTTTAGGATGGACCCGCGGCGTATTAGCTAGTTGGTGAGGTAACGGCTCAC

CAAGGCAATGATACGTAGCCGACCTGAGAGGGTAATCGGCCACATTGGGACTGAGACACGGCCCAAACTCCTACG

GGAGGCAGCAGTAGGGAATCTTCCACAATGGACGAAAGTCTGATGGAGCAACGCCGCGTGAGTGATGAAGGGTTT

CGGCTCGTAAAACTCTGTTGTTGGAGAAGAACGGGTGTCAGAGTAACTGTTGACATCGTGACGGTATCCAACCAG

AAAGCCACGGCTAACTACGTGCCAGCAGCCGCGGTAATACGTAGGTGGCAAGCGTTGTCCGGATTTATTGGGCGT

AAAGCGAGCGCAGGCGGTTTTTTAGGTCTGATGTGAAAGCCTTCGGCTTAACCGAGAAGTGCATCGGAAACCGG

GAGACTTGAGTGCAGAAGAGGACAGTGGAACTCCATGTGTAGCGGTGAAATGCGTAGATATATGGAAGAACACCA

GTGGCGAAGGCGGCTGTCTGGTCTGCAACTGACGCTGAGGCTCGAAAGCATGGGTAGCGAACAGGATTAGATACC

CTGGTAGTCCATGCCGTAAACGATGAGTGCTAAGTGTTGGAGGGTTTCCGCCCTTCAGTGCTGCAGCTAACGCAT

TAAGCACTCCGCCTGGGGAGTACGACCGCAAGGTTGAAACTCAAAGGAATTGACGGGGGCCCGCACAAGCGGTGG

AGCATGTGGTTTAATTCGATGCTACGCGAAGAACCTTACCAGGTCTTGACATCTTCTGCCAACCTAAGAGATTAG

GCGTTCCCTTCGGGGACAGAATGACAGGTGGTGCATGGTTGTCGTCAGCTCGTGTCGTGAGATGTTGGGTTAAGT

CCCGCAACGAGCGCAACCCTTATTGTTAGTTGCCAGCATTTAGTTGGGCACTCTAGCAAGACTGCCGGTGACAAA

CCGGAGGAAGGTGGGGATGACGTCAAATCATCATGCCCCTTATGACCTGGGCTACACACGTGCTACAATGGACGG

TACAACGAGTCGCGAAACCGCGAGGTCAAGCTAATCTCTTAAAGCCGTTCTCAGTTCGGATTGTAGGCTGCAACT

CGCCTACATGAAGTTGGAATCGCTAGTAATCGTGGATCAGCATGCCACGGTGAATACGTTCCCGGGCCTTGTACA

CACCGCCCGTCACACCATGAGAGTTTGTAACACCCAAAGCCGGTGAGGTAACCTTCGGGGGCCAGCCGTCTAAGG

TGGGACAGATGATTAGGGTGAAGTCGTAACAAGGTAGCCGTAGGAGAACCTGCGGCTGGATCACCTCCTT
```

Strain 4 - 16S ribosomal DNA (SEQ ID NO: 23) - Lactobacillus brevis
```
ATGAGAGTTTGATCCTGGCTCAGGACGAACGCTGGCGGCATGCCTAATACATGCAAGTCGAACGAGCTTCCGTTG

AATGACGTGCTTGCACTGATTTCAACAATGAAGCGAGTGGCGAACTGGTGAGTAACACGTGGGGAATCTACCCAG

AAGCAGGGGATAACACTTGGAAACAGGTGCTAATACCGTATAACAACAAAATCCGCATGGATTTTGTTTGAAAGG
```

```
TGGCTTCGGCTATCACTTCTGGATGATCCCGCGGCGTATTAGTTAGTTGGTGAGGTAAAGGCCCACCAAGACGAT

GATACGTAGCCGACCTGAGAGGGTAATCGGCCACATTGGGACTGAGACACGGCCCAAACTCCTACGGGAGGCAGC

AGTAGGGAATCTTCCACAATGGACGAAAGTCTGATGGAGCAATGCCGCGTGAGTGAAGAAGGGTTTCGGCTCGTA

AAACTCTGTTGTTAAAGAAGAACACCTTTGAGAGTAACTGTTCAAGGGTTGACGGTATTTAACCAGAAAGCCACG

GCTAACTACGTGCCAGCAGCCGCGGTAATACGTAGGTGGCAAGCGTTGTCCGGATTTATTGGGCGTAAAGCGAGC

GCAGGCGGTTTTTTAAGTCTGATGTGAAAGCCTTCGGCTTAACCGGAGAAGTGCATCGGAAACTGGGAGACTTGA

GTGCAGAAGAGGACAGTGGAACTCCATGTGTAGCGGTGGAATGCGTAGATATATGGAAGAACACCAGTGGCGAAG

GCGGCTGTCTAGTCTGTAACTGACGCTGAGGCTCGAAAGCATGGGTAGCAAACAGGATTAGATACCCTGGTAGTC

CATGCCGTAAACGATGAGTGCTAAGTGTTGGAGGGTTTCCGCCCTTCAGTGCTGCAGCTAACGCATTAAGCACTC

CGCCTGGGGAGTACGACCGCAAGGTTGAAACTCAAAGGAATTGACGGGGGCCCGCACAAGCGGTGGAGCATGTGG

TTTAATTCGAAGCTACGCGAAGAACCTTACCAGGTCTTGACATCTTCTGCCAATCTTAGAGATAAGACGTTCCCT

TCGGGGACAGAATGACAGGTGGTGCATGGTTGTCGTCAGCTCGTGTCGTGAGATGTTGGGTTAAGTCCCGCAACG

AGCGCAACCCTTATTATCAGTTGCCAGCATTCAGTTGGGCACTCTGGTGAGACTGCCGGTGACAAACCGGAGGAA

GGTGGGGATGACGTCAAATCATCATGCCCCTTATGACCTGGGCTACACACGTGCTACAATGGACGGTACAACGAG

TCGCGAAGTCGTGAGGCTAAGCTAATCTCTTAAAGCCGTTCTCAGTTCGGATTGTAGGCTGCAACTCGCCTACAT

GAAGTTGGAATCGCTAGTAATCGCGGATCAGCATGCCGCGGTGAATACGTTCCCGGGCCTTGTACACACCGCCCG

TCACACCATGAGAGTTTGTAACACCCAAAGCCGGTGAGATAACCTTCGGGAGTCAGCCGTCTAAGGTGGGACAGA

TGATTAGGGTGAAGTCGTAACAAGGTAGCCGTAGGAGAACCTGCGGCTGGATCACCTCCTT

Strain 7 - 16S ribosomal DNA (SEQ ID NO: 24) - Lactobacillus plantarum
TTTGAGAGTTTGATCCTGGCTCAGGACGAACGCTGGCGGCGTGCCTAATACATGCAAGTCGAACGAACTCTGGTA

TTGATTGGTGCTTGCATCATGATTTACATTTGAGTGAGTGGCGAACTGGTGAGTAACACGTGGGAAACCTGCCCA

GAAGCGGGGGATAACACCTGGAAACAGATGCTAATACCGCATAACAACTTGGACCGCATGGTCCGAGCTTGAAAG

ATGGCTTCAGCTATCACTTTTGGATGGTCCCGCGGCGTATTAGCTAGATGGTGGGGTAACGGCTCACCATGGCAA

TGATACGTAGCCGACCTGAGAGGGTAATCGGCCACATTGGGACTGAGACACGGCCCAAACTCCTACGGGAGGCAG

CAGTAGGGAATCTTCCACAATGGACGAAAGTCTGATGGAGCAACGCCGCGTGAGTGAAGAAGGGTTTCGGCTCGT

AAAACTCTGTTGTTAAAGAAGAACATATCTGAGAGTAACTGTTCAGGTATTGACGGTATTTAACCAGAPAGCCAC

GGCTAACTACGTGCCAGCAGCCGCGGTAATACGTAGGTGGCAAGCGTTGTCCGGATTTATTGGGCGTAAAGCGAG

CGCAGGCGGTTTTTTAAGTCTGATGTGAAAGCCTTCGGCTCAACCGAAGAAGTGCATCGGAAACTGGGAAACTTG

AGTGCAGAAGAGGACAGTGGAACTCCATGTGTAGCGGTGAAATGCGTAGATATATGGAAGAACACCAGTGGCGAA

GGCGGCTGTCTGGTCTGTAACTGACGCTGAGGCTCGAAAGTATGGGTAGCAAACAGGATTAGATACCCTGGTAGT

CCATACCGTAAACGATGAATGCTAAGTGTTGGAGGGTTTCCGCCCTTCAGTGCTGCAGCTAACGCATTAAGCATT

CCGCCTGGGGAGTACGGCCGCAAGGCTGAAACTCAAAGGAATTGACGGGGGCCCGCACAAGCGGTGGAGCATGTG

GTTTAATTCGAAGCTACGCGAAGAACCTTACCAGGTCTTGACATACTATGCAAATCTAAGAGATTAGACGTTCCC

TTCGGGGACATGGATACAGGTGGTGCATGGTTGTCGTCAGCTCGTGTCGTGAGATGTTGGGTTAAGTCCCGCAAC

GAGCGCAACCCTTATTATCAGTTGCCAGCATTAAGTTGGGCACTCTGGTGAGACTGCCGGTGACAAACCGGAGGA

AGGTGGGGATGACGTCAAATCATCATGCCCCTTATGACCTGGGCTACACACGTGCTACAATGGATGGTACAACGA

GTTGCGAACTCGCGAGAGTAAGCTAATCTCTTAAAGCCATTCTCAGTTCGGATTGTAGGCTGCAACTCGCCTACA

TGAAGTCGGAATCGCTAGTAATCGCGGATCAGCATGCCGCGGTGAATACGTTCCCGGGCCTTGTACACACCGCCC

GTCACACCATGAGAGTTTGTAACACCCAAAGTCGGTGGGGTAACCTTTTAGGAACCAGCCGCCTAAGGTGGGACA

GATGATTAGGGTGAAGTCGTAACAAGGTAGCCGTAGGAGAACCTGCGGCTGGATCACCTCCTT
```

It should be appreciated that the compositions may include multiple strains of a particular species. For example, as shown in Table 2, several of the microbial communities contain more than one strains having the same or highly related 16S rDNA sequences. In some embodiments, the composition includes multiple strains of a particular species that are obtained from independent sources but the strains have the same or highly related 16S rDNA sequences.

Aspects of the disclosure relate to microbial strains with 16S rDNA sequences that have sequence identity to a nucleic acid sequence of any one of the sequences of the microbial strains or microbial species described herein. The terms "identical," or percent "identity," in the context of two or more nucleic acids or amino acid sequences, refer to two or more sequences or subsequences that are the same. Two sequences are "substantially identical" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% sequence identity) over a specified region of a nucleic acid or amino acid sequence or over the entire sequence, when compared and aligned for maximum correspondence over a comparison window, or designated region as measured using one of the following sequence comparison algorithms or by manual alignment and visual inspection. Optionally, the identity exists over a region that is at least about 50 nucleotides in length, or more preferably over a region that is 100 to 500 or 1000 or more nucleotides in length. In some embodiments, the recited degree of identity exists over the length of the 16S rRNA or 16S rDNA sequence.

In some embodiments, the microbial strain has at least 60%, at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or up to 100% sequence identity relative to any of the microbial strains or microbial species described herein over a specified region (such as a region of the 16S rDNA sequences provided herein) or over the entire sequence (such as the entire 16S rDNA). It would be appreciated by one of skill in the art that the term "sequence identity" or "percent sequence identity," in the context of two or more nucleic acid sequences or amino acid sequences, refers to a measure of similarity between two or more sequences or portion(s) thereof. In some embodiments, the identity exists over the length of the 16S rRNA or 16S rDNA sequence.

Additionally, or alternatively, two or more sequences may be assessed for the alignment between the sequences. An alignment of 100% or "total alignment" referring to two or more nucleic acids or amino acid sequences, refers to two or more sequences or subsequences that are the same. Two sequences are "substantially aligned" if two sequences have less than 100% alignment, such as a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% identical) over a specified region or over the entire sequence, when compared and aligned for maximum correspondence over a comparison window, or designated region as measured using one of the following sequence comparison algorithms or by manual alignment and visual inspection. Optionally, the alignment exists over a region that is at least about 50 nucleotides in length, or more preferably over a region that is 100 to 500 or 1000 or more nucleotides in length.

For sequence comparison, typically one sequence acts as a reference sequence, to which test sequences are compared. Methods of alignment of sequences for comparison, including measuring identity between sequences, are well known in the art. See, e.g., by the local homology algorithm of Smith and Waterman (1970) *Adv. Appl. Math.* 2:482c, by the homology alignment algorithm of Needleman and Wunsch, *J. Mol. Biol.* (1970) 48:443, by the search for similarity method of Pearson and Lipman. *Proc. Natl. Acad. Sci. USA* (1988) 85:2444, by computerized implementations of these algorithms (GAP, BESTFIT, FASTA, and TFASTA in the Wisconsin Genetics Software Package, Genetics Computer Group. Madison. Wis.), or by manual alignment and visual inspection (see. e.g., Brent et al., *Current Protocols in Molecular Biology*, John Wiley & Sons, Inc. (Ringbou ed., 2003)). Two examples of algorithms that are suitable for determining percent sequence identity and sequence similarity are the BLAST and BLAST 2.0 algorithms, which are described in Altschul et al., *Nuc. Acids Res*. (1977) 25:3389-3402; and Altschul et al., *J. Mol. Biol.* (1990) 215:403-410, respectively.

In some aspects, the present disclosure provides symbiotic microbial communities comprising at least one microbial strain belonging to the genus *Gluconobacter* or *Acetobacter* and at least one microbial strain belonging to the genus *Lactobacillus*. The combination of at least one microbial strain belonging to the genus *Gluconobacter* or *Acetobacter* and at least one microbial strain belonging to the genus *Lactobacillus* were unexpectedly found to be symbiotic/synergistic when present together in a microbial community and also produce fermented products characterized as particularly "fruity" and pleasing in sensory panels.

In some embodiments, the symbiotic microbial communities of the present disclosure comprise at least one microbial strain belonging to the genus *Gluconobacter* or *Acetobacter* and at least one microbial strain belonging to the genus *Lactobacillus*, and at least two, at least three, at least four, at least five, at least six, at least seven, at least eight, at least nine, at least ten or more additional microbial strains.

In some embodiments, the symbiotic microbial communities of the present disclosure consist of at least one microbial strain belonging to the genus *Gluconobacter* or *Acetobacter* and at least one microbial strain belonging to the genus *Lactobacillus* and at least two, at least three, at least four, at least five, at least six, at least seven, at least eight, at least nine, at least ten or more additional microbial strains.

Any of the symbiotic microbial communities described herein may further comprise one or more additional microbial strain, such as a microbial strain belonging to the genus *Leuconostoc, Obseumbacterium, Hafnia, Lactococcus, Bacillus, Lactobacillus, Acetobacter, Pediococcus,* or *Gluconobacter*. In some embodiments, the symbiotic microbial communities of the present disclosure comprise at least one microbial strain belonging to the genus *Gluconobacter* or *Acetobacter* and at least one microbial strain belonging to the genus *Lactobacillus* and one or more additional microbial strain, such as a microbial strain belonging to the genus *Leuconostoc, Obseumbacterium, Hafnia, Lactococcus, Bacillus, Lactobacillus, Acetobacter, Pediococcus,* or *Gluconobacter*. In some embodiments, the symbiotic microbial communities of the present disclosure comprise at least one microbial strain belonging to the genus *Gluconobacter* or *Acetobacter* and at least one microbial strain belonging to the genus *Lactobacillus* and additional microbial strains belonging to the genus *Leuconostoc, Obseumbacterium,*

*Hafnia, Lactococcus, Bacillus, Lactobacillus, Acetobacter, Pediococcus,* or *Gluconobacter.*

Any of the symbiotic microbial communities described herein may further comprise one or more additional microbial strain, such as a microbial strain belonging to the species *Acetobacter pasteurianus, A. ghanesis, A. orientalis, A. tropicalis, Gluconobacter oxydans, G. roseus, Gluconobacter japonicus, G. frateurii, Lactobacillus senmaizukei, L. brevis, Leuconostoc mesenteroides, Lactobacillus parakefiri, L. hilgardii, L. diolivorans, L. rapi, L. kisonesis, L. buchneri, L. fuchuensis, L. plantarum, L. paraplantarum, L. fabifermentans, L. pentosus, L. graminis, L. composti, Bacillus zanthoxyli, B. qingshengii, B. aryabhattai, B. flexus, B. megaterium, Hafnia alvei, Obesumbacterium proteus, Lactococcus taiwanensis, L. lactis, Lactobacillus casei, L. paracasei, Pediococcus claussenii, P. stilesii, P. pentosaceus,* or *P. acidilactici, Gluconacetobacter liquefaciens, Lactobacillus cerevisiae, L. kefiri, L. sunkii, L. otakiensis, L. parabuchneri, Leuconostoc lactis, L. palmae, L. holzapfelii,* or *L. citreum, Lactobacillus nagelii, L. satsumensis, Acetobacter papayae, A. suratthaniensis, A. peroxydans, Gluconacetobacter takamatsuzukensis,* or *G. asukensis.*

In some embodiments, the symbiotic microbial communities of the present disclosure comprise at least one microbial strain belonging to the genus *Gluconobacter* or *Acetobacter* and at least one microbial strain belonging to the genus *Lactobacillus* and one or more additional microbial strain, such as a microbial strain belonging to the species *Acetobacter pasteurianus, A. ghanesis, A. orientalis, A. tropicalis, Gluconobacter oxydans, G. roseus, Gluconobacter japonicus, G. frateurii, Lactobacillus senmaizukei, L. brevis, Leuconostoc mesenteroides, Lactobacillus parakefiri, L. hilgardii, L. diolivorans, L. rapi, L. kisonesis, L. buchneri, L. fuchuensis, L. plantarum, L. paraplantarum, L. fabifermentans, L. pentosus, L. graminis, L. composti, Bacillus zanthoxyli, B. qingshengii, B. aryabhattai, B. flexus, B. megaterium, Hafnia alvei, Obesumbacterium proteus, Lactococcus taiwanensis, L. lactis, Lactobacillus casei, L. paracasei, Pediococcus claussenii, P. stilesii, P. pentosaceus,* or *P. acidilactici, Gluconacetobacter liquefaciens, Lactobacillus cerevisiae, Lactobacillus kefiri, L. sunkii, L. otakiensis, L. parabuchneri, Leuconostoc lactis, L. palmae, L. holzapfelii,* or *L. citreum, Lactobacillus nagelii, L. satsumensis, Acetobacter papayae, A. suratthaniensis, A. peroxydans, Gluconacetobacter takamatsuzukensis,* or *G. asukensis.*

In some embodiments, the symbiotic microbial communities of the present disclosure comprise at least one microbial strain belonging to the genus *Gluconobacter* or *Acetobacter* and at least one microbial strain belonging to the genus *Lactobacillus* and additional microbial strains belonging to the species *Acetobacter pasteurianus, A. ghanesis, A. orientalis, A. tropicalis, Gluconobacter oxydans, G. roseus, Gluconobacter japonicus, G. frateurii, Lactobacillus senmaizukei, L. brevis, Leuconostoc mesenteroides, Lactobacillus parakefiri, L. hilgardii, L. diolivorans, L. rapi, L. kisonesis, L. buchneri, Lactobacillus fuchuensis, L. plantarum, L. paraplantarum, L. fabifermentans, L. pentosus, L. graminis, L. composti, Bacillus zanthoxyli, B. qingshengii, B. aryabhattai, B. flexus, B. megaterium, Hafnia alvei, Obesumbacterium proteus, Lactococcus taiwanensis, L. lactis, Lactobacillus casei, L. paracasei, Pediococcus claussenii, P. stilesii, P. pentosaceus,* or *P. acidilactici, Gluconacetobacter liquefaciens, Lactobacillus cerevisiae, Lactobacillus kefiri, L. sunkii, L. otakiensis, L. parabuchneri, Leuconostoc lactis, L. palmae, L. holzapfelii,* or *L. citreum, Lactobacillus nagelii, L. satsumensis, Acetobacter papayae, A. suratthaniensis, A. peroxydans, Gluconacetobacter takamatsuzukensis,* or *G. asukensis.*

In some examples, the microbial community comprises *Leuconostoc mesenteroides* subsp. *suionicum, Gluconobacter oxydans, Lactobacillus parakefiri,* and *L. plantarum.* In some examples, the microbial community consists of *Leuconostoc mesenteroides* subsp. *suionicum, Gluconobacter oxydans, Lactobacillus parakefiri,* and *L. plantarum.* A microbial community containing *Leuconostoc mesenteroides* subsp. *suionicum, Gluconobacter oxydans, Lactobacillus parakefiri,* and *L. plantarum* is referred to herein as "Community 1." In some examples, the microbial community comprises *Leuconostoc mesenteroides* subsp. *suionicum, Gluconobacter oxydans, Lactobacillus parakefiri,* and *L. plantarum* and one or more additional microbial strains. In some examples, the microbial community comprises *Leuconostoc mesenteroides* subsp. *suionicum, Gluconobacter oxydans, Lactobacillus parakefiri,* and *L. plantarum* and does not contain a yeast strain.

As will be appreciated by one of ordinary skill in the art, nomenclature regarding bacterial genus and species names may be reclassified to reflect phylogenetic relationships of microorganisms. See, e.g., Zheng et al. *Inter. J. System. And Evol. Microbiol.* (2020) 70(4).

In some embodiments, the symbiotic microbial community comprises bacterial strains having a 16S rDNA sequence comprising at least 95% (e.g., 95%, 96%, 97%, 98%, 99% or higher) sequence identity to a nucleic acid sequence provided by SEQ ID NOs: 2, 5, 6, and 7. In some embodiments, the symbiotic microbial community consists of bacterial strains having a 16S rDNA sequence comprising at least 95% (e.g., 95%, 96%, 97%, 98%, 99% or higher) sequence identity to a nucleic acid sequence provided by SEQ ID NOs: 2, 5, 6, and 7. In some embodiments, the symbiotic microbial community comprises bacterial strains having a 16S rDNA sequence comprising a nucleic acid sequence provided by SEQ ID NOs: 2, 5, 6, and 7. In some embodiments, the symbiotic microbial community consists of bacterial strains having a 16S rDNA sequence comprising a nucleic acid sequence provided by SEQ ID NOs: 2, 5, 6, and 7.

In some embodiments, the symbiotic microbial community comprises bacterial strains having a 16S rDNA sequence comprising at least 95% (e.g., 95%, 96%, 97%, 98%, 99% or higher) sequence identity to a nucleic acid sequence provided by SEQ ID NOs: 21, 20, 22, and 24. In some embodiments, the symbiotic microbial community consists of bacterial strains having a 16S rDNA sequence comprising at least 95% (e.g., 95%, 96%, 97%, 98%, 99% or higher) sequence identity to a nucleic acid sequence provided by SEQ ID NOs: 21, 20, 22, and 24. In some embodiments, the symbiotic microbial community comprises bacterial strains having a 16S rDNA sequence comprising a nucleic acid sequence provided by SEQ ID NOs: 21, 20, 22, and 24. In some embodiments, the symbiotic microbial community consists of bacterial strains having a 16S rDNA sequence comprising a nucleic acid sequence provided by SEQ ID NOs: 21, 20, 22, and 24.

In some examples, the microbial community comprises *Leuconostoc mesenteroides* subsp. *suionicum, Gluconobacter oxydans,* and *Lactobacillus brevis.* In some examples, the microbial community consists of *Leuconostoc mesenteroides* subsp. *suionicum, Gluconobacter oxydans,* and *Lactobacillus brevis.* A microbial community containing *Leuconostoc mesenteroides* subsp. *suionicum, Gluconobacter oxydans,* and *Lactobacillus brevis* is referred to herein as "Community 2." In some examples, the microbial community consists of *Leuconostoc mesenteroides* subsp. *suionicum, Gluconobacter oxydans*, and *Lactobacillus brevis* and one or more additional microbial strains. In some examples, the microbial community comprises *Leuconostoc mesenteroides* subsp. *suionicum, Gluconobacter oxydans*, and *Lactobacillus brevis* and does not contain a yeast strain.

In some embodiments, the symbiotic microbial community comprises bacterial strains having a 16S rDNA sequence comprising at least 95% (e.g., 95%, 96%, 97%, 98%, 99% or higher) sequence identity to a nucleic acid sequence provided by SEQ ID NOs: 2, 4, and 5. In some embodiments, the symbiotic microbial community consists of bacterial strains having a 16S rDNA sequence comprising at least 95% (e.g., 95%, 96%, 97%, 98%, 99% or higher) sequence identity to a nucleic acid sequence provided by SEQ ID NOs: 2, 4, and 5. In some embodiments, the symbiotic microbial community comprises bacterial strains having a 16S rDNA sequence comprising a nucleic acid sequence provided by SEQ ID NOs: 2, 4, and 5. In some embodiments, the symbiotic microbial community consists of bacterial strains having a 16S rDNA sequence comprising to a nucleic acid sequence provided by SEQ ID NOs: 2, 4, and 5.

In some embodiments, the symbiotic microbial community comprises bacterial strains having a 16S rDNA sequence comprising at least 95% (e.g., 95%, 96%, 97%, 98%, 99% or higher) sequence identity to a nucleic acid sequence provided by SEQ ID NOs: 21, 23, and 20. In some embodiments, the symbiotic microbial community consists of bacterial strains having a 16S rDNA sequence comprising at least 95% (e.g., 95%, 96%, 97%, 98%, 99% or higher) sequence identity to a nucleic acid sequence provided by SEQ ID NOs: 21, 23, and 20. In some embodiments, the symbiotic microbial community comprises bacterial strains having a 16S rDNA sequence comprising a nucleic acid sequence provided by SEQ ID NOs: 21, 23, and 20. In some embodiments, the symbiotic microbial community consists of bacterial strains having a 16S rDNA sequence comprising a nucleic acid sequence provided by SEQ ID NOs: 21, 23, and 20.

In some examples, the microbial community comprises *Leuconostoc mesenteroides* subsp. *suionicum, Gluconobacter oxydans, Lactobacillus brevis*, and *Lactobacillus plantarum*. In some examples, the microbial community consists of *Leuconostoc mesenteroides* subsp. *suionicum, Gluconobacter oxydans, Lactobacillus brevis*, and *Lactobacillus plantarum*. In some examples, the microbial community consists of *Leuconostoc mesenteroides* subsp. *suionicum, Gluconobacter oxydans, Lactobacillus brevis*, and *Lactobacillus plantarum* and one or more additional microbial strains. In some examples, the microbial community comprises *Leuconostoc mesenteroides* subsp. *suionicum, Gluconobacter oxydans, Lactobacillus brevis*, and *Lactobacillus plantarum*, and does not contain a yeast strain.

In some embodiments, the symbiotic microbial community comprises bacterial strains having a 16S rDNA sequence comprising at least 95% (e.g., 95%, 96%, 97%, 98%, 99% or higher) sequence identity to a nucleic acid sequence provided by SEQ ID NOs: 2, 4, 5, and 7. In some embodiments, the symbiotic microbial community consists of bacterial strains having a 16S rDNA sequence comprising at least 95% (e.g., 95%, 96%, 97%, 98%, 99% or higher) sequence identity to a nucleic acid sequence provided by SEQ ID NOs: 2, 4, 5, and 7. In some embodiments, the symbiotic microbial community comprises bacterial strains having a 16S rDNA sequence comprising a nucleic acid sequence provided by SEQ ID NOs: 2, 4, 5, and 7. In some embodiments, the symbiotic microbial community consists of bacterial strains having a 16S rDNA sequence comprising to a nucleic acid sequence provided by SEQ ID NOs: 2, 4, 5, and 7.

In some embodiments, the symbiotic microbial community comprises bacterial strains having a 16S rDNA sequence comprising at least 95% (e.g., 95%, 96%, 97%, 98%, 99% or higher) sequence identity to a nucleic acid sequence provided by SEQ ID NOs: 21, 23, 20, and 24. In some embodiments, the symbiotic microbial community consists of bacterial strains having a 16S rDNA sequence comprising at least 95% (e.g., 95%, 96%, 97%, 98%, 99% or higher) sequence identity to a nucleic acid sequence provided by SEQ ID NOs: 21, 23, 20, and 24. In some embodiments, the symbiotic microbial community comprises bacterial strains having a 16S rDNA sequence comprising a nucleic acid sequence provided by SEQ ID NOs: 21, 23, 20, and 24. In some embodiments, the symbiotic microbial community consists of bacterial strains having a 16S rDNA sequence comprising a nucleic acid sequence provided by SEQ ID NOs: 21, 23, 20, and 24.

The microbial strains of the symbiotic microbial communities may be in a live (e.g., viable) state or in an inactivated state (e.g., killed, not viable), or in a mixture of live and inactivated states. As will be appreciated by one of ordinary skill in the art, microbial cells may be considered live or living if the cells are metabolically active, e.g., have a detectable level of metabolic activity. Being metabolically active does not require proliferation or replication of the cells. Methods of evaluating whether a microbial strain is living and is metabolically active are known in the art, for example, viability assays, detection of ATP measurements, membrane potential, respiratory activity, uptake of dyes. See, e.g., Emerson et al. *Microbiome* (2017) 5:86. In some embodiments, one or more of the microbial strains of the symbiotic microbial community are in a live state and one or more of the microbial strains of the symbiotic microbial community are in an inactivated state (e.g., killed, not viable).

In some embodiments, the microbial strains of the symbiotic microbial communities provided herein are in vegetative form, meaning the microbial cells are not actively growing and/or reproducing. In some embodiments, at least one (e.g., 1, 2, 3, 4, 5, or more) of the microbial strains of the symbiotic microbial community is in vegetative form. In some embodiments, each of the microbial strains of the symbiotic microbial community is in vegetative form. It will be appreciated that live microbial strains may be viable but may not be actively growing/replicating. For example, following utilization of the sugar source in a fermentation medium, microbial strains may slow or halt active replication due to reduced levels of available nutrients.

In some embodiments, microbial strains of the symbiotic microbial communities provided herein are living and are alive in the fermented product.

Viability can be determined by quantifying the colony forming units (CFU), for example by plating a sample of the microbial community, or fermented beverage, on a nutritive agar medium. The number of colony forming units corresponds to the number of viable microbial cells in the sample tested such as the community or fermented beverage.

The microbial strains described herein may be obtained from or derived from any source known in the art, such as from a food source or an environmental source. As used herein, the term "derived from" in the context of microbial strains derived from a particular source refers to obtaining a microbial strain from the source, which may involve isolating and/or propagating cells of a microbial strain. In some embodiments, the microbial strains are further manipulated, such as purified and/or analyzed, prior to use in the fermented beverages and methods described herein. As will be evident to one of ordinary skill in the art, reference to a microbial strain or cells of a microbial strain that is derived from a particular source encompasses progeny cells thereof.

The microbial strains of the symbiotic microbial community may be derived from a fermented food or beverage, such as cultured milk and yogurt, natto, cheese, kombucha, wine, beer, cider, miso, kimchi, sauerkraut, fermented sausage, among others.

In some embodiments, at least one microbial strain of the symbiotic microbial community may be purified. In some embodiments, at least one microbial strain of the symbiotic microbial community may be isolated. Any of the microbial strains described herein may be isolated and/or purified, for example, from a source such as a food source (e.g., a fermented food or beverage product) or an environmental source.

In some embodiments, the microbial community may be in a lyophilized form. In some embodiments, at least one microbial strain of the symbiotic microbial community is in a lyophilized form. In some embodiments, each of microbial strains of the symbiotic microbial community is in a lyophilized form. In such embodiments, the microbial community (or microbial strain thereof) may be rehydrated or suspended and/or cultured prior to use in the methods described herein. In some embodiments, the microbial community (or microbial strain thereof) in lyophilized form is used directly, for example, without rehydrating or suspension (e.g., directly added to a medium).

As used herein, the term "isolated" refers to a microbial cell or microbial strain that has been separated from one or more undesired component, such as other microbial cells or microbial strains, one or more component of a growth medium, one or more component of a food or beverage product, and/or one or more component of a sample, such as an environmental sample. In some embodiments, the microbial strains are substantially isolated from a source such that other components of the source are not detected. In some embodiments, a microbial strain is isolated or purified from a sample and then cultured (grown, propagated) under the appropriate conditions for replication. The microbial strain that is grown under appropriate conditions for replication can subsequently be isolated/purified from the culture in which it is grown.

Also within the scope of the present disclosure are isolated microbial communities. In this context, the term "isolated" refers to a microbial community that has been separated from one or more undesired component, such as other microbial cells, microbial strains, microbial communities, one or more component of a growth medium, one or more component of a food or beverage product, and/or one or more component of a sample, such as an environmental sample. In some embodiments, the microbial communities are substantially isolated from a source such that other components of the source are not detected. In some embodiments, microbial strains are individually cultured and then combined forming the microbial community. In some embodiments, the microbial strains are combined forming a microbial community, which is then cultured (grown, propagated) collectively, as a community under the appropriate conditions for replication. The microbial strain that is grown under appropriate conditions for replication can subsequently be isolated/purified from the culture in which it is grown.

The specific microbial strains selected and combined to form the microbial communities described herein have been found to have beneficial properties when present or used in combination, as compared to microbial communities that contain different combinations of microbial strains or to microbial strains alone (not in combination).

For example, the microbial communities described herein, when compared to single strains or other microbial communities, may replicate more quickly and reach a higher biomass during fermentation. In some embodiments, the microbial communities described herein replicate at a rate that is at least 1.1-fold, 1.2-fold, 1.3-fold, 1.4-fold, 1.5-fold, 2-fold, 3-fold, 4-fold, 5-fold, 6-fold, 7-fold, 8-fold, 9-fold, 10-fold, 20-fold, 30-fold, 40-fold, or up to 50-fold higher than a microbial community containing a different combination of microbial strains or the microbial strains when present or used alone under similar fermentation conditions. In some embodiments, the microbial communities described herein replicate at a rate that is about 2-3-fold higher than a microbial community containing a different combination of microbial strains or the microbial strains when present or used alone under similar fermentation conditions.

In some embodiments, the microbial communities described herein reach a biomass that is at least 1.1-fold, 1.2-fold, 1.3-fold, 1.4-fold, 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 200-fold, 300-fold, 400-fold or up to 500-fold higher than the biomass that can be reached with a microbial community containing a different combination of microbial strains or with a microbial strain alone under similar fermentation conditions. In some embodiments, the microbial communities described herein reach a biomass that is about 5-10-fold higher than the biomass that can be reached with a microbial community containing a different combination of microbial strains or with a microbial strain alone under similar fermentation conditions.

The microbial communities described herein are able to maintain a relatively stable biomass, for example in a fermented product, over time. In some embodiments, the microbial communities described herein are able to maintain a relatively stable biomass, for example in a fermented product, over time as compared to the biomass of the microbial strains when provided in the absence of the community (e.g., individually). A microbial community is considered to be stable in maintaining a biomass if there is less than 99% decrease (2-logs) in the biomass over 60 days. In some embodiments, the microbial community has a biomass (CFU/mL) that decreases by less than 10%, 20%, 30%, 40%, 50%, 60%, 70%, 80%, 90%, 95%, 96%, 97%, 98%. 99%. 99.1%, 99.2%, 99.3%, 99.4%, 99.5%, 99.6%, 99.7%, 99.8%, 99.8%, 99.9% or higher over a period of 60 days, for example stored at room temperature. In some embodiments, the microbial community has a biomass (CFU/mL) that decreases by less than 10%, 20%, 30%, 40%, 50%, 60%, 70%, 80%, 90%, 95%, 96%, 97%, 98%. 99%. 99.1%, 99.2%, 99.3%, 99.4%, 99.5%, 99.6%, 99.7%, 99.8%, 99.8%, 99.9% or higher over a period of 60 days as compared to the biomass of the fermented beverage at a prior time point (e.g., at the end of fermentation), another microbial community, or individual microbial strains.

In some embodiments, the microbial community has a biomass (CFU/mL) that decreases by less than 1,000-fold (3 logs), 100-fold (2 logs), or less than 10-fold (1 log) over a period of 60 days, for example stored at room temperature. In some embodiments, the microbial community has a biomass (CFU/mL) that decreases by less than 1,000-fold (3 logs), 100-fold (2 logs), or less than 10-fold (1 log) over a period of 60 days, for example as compared to the biomass of the fermented beverage at a prior time point (e.g., at the end of fermentation), another microbial community, or individual microbial strains.

Methods of assessing the replication rate of a microbial strain or community thereof, as well as methods of quantifying biomass, are known in the art. See, e.g. Brown et al. *Nature Biotechnology* (2016) 34: 1256-1263

As another example, the microbial communities described herein may ferment more quickly than other microbial communities or than single microbial strains used alone. The rate of fermentation of a microbial community can be assessed by any means known in the art, such as the utilization of a sugar source, level of a sugar in the fermentation medium, change in pH of the medium, generation of a fermentation product (e.g., organic acids, $CO_2$). In some embodiments, the microbial communities described herein ferment at a rate that is at least 1.1-fold, 1.2-fold, 1.3-fold, 1.4-fold, 1.5-fold, 2-fold, 3-fold, 4-fold, 5-fold, 6-fold, 7-fold, 8-fold, 9-fold, 10-fold, 20-fold, 30-fold, 40-fold, or up to 50-fold higher than a microbial community containing a different combination of microbial strains or single microbial strains when used alone under similar fermentation conditions. In some embodiments, the microbial communities described herein ferment at a rate that is about 2-3-fold higher than a microbial community containing a different combination of microbial strains or single microbial strains when used alone under similar fermentation conditions.

Contamination of fermentation reactions or products intended for consumer consumption can result in spoilage of products, lost profit and revenue for manufacturers, and represent a substantial health and safety risk to individuals who ingest contaminated products. The conditions that are critical for promoting fermentation, including availability of sugar source and other nutrients and temperatures at which fermentation is typically performed are also conditions in which other microorganisms, including pathogenic microbial strains, survive and replicate. Surprisingly, the microbial communities described herein have been found to be more "resilient" to invasion by environmental contaminants, including unwanted bacterial, yeast, and mold strains, such as *Pseudomonas* spp., *Listeria monocytogenes*, *Salmonella* spp., *Shigella flexneri*, *Escherichia coli*, *Vibrio cholerae*, *Bacillus* spp., *Campylobacter jejuni*, *Candida* spp., *Cryptococcus* spp., *Debaryomyces* spp., *Hansenula* spp., *Pichia* spp., *Rhodotorula* spp., *Saccharomyces* spp., *Torulopsis* spp., *Zygosaccharomyces* spp., *Dekkera* spp., and *Trichosporon* spp.

The ability of a microbial community to resist, prevent, or minimize invasion by a contaminant, such as unwanted bacterial, yeast, and mold strains, may result from active antimicrobial capacities (e.g., bacteriocin production) of the individual microbial strains of the community or the microbial community collectively. It should be noted that production of inhibitory compounds, such as antimicrobial molecules, by a microbial strain of the community may be stimulated by another strain(s) of the community.

In some embodiments, the combination of microbial strains in the community synergizes resulting in increased rate of fermentation and/or microbial replication, which may limit available nutrients for contaminating strains, such as unwanted bacterial, yeast, and mold strains. The capability of a microbial community (or individual microbial strains) to resist, prevent, or minimize invasion of a fermented product or the fermentation process by a contaminant may be assessed by any means known in the art, such as by competition assays.

The microbial strains used in any of the symbiotic microbial communities described herein are preferably "generally recognized as safe" (GRAS) or approved as food additives according to the U.S. Food and Drug Administration. See, e.g., Federal Food, Drug, and Cosmetic Act, sections 201(s) and 409.

Fermented Beverages

Aspects of the present disclosure relate to fermented beverages, including fermented beverages produced by any of the methods disclosed herein. The nature of the fermented beverage will depend on factors such as the fermentable sugar provided for the fermentation process, the sugar source, as well as any additional components added prior to, during, or following fermentation. The fermented beverages described herein are produced using symbiotic microbial communities that together lead to low sugar content, low alcohol content, and improved and desired characteristics in the fermented beverage, including increased levels of organic acids and/or reduced levels of acetic acid.

Non-limiting examples of fermented beverages include kombucha, water kefir, flavored water product, jun, soda, seltzer, sparkling water, gut shot, functional beverage, fermented fruit juice, fermented vegetable juice, probiotic beverages, ginger beer, and fermented sports drinks. In some embodiments, the fermented beverage is kombucha.

The fermented beverages described herein are fermented to completion, meaning the fermentation process used to produce the beverages is performed under conditions and for a time period sufficient to bring the level of one or more components below (or in some instances above) a certain level. For example, in some instances, fermented to completion means that the fermentation process is performed under conditions and for a time period sufficient to bring the sugar level in the fermented beverage product to below a threshold level. In some embodiments, fermented to completion means that the fermentation process is performed under conditions and for a time period sufficient to bring the level of alcohol (ethanol) to below a threshold level. In some instances, fermented to completion means that the fermentation process is performed under conditions and for a time period sufficient to bring the sugar level in the fermented beverage product to below a threshold level and to bring the level of alcohol (ethanol) to below a threshold level. In some embodiments, the final fermented beverage contains a level of sugar that is less than the level of sugar, for example, in a fermented beverage that is produced using other microbial communities. In some embodiments, the fermented beverage contains a level of sugar that is less than 20.0 g/L, less than 19.0 g/L, less than 18.0 g/L, less than 17.0 g/L, less than 16.0 g/L, less than 15.0 g/L, less than 14.0 g/L, less than 13.0 g/L, less than 12.0 g/L, less than 11.0 g/L, less than 10.0 g/L, less than 9.0 g/L, less than 8.0 g/L, less than 7.0 g/L, less than 6.0 g/L, less than 5.0 g/L, less than 4.0 g/L, less than 3.0 g/L, less than 2.0 g/L, less than 1.0 g/L, less than 0.9 g/L, less than 0.8 g/L, less than 0.07 g/L, less than 0.6 g/L, less than 0.5 g/L, less than 0.4 g/L, less than 0.3 g/L, less than 0.2 g/L, less than 0.1 g/L. In some embodiments, the fermented beverage contains a level of sugar that is not detectable (below the limits of detection). In some embodiments, the fermented product does not contain sugar, e.g., approximately 0 g/L.

In some embodiments, the fermented beverages described herein are considered "zero sugar" or "zero calorie" fermented beverages. According to the U.S. Food and Drug Administration, a food or beverage product must contain less than 0.5 grams sugar per serving (e.g., 8 fluid ounce serving) to be a "zero sugar" food or beverage product and less than 5 calories per serving to be a "zero calorie" food or beverage product.

In some embodiments, the fermented beverage is considered a "low sugar" fermented beverage. As used herein, the term "low sugar" refers to a level of sugar that is less than 5 grams per 8 fluid ounce serving. In some embodiments, the fermented beverages described herein contain less than 10.0 g, less than 9.0 g, 0.5 g, less than 0.4 g, less than 0.3 g, less than 0.3 g, less than 0.2 g, less than 0.1 g, less than 0.09 g, less than 0.08 g, less than 0.07 g, less than 0.06 g, less than 0.05 g, less than 0.04 g, less than 0.03 g, less than 0.02 g, less than 0.01 g, or lower per 8 fluid ounce serving (approximately 237 milliliters).

The level of sugar (sugar content) in a product, such as a fermented beverage, may be assessed using methods known in the art, for example gas chromatography or enzymatic assays.

Described herein, fermentation processes involve the conversion of carbohydrates into alcohol and carbon dioxide, and possibly the conversion of the alcohol to organic acids. By way of an example, during fermentation of kombucha using microbial communities containing yeast strains in addition to bacterial strains, the fermentation process includes two steps: conversion of sugars to alcohol by the yeast strains and subsequently conversion of alcohol to organic acids by the yeast and bacterial strains. However, during kombucha fermentation, the second step of fermentation is not complete, resulting in residual alcohol levels up to around 3% alcohol by volume (i.e., 3% of the total volume is alcohol) reported for some home-brewed kombuchas. See, e.g., brewdrkombucha.com, Blog post, Sep. 28, 2018: "Alcohol in Kombucha: What you need to know."

The level of alcohol in a fermented beverage is typically reported as alcohol by volume (also referred to as "ABV," "abv," or "alc/vol"), which is presented as a volume percent. ABV is typically used as a measure of the amount of ethanol in beverage products and is calculated as the number of milliliters of ethanol per 100 mL of beverage product at 20° C. In some embodiments, the fermented beverage contains a level of alcohol (ethanol) that is less than 3%, less than 2%, less than 1%, less than 0.9%, less than 0.8%, less than 0.7%, less than 0.6%, less than 0.5%, less than 0.4%, less than 0.3%, less than 0.2%, less than 0.1% v/v or lower. In some embodiments, the fermented beverage is non-alcoholic (e.g., has an alcohol by volume less than 0.5%).

The amount of alcohol (e.g., ethanol) in a beverage product can be measured by any means known in the art, such as using the specific gravity or an enzymatic assay. The specific gravity may be measured prior to and after a fermentation process and the change in specific gravity indicates the amount of alcohol produced during fermentation. Alternatively or in addition, enzymatic assays for alcohol (e.g., ethanol) or near infrared alcohol measurements (e.g., "Alcolyzer") may be used to determine the amount of alcohol in a beverage product.

During the fermentation process, microorganisms metabolize carbohydrates into organic acids, which may contribute to the flavor and/or aromatic profile of a fermented beverage. The presence of organic acids in the fermented product may provide desired sensory qualities, such as desired flavors, tastes, and aromas, as well as health benefits. In particular, glucuronic acid has been attributed with providing numerous health benefits, including as a precursor to the synthesis of vitamin C and as a substrate for production of glucosamine, which is used in the prophylaxis of arthritis. See, e.g., Nguyen et al. *LWT—Food Science and Technology* (2015) 64, 1149-1155; Yavari et al. *Australian Journal of Basic and Applied Sciences* (2011) 5(11), 1788-1794.

Examples of organic acids produced during fermentation include, without limitation, acetic acid, glucuronic, ketogluconic acid, gluconic acid, lactic acid, malic acid, citric acid, tartaric acid, folic acid, malonic acid, oxalic acid, succinic acid, pyruvic acid, and usnic acid. See, e.g., Neffe-Skocinska et al. *CyTA—Journal of Food* (2017) 15:4, 601-607.

Kombuchas produced using conventional methods may be characterized by relatively high levels of acetic acid, which impart an undesirable vinegar flavor. As used herein, high levels of acetic acid refer to levels of acetic acid that are about 10 g/L or higher. In some embodiments, the fermented beverages described herein contain a reduced level of acetic acid (e.g., less than about 10 g/L), for example as compared to fermented beverages produced using other microbial communities, such as microbial communities containing yeast strains. In some embodiments, the fermented beverages described herein contain less than 10 g/L acetic acid. In some embodiments, the fermented beverages described herein contain a level of acetic acid that is less than 10.0 g/L, 9.0 g/L, 8.0 g/L, 7.0 g/L, 6.0 g/L, 5.0 g/L, 4.0 g/L, 3.0 g/L, 2.0 g/L, 1.0 g/L, 0.9 g/L, 0.8 g/L, 0.7 g/L, 0.6 g/L, 0.5 g/L, 0.4 g/L, 0.3 g/L, 0.2 g/L, 0.1 g/L, 0.09 g/L, 0.08 g/L, 0.07 g/L, 0.06 g/L, 0.05 g/L, 0.04 g/L, 0.03 g/L, 0.02 g/L, 0.01 g/L or lower. In some embodiments, the fermented beverages described herein contain a level of acetic acid that is between 0.1-0.5 g/L.

In some embodiments, the fermented beverages described herein contain increased levels of organic acids that are not acetic acid, for example as compared to the level of organic acids present in fermented beverages produced using other microbial communities, such as microbial communities containing yeast strains. In some embodiments, the fermented beverages described herein contain more than 10.0 g/L organic acids that are not acetic acid. In some embodiments, the fermented beverages described herein contain more than 10.0 g/L lactic acid, gluconic acid, ketogluconic acid, or a combination thereof. In some embodiments, the fermented beverages described herein contain a level of organic acid(s) that is more than 1.0 g/L, 2.0 g/L, 3.0 g/L, 4.0 g/L, 5.0 g/L, 6.0 g/L, 7.0 g/L, 8.0 g/L, 9.0 g/L, 10.0 g/L, 11.0 g/L, 12.0 g/L, 13.0 g/L, 14.0 g/L, 15.0 g/L, 16.0 g/L, 17.0 g/L, 18.0 g/L, 19.0 g/L, 20.0 g/L, 21.0 g/L, 22.0 g/L, 23.0 g/L, 24.0 g/L, 25.0 g/L, 26.0 g/L, 27.0 g/L, 28.0 g/L, 29.0 g/L, 30.0 g/L, 31.0 g/L, 32 g/L, 33 g/L, 34 g/L, 35 g/L, 36 g/L, 37 g/L, 38 g/L, 39 g/L, or up to 40 g/L.

In some embodiments, the fermented beverages described herein contain a level of gluconic acid that is between 0.5 g/L-2.0 g/L. In some embodiments, the fermented beverages described herein contain a level of gluconic acid that is about 0.5, 0.6, 0.7, 0.8, 0.9, 1.0, 1.1, 1.2, 1.3, 1.4, 1.5, 1.6, 1.7, 1.8, 1.9, or 2.0 g/L.

In some embodiments, the fermented beverages described herein contain a level of lactic acid that is between 0.02 g/L-2.0 g/L. In some embodiments, the fermented beverages described herein contain a level of lactic acid that is about 0.2 g/L, 0.3 g/L, 0.4 g/L, 0.5 g/L, 0.6 g/L, 0.7 g/L, 0.8 g/L, 0.9 g/L, 1.0 g/L, 1.1 g/L, 1.2 g/L, 1.3 g/L, 1.4, g/L 1.5 g/L, 1.6 g/L, 1.7 g/L, 1.8 g/L, 1.9 g/L, or 2.0 g/L.

In some embodiments, the pH of the fermented beverage is acidic, i.e., less than pH 6.0. For a shelf-stable acidified beverage, the U.S. Food and Drug Administration Food Code requires that the final pH of the beverage be less than pH 4.6. In some embodiments, the pH of the fermented beverage is less than about pH 6, 5.9, 5.8, 5.7, 5.6, 5.5, 5.4, 5.3, 5.2, 5.1, 5.0, 4.9, 4.8, 4.7, 4.6, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0 or lower. In some embodiments, the pH of the fermented beverage is less than about 4.6. In some embodiments, the pH of the fermented beverage is less than about 3.5. In some embodiments, the pH of the fermented beverage between 2.9-3.1.

As described herein, many fermented beverages, such as kombucha, must be stored and distributed using refrigerated temperatures (i.e., cold supply chain), to protect integrity of the product; and/or prevent or reduce continued fermentation, including increase in alcohol content; and/or prevent or reduce microbial overgrowth. Recommended temperatures for storing and distributing kombucha products, for example, are considered to be between 34-40° F. (1.1-4.4° C.) by Kombucha Brewers International. Maintaining refrigerated temperatures during storage and distribution is substantially more expensive relative to room temperature (ambient temperature), non-refrigerated conditions. Moreover, failure to maintain appropriately cold temperatures for the prior art kombucha products may result in an inferior fermented product, overgrowth of microbial strains including contaminants, and explosion of bottles containing the kombucha product.

In contrast, the fermented beverages described herein have increased shelf-stability. As used herein, the term "shelf-stable" refers to stability and product integrity when a product is maintained at ambient temperatures (about 20°-22° C.) for an extended period of time. In some embodiments, the fermented beverage is stable at ambient temperature (i.e., between about 20°-22° C.) for at least or about 1 week, at least or about 2 weeks, at least or about 3 weeks, at least or about 4 weeks, at least or about 5 weeks, at least or about 6 weeks, at least or about 7 weeks, at least or about 8 weeks, at least or about one month, at least or about two months, at least or about three months, at least or about four months, at least or about five months, at least or about six months, at least or about seven months, at least or about eight months, at least or about nine months, at least or about ten months, at least or about eleven months, at least or about twelve months, at least or about one year, at least or about two years, at least or about three years, at least or about four years, at least or about five years, or longer.

In some embodiments, the fermented beverages described herein may also have increased stability or product integrity at an elevated temperature, e.g., above about 23° C. In some embodiments, the fermented beverages described herein have increased stability or product integrity at a temperature higher than or about 23° C., higher than or about 24° C., higher than or about 25° C., higher than or about 26° C., higher than or about 27° C., higher than or about 28° C., about 29° C., higher than or about 30° C., higher than or about 31° C., higher than or about 32° C., higher than or about 33° C., higher than or about 34° C., higher than or about 35° C., higher than or about 36° C., higher than or about 37° C., higher than or about 38° C., higher than or about 39° C., higher than or about 40° C. or higher.

In some embodiments, the fermented beverage is stable at an elevated temperature, e.g., above or about 23° C., for at least or about 1 week, at least or about 2 weeks, at least or about 3 weeks, at least or about 4 weeks, at least or about 5 weeks, at least or about 6 weeks, at least or about 7 weeks, at least or about 8 weeks, at least or about one month, at least or about two months, at least or about three months, at least or about four months, at least or about five months, at least or about six months, at least or about seven months, at least or about eight months, at least or about nine months, at least or about ten months, at least or about eleven months, at least or about twelve months, at least or about one year, at least or about two years, at least or about three years, at least or about four years, at least or about five years, or longer.

Determining whether a fermented beverage is stable or the product integrity is intact will be evident to one of ordinary skill in the art, and may involve using methods known in the art. For example, in some embodiments, the stability of the fermented beverage under particular conditions involves evaluating, for example, flavor profile, color profile, amounts of CFUs of microbial strains, alcohol content, pH, and/or detection of contaminants. In general, a fermented beverage is considered to be "stable" if one or more properties (e.g., CFU of the microbial strains, sugar content, alcohol content, flavor profile, pH, etc) of the beverages does not substantially change under particular conditions.

In some embodiments, a fermented product is considered shelf-stable if the number of (viable) microbial cells does not change by more than 90% over a period of at least one week, two weeks, three weeks, four weeks, five weeks, six weeks, or longer at ambient temperature. In some embodiments, a fermented product is considered shelf-stable if the pH of the fermented product does not change by more than 10% over a period of at least one week, two weeks, three weeks, four weeks, five weeks, six weeks, or longer at ambient temperature. In some embodiments, a fermented product is considered shelf-stable if the product flavor profile does not substantially or detectably change over a period of at least one week, two weeks, three weeks, four weeks, five weeks, six weeks, or longer at ambient temperature.

A fermented beverage may be considered to be stable in regard to the biomass if there is less than 99% decrease (2-logs) in the biomass in the fermented beverage over 60 days. In some embodiments, the fermented beverage has a biomass (CFU/mL) that decreases by less than 10%, 20%, 30%, 40%, 50%, 60%, 70%, 80%, 90%, 95%, 96%, 97%, 98%. 99%. 99.1%, 99.2%, 99.3%, 99.4%, 99.5%, 99.6%, 99.7%, 99.8%, 99.8%, 99.9% or higher over a period of 60 days, for example stored at room temperature. In some embodiments, the fermented beverage has a biomass (CFU/mL) that decreases by less than 10%, 20%, 30%, 40%, 50%, 60%, 70%, 80%, 90%, 95%, 96%, 97%, 98%. 99%. 99.1%, 99.2%, 99.3%, 99.4%, 99.5%, 99.6%, 99.7%, 99.8%, 99.8%, 99.9% or higher over a period of 60 days as compared to the biomass of the fermented beverage at a prior time point (e.g., at the end of fermentation), another microbial community, or individual microbial strains.

In some embodiments, the fermented beverage contains a microbial community having a biomass (CFU/mL) that decreases by less than 1,000-fold (3 logs), 100-fold (2 logs), or less than 10-fold (1 log) over a period of 60 days, for example stored at room temperature. In some embodiments, the fermented beverage contains a microbial community having a biomass (CFU/mL) that decreases by less than 1,000-fold (3 logs), 100-fold (2 logs), or less than 10-fold (1 log) over a period of 60 days, for example as compared to the biomass of the fermented beverage at a prior time point (e.g., at the end of fermentation), another microbial community, or individual microbial strains.

In some embodiments, the fermented beverages comprise about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more of each of the microbial strains per 8 fluid ounce serving (approximately 237 mL). In some embodiments, the fermented beverages comprise at least or about 10, at least or about $10^2$, at least or about $10^3$, at least or about $10^4$, at least or about $10^5$, at least or about $10^6$, at least or about $10^7$, at least or about $10^8$, at least or about $10^9$, at least or about $10^{10}$, at least or about $10^{11}$, at least or about $10^{12}$, at least or about $10^{13}$ or more of each of the microbial strains per 8 fluid ounce serving (approximately 237 mL).

In some embodiments, the fermented beverages comprise about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more of each of the microbial strains per milliliter of fermented beverage. In some embodiments, the fermented beverages comprise at least or about 10, at least or about $10^2$, at least or about $10^3$, at least or about $10^4$, at least or about $10^5$, at least or about $10^6$, at least or about $10^7$, at least or about $10^8$, at least or about $10^9$, at least or about $10^{10}$, at least or about $10^{11}$, at least or about $10^{12}$, at least or about $10^{13}$ or more of each of the microbial strains per milliliter of fermented beverage.

In some embodiments, the fermented beverage contains between about 10 and about $10^{13}$, between about $10^2$ and about $10^{13}$, between about $10^3$ and about $10^{13}$, between about $10^4$ and about $10^{13}$, between about $10^5$ and about $10^{13}$, between about $10^6$ and about $10^{13}$, between about $10^7$ and about $10^{13}$, between about $10^8$ and about $10^{13}$, between about $10^9$ and about $10^{13}$, between about $10^{10}$ and about $10^{13}$, between about $10^{11}$ and about $10^{13}$, between about $10^{12}$ and about $10^{13}$, between about 10 and about $10^{12}$, between about $10^2$ and about $10^{12}$, between about $10^3$ and about $10^{12}$, between about $10^4$ and about $10^{12}$, between about $10^5$ and about $10^{12}$, between about $10^6$ and about $10^{12}$, between about $10^7$ and about $10^{12}$, between about $10^8$ and about $10^{12}$, between about $10^9$ and about $10^{12}$, between about $10^{10}$ and about $10^{12}$, between about $10^{11}$ and about $10^{12}$, between about 10 and about $10^{11}$, between about $10^2$ and about $10^{11}$, between about $10^3$ and about $10^{13}$, between about $10^4$ and about $10^{13}$, between about $10^5$ and about $10^{13}$, between about $10^6$ and about $10^{13}$, between about $10^7$ and about $10^{11}$, between about $10^8$ and about $10^{11}$, between about $10^9$ and about $10^{11}$, between about $10^{10}$ and about $10^{11}$, between about 10 and about $10^{10}$, between about $10^2$ and about $10^{10}$, between about $10^3$ and about $10^{10}$, between about $10^4$ and about $10^{10}$, between about $10^5$ and about $10^{10}$, between about $10^6$ and about $10^{10}$, between about $10^7$ and about $10^{10}$, between about $10^8$ and about $10^{10}$, between about $10^9$ and about $10^{10}$, between about 10 and about $10^9$, between about $10^2$ and about $10^9$, between about $10^3$ and about $10^9$, between about $10^4$ and about $10^9$, between about $10^5$ and about $10^9$, between about $10^6$ and about $10^9$, between about $10^7$ and about $10^9$, between about $10^8$ and about $10^9$, between about 10 and about $10^8$, between about $10^2$ and about $10^8$, between about $10^3$ and about $10^8$, between about $10^4$ and about $10^8$, between about $10^5$ and about $10^8$, between about $10^6$ and about $10^8$, between about $10^7$ and about $10^8$, between about 10 and about $10^7$, between about $10^2$ and about $10^7$, between about $10^3$ and about $10^7$, between about $10^4$ and about $10^7$, between about $10^5$ and about $10^7$, between about $10^6$ and about $10^7$, between about 10 and about $10^6$, between about $10^2$ and about $10^6$, between about $10^3$ and about $10^6$, between about $10^4$ and about $10^6$, between about $10^5$ and about $10^6$, between about 10 and about $10^5$, between about $10^2$ and about $10^5$, between about $10^3$ and about $10^5$, between about $10^4$ and about $10^5$, between about 10 and about $10^4$, between about $10^2$ and about $10^4$, between about $10^3$ and about $10^4$, between about 10 and about $10^3$, between about $10^2$ and about $10^3$, or between about 10 and about $10^2$ of each of the microbial strains per 8 fluid ounce serving. In some embodiments, the fermented beverage contains between $10^7$ and $10^9$ of each of the microbial strains per 8 fluid ounce serving. Each of the microbial strains of the symbiotic microbial community may be present in the same amount or in different amounts.

In some embodiments, the fermented beverage contains between about 10 and about $10^{13}$, between about $10^2$ and about $10^{13}$, between about $10^3$ and about $10^{13}$, between about $10^4$ and about $10^{13}$, between about $10^5$ and about $10^{13}$, between about $10^6$ and about $10^{13}$, between about $10^7$ and about $10^{13}$, between about $10^8$ and about $10^{13}$, between about $10^9$ and about $10^{13}$, between about $10^{10}$ and about $10^{13}$, between about $10^{11}$ and about $10^{13}$, between about $10^{12}$ and about $10^{13}$, between about 10 and about $10^{12}$, between about $10^2$ and about $10^{12}$, between about $10^3$ and about $10^{12}$, between about $10^4$ and about $10^{12}$, between about $10^5$ and about $10^{12}$, between about $10^6$ and about $10^{12}$, between about $10^7$ and about $10^{12}$, between about $10^8$ and about $10^{12}$, between about $10^9$ and about $10^{12}$, between about $10^{10}$ and about $10^{12}$, between about $10^{11}$ and about $10^{12}$, between about 10 and about $10^{11}$, between about $10^2$ and about $10^{11}$, between about $10^3$ and about $10^{13}$, between about $10^4$ and about $10^{13}$, between about $10^5$ and about $10^{13}$, between about $10^6$ and about $10^{13}$, between about $10^7$ and about $10^{11}$, between about $10^8$ and about $10^{11}$, between about $10^9$ and about $10^{11}$, between about $10^{10}$ and about $10^{11}$, between about 10 and about $10^{10}$, between about $10^2$ and about $10^{10}$, between about $10^3$ and about $10^{10}$, between about $10^4$ and about $10^{10}$, between about $10^5$ and about $10^{10}$, between about $10^6$ and about $10^{10}$, between about $10^7$ and about $10^{10}$, between about $10^8$ and about $10^{10}$, between about $10^9$ and about $10^{10}$, between about 10 and about $10^9$, between about $10^2$ and about $10^9$, between about $10^3$ and about $10^9$, between about $10^4$ and about $10^9$, between about $10^5$ and about $10^9$, between about $10^6$ and about $10^9$, between about $10^7$ and about $10^9$, between about $10^8$ and about $10^9$, between about 10 and about $10^8$, between about $10^2$ and about $10^8$, between about $10^3$ and about $10^8$, between about $10^4$ and about $10^8$, between about $10^5$ and about $10^8$, between about $10^6$ and about $10^8$, between about $10^7$ and about $10^8$, between about 10 and about $10^7$, between about $10^2$ and about $10^7$, between about $10^3$ and about $10^7$, between about $10^4$ and about $10^7$, between about $10^5$ and about $10^7$, between about $10^6$ and about $10^7$, between about 10 and about $10^6$, between about $10^2$ and about $10^6$, between about $10^3$ and about $10^6$, between about $10^4$ and about $10^6$, between about $10^5$ and about $10^6$, between about 10 and about $10^5$, between about $10^2$ and about $10^5$, between about $10^3$ and about $10^5$, between about $10^4$ and about $10^5$, between about 10 and about $10^4$, between about $10^2$ and about $10^4$, between about $10^3$ and about $10^4$, between about 10 and about $10^3$, between about $10^2$ and about $10^3$, or between about 10 and about $10^2$ of each of the microbial strains per milliliter of fermented beverage. In some embodiments, the fermented beverage contains between $10^5$ and $10^6$ of each of the microbial strains per milliliter of fermented beverage. Each of the microbial strains of the symbiotic microbial community may be present in the same amount or in different amounts.

In some embodiments, the fermented beverages comprise about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more total microbial cells (CFU) of all microbial strains per 8 fluid ounce serving (approximately 237 mL). In some embodiments, the fermented beverages comprise at least 10, at least $10^2$, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$ or more of total microbial cells (CFU) of all microbial strains per 8 fluid ounce serving (approximately 237 mL)).

In some embodiments, the fermented beverages comprise about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more total microbial cells (CFU) of all microbial strains per milliliter fermented beverage. In some embodiments, the fermented beverages comprise at least 10, at least $10^2$, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$ or more of total microbial cells (CFU) of all microbial strains per milliliter fermented beverage.

In some embodiments, the fermented beverage contains between about 10 and about $10^{13}$, between about $10^2$ and about $10^{13}$, between about $10^3$ and about $10^{13}$, between about $10^4$ and about $10^{13}$, between about $10^5$ and about $10^{13}$, between about $10^6$ and about $10^{13}$, between about $10^7$ and about $10^{13}$, between about $10^8$ and about $10^{13}$, between about $10^9$ and about $10^{13}$, between about $10^{10}$ and about $10^{13}$, between about $10^{11}$ and about $10^{13}$, between about $10^{12}$ and about $10^{13}$, between about 10 and about $10^{12}$, between about $10^2$ and about $10^{12}$, between about $10^3$ and about $10^{12}$, between about $10^4$ and about $10^{12}$, between about $10^5$ and about $10^{12}$, between about $10^6$ and about $10^{12}$, between about $10^7$ and about $10^{12}$, between about $10^8$ and about $10^{12}$, between about $10^9$ and about $10^{12}$, between about $10^{10}$ and about $10^{12}$, between about $10^{11}$ and about $10^{12}$, between about 10 and about $10^{11}$, between about $10^2$ and about $10^{11}$, between about $10^3$ and about $10^{13}$, between about $10^4$ and about $10^{13}$, between about $10^5$ and about $10^{13}$, between about $10^6$ and about $10^{13}$, between about $10^7$ and about $10^{11}$, between about $10^8$ and about $10^{11}$, between about $10^9$ and about $10^{11}$, between about $10^{10}$ and about $10^{11}$, between about 10 and about $10^{10}$, between about $10^2$ and about $10^{10}$, between about $10^3$ and about $10^{10}$, between about $10^4$ and about $10^{10}$, between about $10^5$ and about $10^{10}$, between about $10^6$ and about $10^{10}$, between about $10^7$ and about $10^{10}$, between about $10^8$ and about $10^{10}$, between about $10^9$ and about $10^{10}$, between about 10 and about $10^9$, between about $10^2$ and about $10^9$, between about $10^3$ and about $10^9$, between about $10^4$ and about $10^9$, between about $10^5$ and about $10^9$, between about $10^6$ and about $10^9$, between about $10^7$ and about $10^9$, between about $10^8$ and about $10^9$, between about 10 and about $10^8$, between about $10^2$ and about $10^8$, between about $10^3$ and about $10^8$, between about $10^4$ and about $10^8$, between about $10^5$ and about $10^8$, between about $10^6$ and about $10^8$, between about $10^7$ and about $10^8$, between about 10 and about $10^7$, between about $10^2$ and about $10^7$, between about $10^3$ and about $10^7$, between about $10^4$ and about $10^7$, between about $10^5$ and about $10^7$, between about $10^6$ and about $10^7$, between about 10 and about $10^6$, between about $10^2$ and about $10^6$, between about $10^3$ and about $10^6$, between about $10^4$ and about $10^6$, between about $10^5$ and about $10^6$, between about 10 and about $10^5$, between about $10^2$ and about $10^5$, between about $10^3$ and about $10^5$, between about $10^4$ and about $10^5$, between about 10 and about $10^4$, between about $10^2$ and about $10^4$, between about $10^3$ and about $10^4$, between about 10 and about $10^3$, between about $10^2$ and about $10^3$, or between about 10 and about $10^2$ total microbial cells (e.g., CFU) per milliliter of fermented beverage. In some embodiments, the fermented beverage contains between $10^5$ and $10^6$ total microbial cells (e.g., CFU) per milliliter of fermented beverage. As discussed above, a microbial strain may be present in the same amount or a different amount as compared to another microbial strain.

The fermented beverages described herein may include one or more additional components that may contribute flavoring, aromatic, preservation, colorant, caffeine, sweetness, nutritive and/or functional properties to the beverage. In some embodiments, the fermented beverage may include one or more sweetening agents, such as natural sweeteners and artificial sweeteners. In some embodiments, the fermented beverage includes monk fruit sweetener. In some embodiments, the fermented beverage includes one or more sweet proteins. In some embodiments, the fermented beverage includes sucralose, tagatose, sugar alcohols (polyols, such as mannitol, sorbitol, xylito), aspartame, saccharin, acesulfame K, and/or stevia.

In some embodiments, the fermented beverage contains one or more additional flavoring components. Examples of additional flavoring components (natural, naturally derived, or synthetic) include, without limitation, fruit flavoring, including fruit extract, fruit juice, fruit peel, and fruit puree, such as apple, pear, blackberry, grape, nectarines, watermelon, banana pineapple, cherry, cranberry, lemon, lime, orange, citrus, grapefruit, cranberry, blueberry, quince, raspberry, strawberry, fig, apricot, plum, blackberry, pomelo, melon, mango, kiwi; vegetable flavoring, including vegetable extract, vegetable juice, and vegetable puree, such as carrot, celery, lettuce, wheatgrass, kale, broccoli, beans, cauliflower, cucumbers, squash, turnips, potatoes, yams, beets; herbs and spices, such as ginger, black pepper, cardamon, cinnamon, clove, nutmeg, chiles, mint, turmeric.

In some embodiments, the fermented beverage contains one or more additional nutritive components. Examples of nutritive components (natural, naturally derived, or synthetic) include, without limitation vitamins, minerals, and antioxidants, such as vitamin B complex, ascorbic acid (vitamin C), thiamine (vitamin B1), riboflavin (vitamin B2), niacin (vitamin B3), D-calcium pantothenate (vitamin B5), vitamin B6, vitamin B12, calcium, iron, vitamin D, vitamin E, vitamin A, vitamin K, magnesium, potassium, pantothenic acid, folic acid, zinc, and magnesium.

A fermented beverage that contains one or more nutritive components may be referred to as "fortified," such as vitamin and/or mineral fortified.

In some embodiments, the fermented beverages described herein further comprise tea or tea extract, such as non-fermented tea, semi-fermented tea, or fermented tea and extracts thereof. Examples of tea that may be used in the fermented beverages described herein include, without limitation, white tea, yellow tea, green tea, such as sencha, bancha, mochi tea, kettle tea, stem tea, stick tea, and bud tea: oolong tea, such as iron kannon, color type, golden katsura, and martial arts tea; black tea, Darjeeling, Assam, Ceylon, Sri Lanka, Keemun, Yunnan, Bai Lin Gong Fu; Nilgiri; herbal tea, and tea blends, such as Earl Grey, English breakfast, English afternoon, Irish breakfast, and masala chai. As will be evident to one of ordinary skill in the art, soluble compounds of tea leaves are typically extracted by hot water and/or steam and may be added to the fermented beverage.

Alternatively or in addition, any of the fermented beverages described herein may contain one or more functional components. As used herein, the term "functional component" refers to a component that may impart health benefits to the consumer other than basic nutritional components, such as promote hydration; promote healthy skin, nails, hair; increase energy; promote relaxation; enhance mood; improve digestion; promote immunity. Examples of functional components that may be used in the fermented beverages described herein include, without limitation, potassium, bamboo, biotin, silica, lavender, vanilla, passionflower, orange, rose, cucumber, lemon, strawberry, L-theanine, ginger, pineapple, black pepper, and turmeric.

Any of the fermented beverages described herein may further comprise one or more probiotic microbial strain, such as *Bacillus coagulans*, that may be added, for example, to the final product.

Methods of Production

Aspects of the present disclosure relate to methods of producing a fermented beverage using any of the symbiotic microbial communities described herein. In general, fermentation processes harness the ability of microorganisms to convert sugars into alcohol and organic acids. In the context of food and beverage production, fermentation broadly refers to any process in which the activity of microorganisms brings about a desirable change to a food product or beverage. The conditions for fermentation and the carrying out of a fermentation are referred to herein as a "fermentation process."

The methods of producing a fermented beverage described herein, such as kombucha, involve providing a medium comprising at least one fermentable sugar at an initial sugar level, adding any of the symbiotic microbial communities described herein to the medium to produce a culture, and subjecting the culture to suitable conditions for a period of time sufficient to ferment the culture (i.e., a fermentation process), thereby producing a fermented beverage. The microbial communities may be in the form of a starter culture containing each of the microbial strains of the community or in the form of multiple starter cultures each of which contains one microbial strain that when combined form the symbiotic microbial community. Starter cultures may be in any suitable form for adding to a medium, such as liquid, frozen, refrigerated, freeze dried, or lyophilized.

As used herein, the term "medium" refers to a composition that is conducive to fermentation, meaning a composition that does not inhibit fermentation. The medium may contain one or more fermentable sugar or may be supplemented with one or more fermentable sugar. In some embodiments, the medium is tea, water, juice, or extract.

The term "fermentable sugar," as used herein, refers to a carbohydrate that may be converted into an alcohol and carbon dioxide and ultimately to organic acids by microbial strains or a community thereof, such as any of the symbiotic microbial communities described herein. Examples of fermentable sugars include, without limitation, glucose, fructose, lactose, sucrose, maltose, and maltotriose.

In some embodiments, the method further involves adding the fermentable sugar to the medium. In some embodiments, the fermentable sugar is added to the medium prior to or during the fermentation process as a sugar source for the microbial strains. The sugar source for use in the fermented beverages and methods described herein may depend, for example, on the type of fermented beverage product and the fermentable sugar. Examples of sugar sources include, without limitation, fruit juice, fruit extract, vegetable juice, vegetable extract, honey, purified sugar such as cane sugar, palm sugar, beet sugar, maple syrup, brown sugar, molasses, agave nectar, honey, date syrup, date paste, date sugar, coconut sugar, monk fruit sweetener, and coconut water. In some embodiments, the sugar source is an artificial sugar source.

In some embodiments, the medium may comprise one or more additional flavoring component, that may be added prior to fermentation (e.g., teas, spices, natural flavorings, herbs). Examples of additional flavoring components (natural, naturally derived, or synthetic) include, without limitation, fruit flavoring, including fruit extract, fruit juice, fruit peel, and fruit puree, such as apple, pear, blackberry, grape, nectarines, watermelon, banana pineapple, cherry, cranberry, lemon, lime, orange, citrus, grapefruit, cranberry, blueberry, quince, raspberry, strawberry, fig, apricot, plum, blackberry, pomelo, melon, mango, kiwi; vegetable flavoring, including vegetable extract, vegetable juice, and vegetable puree, such as carrot, celery, lettuce, wheatgrass, kale, broccoli, beans, cauliflower, cucumbers, squash, turnips, potatoes, yams, beets, ginger, black pepper, cardamon, cinnamon, clove, nutmeg, chiles, mint, and turmeric. In some embodiments, the medium further comprises ginger or extracts derived or obtained from ginger.

As described herein, the medium comprises a fermentable sugar at an initial sugar level. During the fermentation process the fermentable sugar is converted to alcohol and organic acids, thereby reducing the sugar level in the medium to a final sugar level (content) in the fermented beverage that is lower than the initial sugar level. In some embodiments, the initial sugar level in the medium is about 2.5 g/L-20 g/L. In some embodiments, the initial sugar level in the medium is about 1.0 g/L, about 1.5 g/L, about 2.0 g/L, about 2.5 g/L, about 3.0 g/L, about 3.5 g/L, about 4.0 g/L, about 4.5 g/L, about 5.0 g/L, about 5.5 g/L, about 6.0 g/L, about 6.5 g/L, about 7.0 g/L, about 7.5 g/L, about 8.0 g/L, about 8.5 g/L, about 9.0 g/L, about 9.5 g/L, about 10 g/L, about 11 g/L, about 12 g/L, about 13 g/L, about 14 g/L, about 15 g/L, about 16 g/L, about 17 g/L, about 18 g/L, about 19 g/L, about 20 g/L.

In some embodiments, the initial pH of the medium is at or below 4.6. In some embodiments, the pH of the medium may be adjusted to reach an initial pH at or below 4.6. Suitable methods of adjusting the pH of a medium will be evident to one of ordinary skill in the art and may involve adding an acid, such as lemon juice, to the medium.

In some embodiments, fermentation conditions for use in the methods described herein that produce a fermented beverage may be carried out for about 1 day to about 60 days. In some embodiments, the fermentation process is performed for about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, about 35 days, about 40 days, about 45 days, about 50 days, about 55 days, about 60 days or longer. In some embodiments, the fermentation conditions involve incubating the culture at a temperature of about 15° C. to about 40° C. In some embodiments, the fermentation conditions involve incubating the culture at a temperature of about 15° C. to about 25° C., 20° C. to about 25° C., or about 18° C. to about 37° C. In some embodiments, the fermentation conditions involve incubating the culture at a temperature of about 20° C.-25° C. In some embodiments, the fermentation process of one or more fermentable sugars may be performed at a temperature of about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., or about 40° C. In some embodiments, the fermentation conditions involve incubating the culture at a temperature of about 20° C.

Fermenting the cultures to produce a fermented beverage may be performed in any suitable vessel, such as a batch reactor, carboy, fermenter, or jar. Examples of vessels for fermentation include, without limitation, static batch reactors (e.g., plastic bucket, glass bucket, stainless steel batch reactor (e.g., 5 gallon, 50 gallon, 500 gallon, 1000 gallon)), aerated batch reactors (e.g., vinegar fermenter, acetator), and more complex reactor, such as aerobic or anaerobic reactors, stirred or static reactors, batch or continuous reactors.

In some embodiments, one or more additional components, such as flavoring components, sweetening agents, or nutritive components, may be added to the medium prior to or after the fermentation process. In some embodiments, one or more additional components, such as flavoring components or nutritive components, may be added to the fermented beverage.

Various refinement, filtration, and processing steps may occur subsequent to fermenting the culture, after which the fermented beverage is bottled (e.g., captured and sealed in a container (e.g., glass bottle, aluminum can, etc) for distribution, storage, or consumption). Following bottling of the fermented beverages, minimal further fermentation may occur, however the levels of sugar, alcohol, and organic acids are stable. Any of the methods described herein may further involve pasteurizing and/or carbonating the fermented beverage. In some embodiments, the method further comprises carbonating the fermented beverage to produce a carbonated fermented beverage. Methods of carbonating fermented beverages are known in the art and include, for example, force carbonating with a gas (e.g., carbon dioxide, nitrogen), naturally carbonating by adding a further sugar source to the fermented beverage to promote further fermentation and production of carbon dioxide (e.g., bottle conditioning). In some embodiments, the fermented beverage is not carbonated (e.g., still).

EXAMPLES

Example 1: Use of Symbiotic Microbial Community to Produce an Exemplary Fermented Beverage To produce the fermented beverage, a base fermentation medium was prepared containing 10 g/L cane sugar, 0.55% ginger w/w, and 0.2% v/v lemon juice (unconcentrated), with an initial pH of approximately 3.9. The media was sterilized by boiling for at least 30 minutes in a 5 gallon stainless steel brewing container. The medium was allowed to cool to 30° C., and a starter culture of an exemplary symbiotic microbial community containing microbial strains having 16S rDNA sequences provided by SEQ ID NO: 5, SEQ ID NO: 2, SEQ ID NO: 6, and SEQ NO: 7 was then added to the medium (e.g., 1:250 v/v for liquid starter culture or an equivalent in final mass equivalent freeze-dried starter culture). The inoculated medium was fermented at room temperature (approximately 20° C.-22° C.) for 7-12 days, or until a final pH of approximately 2.8 was achieved with approximately $3\times10^7$ total CFU/mL. The final fermented beverage could then be flavored with spices or herbs, carbonated, and then canned or bottled for distribution and consumption.

Final levels of sugar(s), alcohol, and organic acid(s) were analyzed in the fermented beverage and compared to initial levels. The fermented beverages were also evaluated by blinded testers in a sensory panel based on smell and taste discriminants, such as consistency, mouthfeel, texture, taste, sweetness, bitterness, yeast, mineral, acetone, acid, sugar, fruit and balance.

Symbiosis and Fermentation Rate

To evaluate whether the microbial communities provided an advantage in the context of the rate of fermentation, the microbial community was fermented as a community or as each of the individual strains (each inoculated at 4-fold higher concentrations individually as compared to in combination in the community, such that the initial total microbial biomass was equivalent across fermentations). The same fermentation protocol was followed as described above with a 200 mL final volume and utilizing a 10 g/L (1%) cane sugar base with ginger. The initial sugar content was confirmed by enzymatic sugar testing for total sucrose, glucose, and fructose. Three distinct biological replicates were performed, and pH was determined daily by removing a 1 mL aliquot sample of the fermentation and measuring pH with a calibrated pH meter.

Figure 1A:
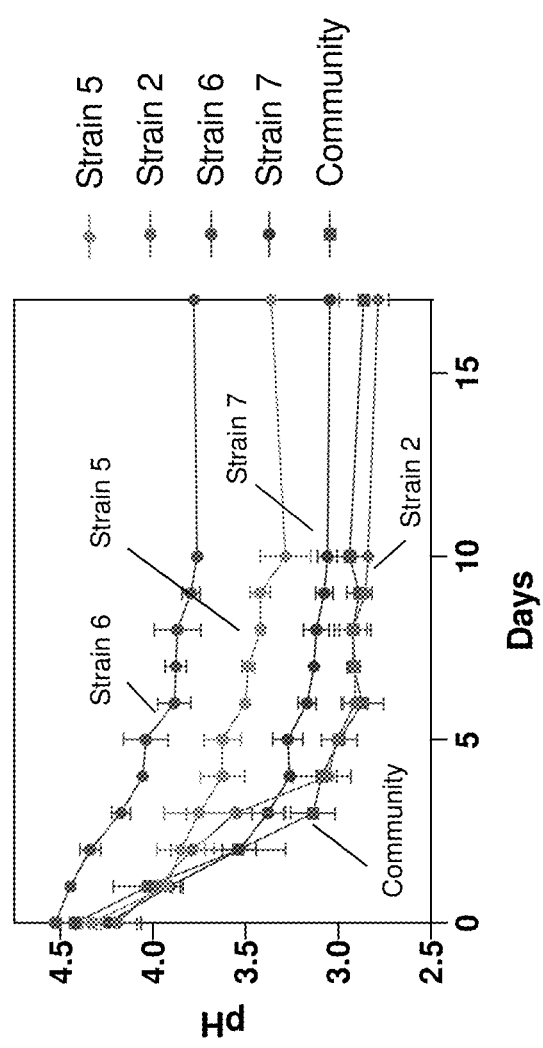
FIG. 1A shows the pH of fermentation reactions performed using the indicated individual microbial strains or the microbial community ("Community") at the indicated time points.

The microbial community was found to have faster fermentation speed than any of the individual strains (FIG. 1A). For example at day 3, the pH of the fermentation containing the microbial community was found to be significantly lower than the pH of the fermentation with the strain that best dropped pH (Strain7, SEQ ID NO: 7) (using unpaired T-test, two-sided, p=0.0463). See, FIG. 1B. These data indicated that the microbial community was symbiotic, and the microbial community had an increased fermentation rate as compared to the individual microbial strains.

Symbiosis and Biomass

To evaluate wherein the microbial communities provided an advantage in the context of the end biomass using viable cell count as a proxy, the microbial community was fermented as a community or with each of the individual strains (each inoculated at 4-fold higher concentrations individually as compared to in combination in the community). The same fermentation protocol was followed as described above with a 200 mL final volume and utilizing a 10 g/L (1%) cane sugar base. The initial sugar content was confirmed by enzymatic sugar testing for total sucrose, glucose, and fructose. Three distinct biological replicates were performed, and viable cell counts were determined daily by removing a sample of the fermentation and using a standard plating assay by plating a fixed volume of liquid on an agar plate at different dilutions and counting the number of colony forming units (CFUs).

Figure 2A:
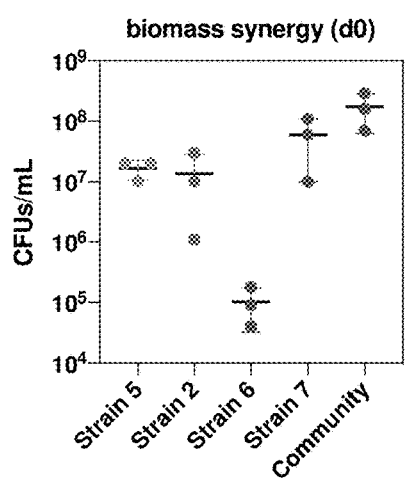
FIG. 2A shows the biomass (CFU/mL) of microbial strains in fermentation reactions performed using the indicated individual microbial strains or the microbial community ("Community") at the end of the fermentation process (day 0).
Figure 2B:
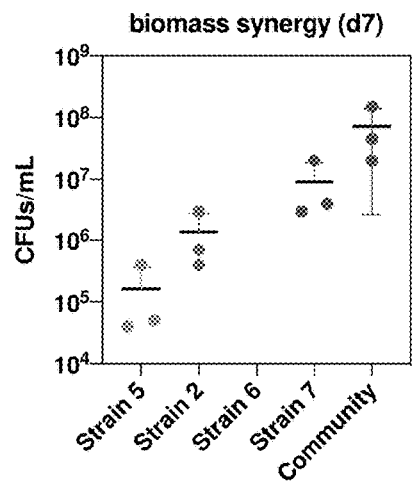
FIG. 2B shows the biomass of microbial strains in fermentation reactions performed using the indicated individual microbial strains or the microbial community ("Community") 7 days following the end of fermentation (day 7).
Figure 2C:
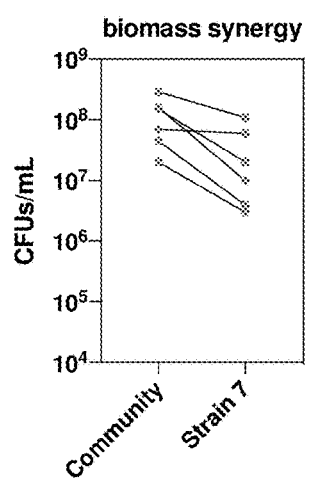
FIG. 2C shows the biomass of microbial strains in fermentation reactions performed using the microbial community ("Community") as compared to individual Strain 7 at 7 days following the end of fermentation (day 7). Each plot shows mean and standard deviation of 3 biological replicates. Strain 5 corresponds to SEQ ID NO: 5; Strain 2 corresponds to SEQ ID NO: 2; Strain 6 corresponds to SEQ ID NO: 6; and Strain 7 corresponds to SEQ ID NO: 7. Community corresponds to a microbial community containing Strains 5, 2, 6, and 7.

The microbial community together showed higher end biomass at the end of fermentation (FIG. 2A) and 7 days after the end of fermentation (FIG. 2A). At 7 days after fermentation, Strain 6 (SEQ ID NO: 6) was not detected above the assay limit of detection of $0.5 \times 10^4$ CFUs/mL. The end biomass of the microbial community was found to be significantly higher (effect size, ~5.5 fold higher) than the biomass of the strain that has the highest end biomass (Strain 7, SEQ ID NO: 7) (using paired T test, across Day 0 and Day 7, two sided, p=0.0078). See, FIG. 2C. These data indicated that the microbial community was symbiotic, and the microbial community had an increased end biomass as compared to the individual microbial strains.

Microbial Communities are Compatible with Various Recipe Bases and Concentrations The microbial communities were evaluated in fermentation processes involving different sugar bases. The same fermentation protocol was followed as described above with a 200 mL final volume utilizing different sugar bases (either "Ginger" containing cane sugar with ginger, or "Apple" containing apple fruit juice) at different initial sugar concentrations including 5 g/L, 10 g/L, 15 g/L and 20 g/L sugar base. The initial sugar content was confirmed by enzymatic sugar testing for total sucrose, glucose, and fructose.

Three distinct biological replicates were performed, and various measurements were performed including change in pH over time, community biomass, sugar profiling, and shelf stability assessments.

Figure 3B:
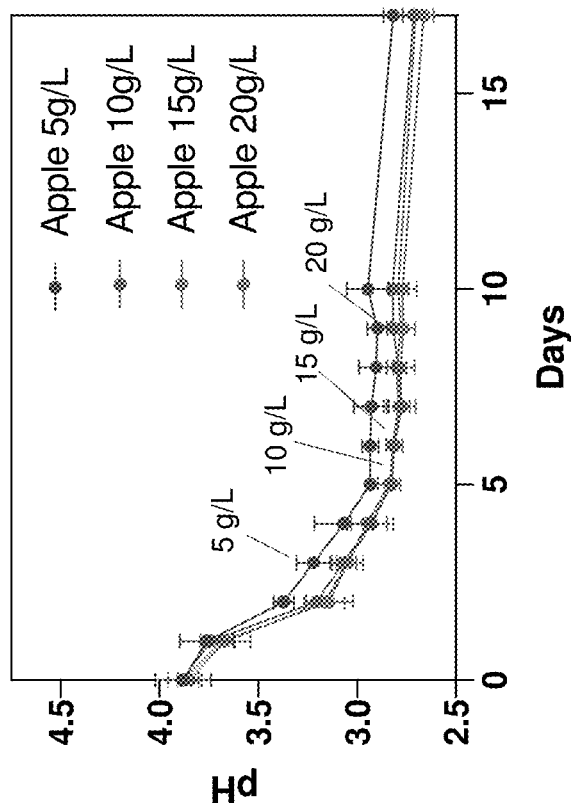
FIG. 3B shows the pH of fermentation reactions performed using the microbial community and various medium formulations containing apple fruit juice ("Apple") at the indicated initial sugar levels (5 g/L, 10 gL, 15 g/L, and 20 g/L). Each plot shows mean and standard deviation of 3 biological replicates.
Figure 3A:
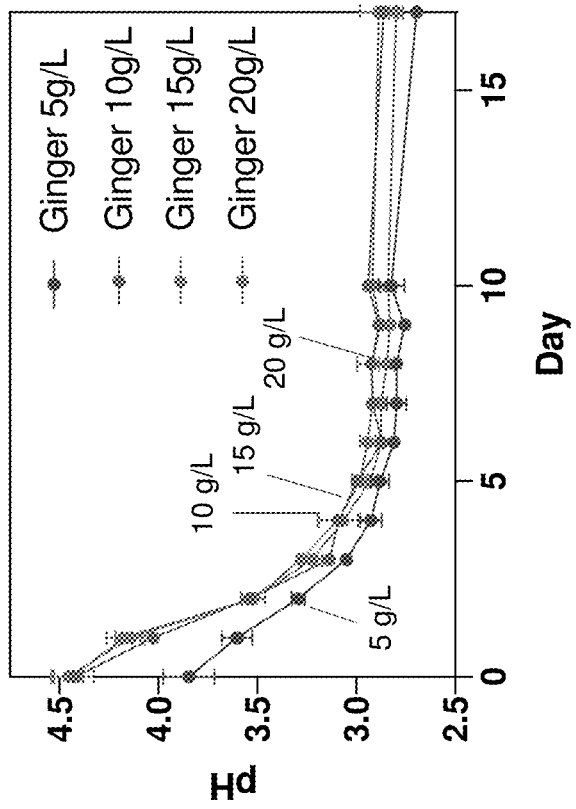
FIG. 3A shows the pH of fermentation reactions performed using the microbial community and various medium formulations containing cane sugar with ginger ("Ginger") at the indicated initial sugar levels (5 g/L, 10 gL, 15 g/L, and 20 g/L).
Figure 4:
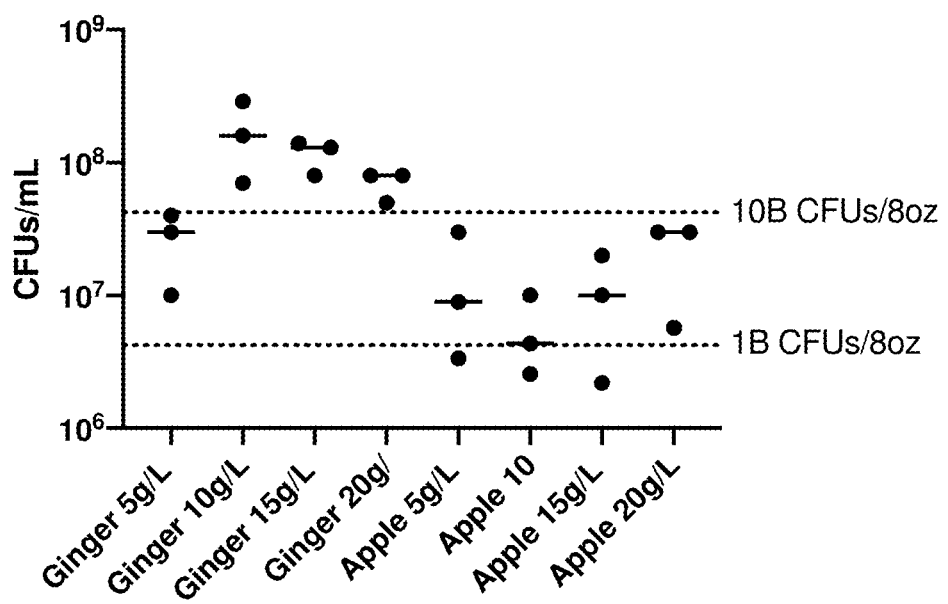
FIG. 4 shows the end biomass (CFU/mL) at the time of bottling of microbial strains in fermentation reactions using the microbial community and the medium formulations containing cane sugar with ginger ("Ginger") or apple fruit juice ("Apple") at the indicated initial sugar levels (5 g/L, 10 gL, 15 g/L, and 20 g/L). The plot shows mean and standard deviation of 3 biological replicates. The dotted lines correspond to the equivalent to 1 billion CFUs per 8 oz serving or 10 billion CFUs per 8 oz serving.

For each of the sugar bases and amounts tested, the microbial community was able to drop pH to below pH 3.0 within approximately 5-7 days (FIGS. 3A and 3B). As shown in FIG. 4, the microbial communities were found to reach a high number of end CFUs/mL, in most conditions higher than $10^7$ CFUs/mL. All fermentations reached more than 1 billion viable microbes per 8 fluid ounce serving on average.

Figure 5A:
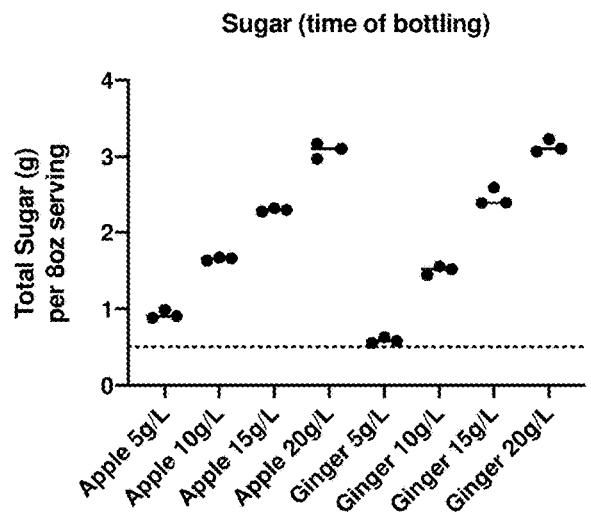
FIG. 5A shows terminal sugar levels of fermentation reactions using the microbial community and medium formulations containing cane sugar with ginger ("Ginger") or apple fruit juice ("Apple") at the indicated initial sugar levels (5 g/L, 10 g/L, 15 g/L, and 20 g/L) at the time of bottling.
Figure 5B:
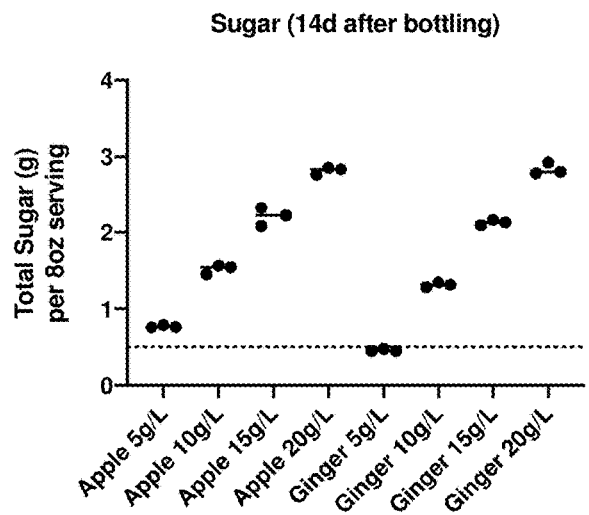
FIG. 5B shows terminal sugar levels of fermentation reactions using the microbial community and medium formulations containing cane sugar with ginger ("Ginger") or apple fruit juice ("Apple") at the indicated initial sugar levels 14 days after bottling.
Figure 5C:
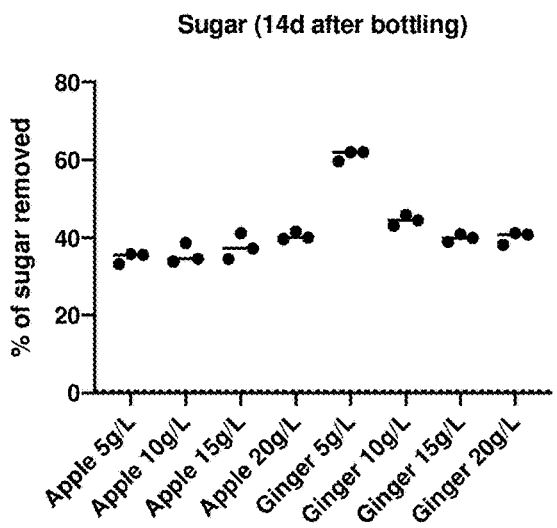
FIG. 5C shows the percent of sugar removed from medium formulations containing cane sugar with ginger ("Ginger") or apple fruit juice ("Apple") at the indicated initial sugar levels using the microbial communities at the time point 14 days after bottling.

In addition, the terminal sugar levels at the end of fermentation (e.g., the time of bottling) and 14 days later (e.g., 14 days after bottling) was determined by enzymatic sugar assay for total sucrose, glucose, and fructose. As shown in FIG. 5A the residual sugar level increased based on the initial sugar content in the different medium formulations. Sugar levels slightly decreased 14 days after bottling. See, FIG. 5B. The ginger/sugar base at an initial level of 5 g/L resulted in a residual level of sugar below the threshold of 0.5 g of sugar per 8 oz serving limit, allowing the product to be characterized as a 0-sugar beverage, according to the U.S. FDA Food Code. As shown in FIG. 5C the sugar levels were significantly reduced from starting amounts in all conditions.

Figure 6:
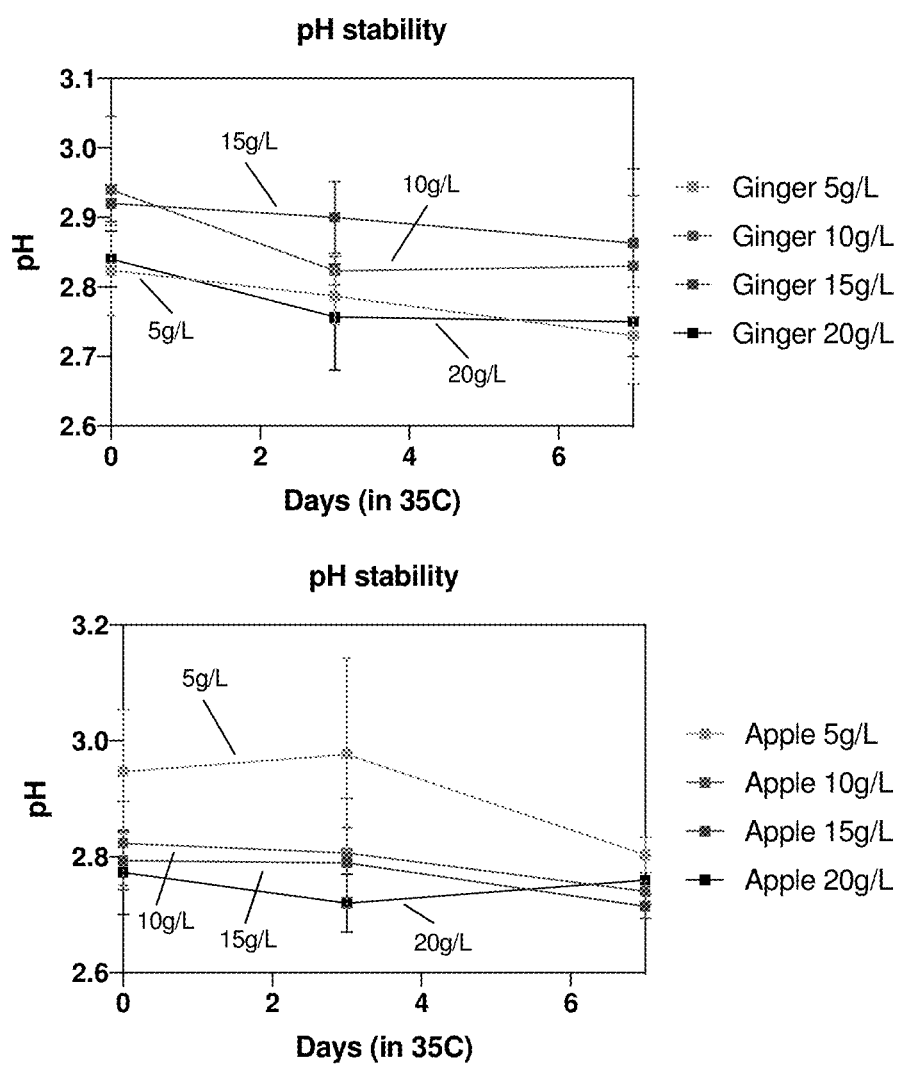
FIG. 6 shows the pH stability of fermented products produced by fermentation reactions using the microbial community and medium formulations containing cane sugar with ginger ("Ginger," top panel) or apple fruit juice ("Apple," bottom panel) indicated initial sugar levels (5 g/L, 10 g/L, 15 g/L, and 20 g/L). The fermented products were stored at 35° C. and assessed at the indicated time points. The plot shows mean and standard deviation of 3 biological replicates. The microbial community contains Strains 5, 2, 6, and 7.

In addition, the shelf stability of the fermented beverages was assessed using an accelerated 35° C. shelf stability assay. Briefly, fermented beverages were maintained at 35° C. elevated temperatures. Fermented beverages maintained at 35° C. for 5 days (across all sugar concentrations and fruit/sugar bases) were indistinguishable from samples refrigerated immediately after fermentation in a blinded taste/sensory panel. As shown in FIG. 6, the pH of the fermented products remained stable when held at 35° C. at the time points assessed.

Figure 7:
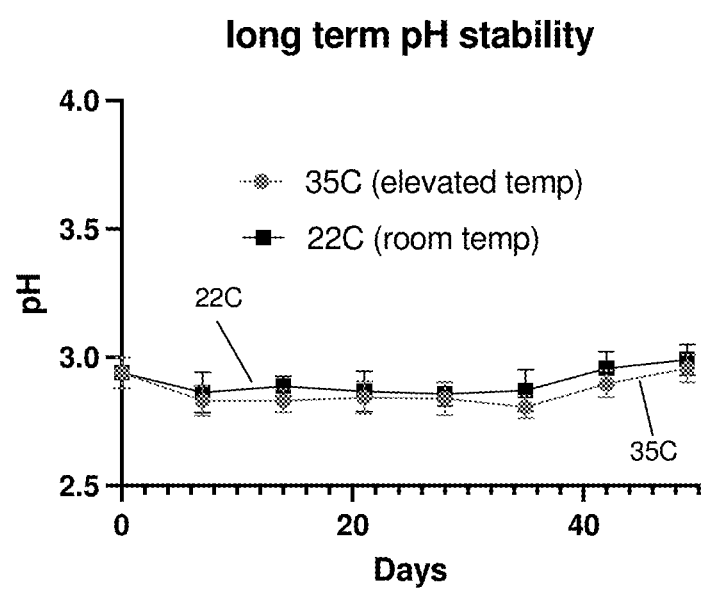
FIG. 7 shows the long term pH stability of fermented products produced by fermentation reactions using the microbial community and subsequently stored at an elevated temperature (35° C.) or at room temperature (22° C.). The pH was assessed on each of the indicated days post fermentation. The plot shows mean and standard deviation of 3 biological replicates. The microbial community contains Strains 2, 4, 5, and 7.

In addition, the longer term shelf stability of the fermented beverages was assessed in an independent experiment following the protocol described above. A base medium containing 10 g/L cane sugar with ginger was utilized for the fermentation. The pH was analyzed over time for fermented beverages that were stored at room temperature (22° C.) and high temperature (35° C.). As shown in FIG. 7, the pH of the fermented beverages remained stable over the time assessed, more than 6 weeks.

Figure 8:
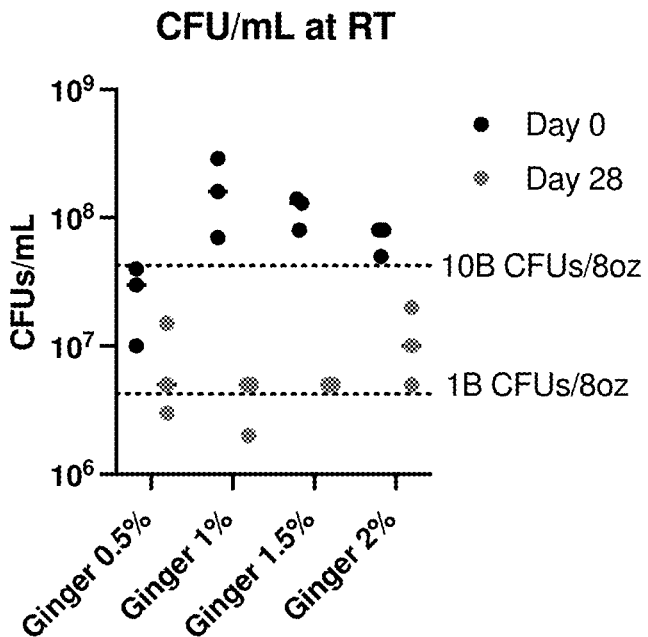
FIG. 8 shows the biomass (CFU/mL) at the time of bottling of microbial strains in fermentation reactions using the microbial community and the medium formulations containing cane sugar with ginger ("Ginger") at the indicated initial sugar levels (0.5%, 1%, 1.5%, and 2%) at the end of fermentation (Day 0) or following storage at room temperature (22° C.) for 28 days (Day 28). The plot shows the mean and individual results of 3 biological replicates. The microbial community contains Strains 2, 4, 5, and 7.

In addition, the stability of microbial cultures in the fermented beverages was also assessed. A base media containing cane sugar with ginger with sugar levels of 5 g/L, 10 g/L, 15 g/L and 20 g/L were utilized for the fermentations, which were performed as described above. The biomass (CFUs/mL) of each fermented beverage was determined at the end of fermentation (day 0) and after 28 days (day 28) of storage at room temperature. As shown in FIG. 8, while CFUs/mL decreased over time, nearly all fermented beverages retained on the order of billions of CFUs per 8 oz serving after the extended storage time.

Alcohol Content

Figure 9:
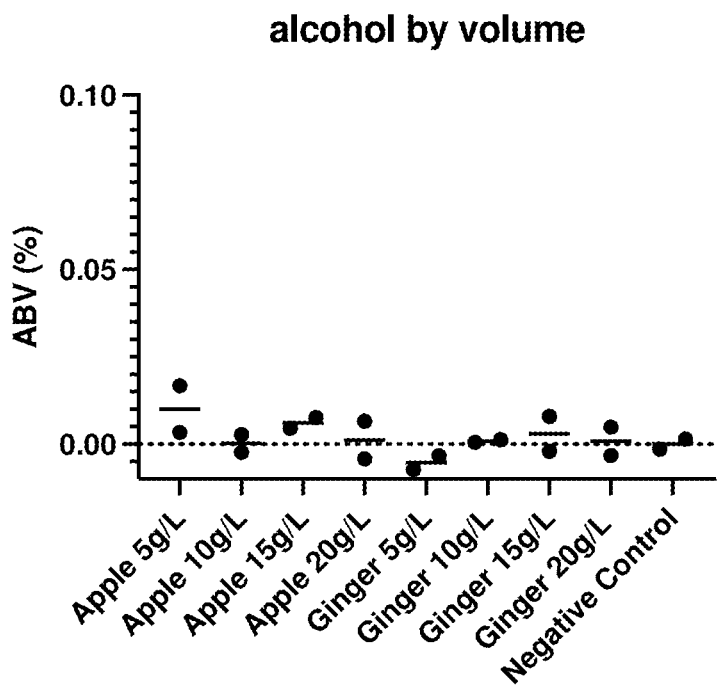
FIG. 9 shows alcohol by volume (% ABV) of fermentation reactions using the microbial community and medium formulations containing cane sugar with ginger ("Ginger") or apple fruit juice ("Apple") at the indicated initial sugar levels (5 g/L, 10 g/L, 15 g/L, and 20 g/L), as compared to the negative control (assay blank). The % ABV was assessed at three weeks after fermentation finished. The plot shows the mean and individual results of 2 technical replicates. The microbial community contains Strains 2, 4, 5, and 7.

The same fermentation protocol was followed as described above utilizing different sugar bases (either "Ginger" containing cane sugar with ginger, or "Apple" containing apple fruit juice) at different initial sugar concentrations including 5 g/L, 10 g/L, 15 g/L and 20 g/L sugar base. The alcohol content (alcohol by volume (ABV)) was assessed for the fermented beverages by enzymatic enzyme assay following AOAC Official Method 2019.08 (see, e.g., Ivory et al. J. AOAC Inter. (2020) 104(2): 422-430), using a commercially available kit per the manufacturers recommendations. As shown in FIG. 9, the ABV of each of the fermented beverages was low and near undetectable levels.

In sum, these data indicate that the microbial communities can be used in fermentation processes using medium containing various formulations, such as juice and sugar bases, and result in successful fermentation, with high viable CFUs, while significantly reducing sugar, and being shelf-stable.

Strain Stability in Fermented Beverages

The stability of the microbial strains in the fermented beverages was also evaluated over time. Fermentations were performed using a microbial community or as individual strains. For the individual strain fermentations, each strain was inoculated at 4-fold higher concentrations as compared to the combination in the community. The fermentations were performed as described in Example 1 using a 200 mL final volume and a 10 g/L (1%) cane sugar base medium.

The initial sugar content was confirmed by enzymatic sugar testing for total sucrose, glucose, and fructose. Three independent biological replicates were performed. Viable cell counts were determined over 80 days by removing a sample of the fermentation and using a standard plating assay to enumerate colony forming units (CFUs) at each time point.

Figure 10:
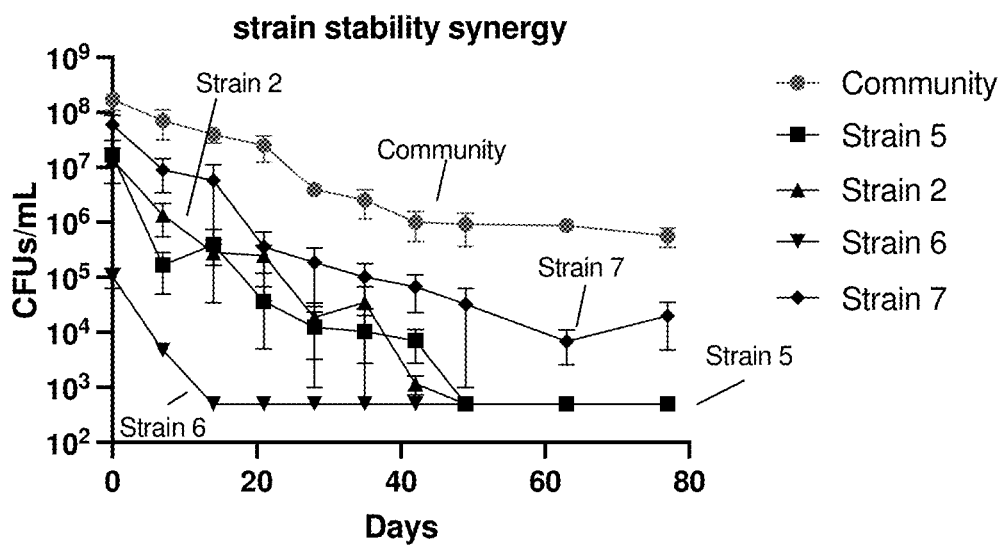
FIG. 10 shows the stability of the biomass (CFU/mL) in fermentation reactions performed using the microbial community ("Community") as compared to the individual strains at the indicated time points post-fermentation. Strain 5 corresponds to SEQ ID NO: 5; Strain 2 corresponds to SEQ ID NO: 2; Strain 6 corresponds to SEQ ID NO: 6; and Strain 7 corresponds to SEQ ID NO: 7. Community corresponds to a microbial community containing Strains 5, 2, 6, and 7. The plot shows the mean and individual results of 3 biological replicates.

As shown in FIG. 10, the microbial strains when fermented as a community resulted in significantly higher stability (i.e., higher CFUs/mL) over time, as compared to the strains when fermented individually, indicating synergy in microbial stability over time in the fermented beverage.

Example 2: Use of Diverse Microbial Communities to Produce Fermented Beverages

It was observed that the combination of acetic acid bacterial strains (GROUP I) and lactic acid bacterial strains (GROUP II) led to desirable emergent characteristics with respect to sensory profile of the fermented beverage and ability of the microbial community to ferment sugar to acids better (faster, more efficiently) than individual microbial strains.

Additional example microbial communities were designed containing at least one strain from GROUP I, at least one strain from GROUP II, and optionally one or more accessory strains from GROUP III, see Table 1. Each complex community was assembled (in triplicate) on a microtiter plate in 80 μL following a similar protocol described in Example 1. The change in pH was assessed at various time points over the course of four days. Single-strain fermentations containing the individual microbial strains (in triplicate) were performed.

The terminal pH was determined at 99.3 hours by taking the median across replicates (with linear interpolation to account for minor offset in measurement times). The level of synergy in the microbial communities (i.e., symbiotically fermented sugar to acid more efficiently as a microbial community as compared to the individual microbial strain) was assessed by computing a "synergy score" at each timepoint. Specifically, the synergy score represents the difference in median pH of the microbial community versus the minimal median pH of the individual microbial strains (with scores below zero corresponding to communities that exhibit synergy, on a logarithmic scale). Table 1 shows grouping of microbial strains used to generate the microbial communities described herein. Table 2 shows the median terminal pH, as well as the synergy score at the terminal timepoint, for all synergistic combinations.

TABLE 1

Microbial strains

| GROUP I | GROUP II | GROUP III |
|---|---|---|
| Strain 1 (SEQ ID NO: 1) | Strain 4 (SEQ ID NO: 4) | Strain 8 (SEQ ID NO: 8) |
| Strain 2 (SEQ ID NO: 2) | Strain 5 (SEQ ID NO: 5) | Strain 9 (SEQ ID NO: 9) |
| Strain 3 (SEQ ID NO: 3) | Strain 6 (SEQ ID NO: 6) | Strain 10 (SEQ ID NO: 10) |
| | Strain 7 (SEQ ID NO: 7) | Strain 11 (SEQ ID NO: 11) |
| | | Strain 12 (SEQ ID NO: 12) |
| | | Strain 13 (SEQ ID NO: 13) |
| | | Strain 14 (SEQ ID NO: 14) |
| | | Strain 15 (SEQ ID NO: 15) |
| | | Strain 16 (SEQ ID NO: 16) |
| | | Strain 17 (SEQ ID NO: 17) |
| | | Strain 18 (SEQ ID NO: 18) |
| | | Strain 19 (SEQ ID NO: 19) |

TABLE 2

Synergy scores and terminal pH of exemplary microbial communities

| Sequence IDs | Groups | Synergy (median n = 3 replicates) | Terminal pH (median n = 3 replicates) |
|---|---|---|---|
| SEQ 2, SEQ 4, SEQ 9 | GROUP I, GROUP II, GROUP III | −1.48 | 2.89 |
| SEQ 2, SEQ 4, SEQ 5 | GROUP I, GROUP II, GROUP II | −1.07 | 3.14 |
| SEQ 1, SEQ 2, SEQ 2, SEQ 4, SEQ 5 | GROUP I, GROUP I, GROUP I, GROUP II, GROUP II | −0.51 | 2.86 |
| SEQ 1, SEQ 2, SEQ 4, SEQ 5 | GROUP I, GROUP I, GROUP II, GROUP II | −0.36 | 3.01 |
| SEQ 1, SEQ 2, SEQ 6, SEQ 6 | GROUP I, GROUP I, GROUP II, GROUP II | −0.33 | 3.04 |
| SEQ 1, SEQ 4, SEQ 4, SEQ 4, SEQ 5 | GROUP I, GROUP II, GROUP II, GROUP II, GROUP II | −0.09 | 3.28 |
| SEQ 1, SEQ 4, SEQ 4, SEQ 5 | GROUP I, GROUP II, GROUP II, GROUP II | −0.09 | 3.28 |
| SEQ 1, SEQ 4, SEQ 4, SEQ 5 | GROUP I, GROUP II, GROUP II, GROUP II | −0.09 | 3.28 |
| SEQ 1, SEQ 4, SEQ 4, SEQ 5 | GROUP I, GROUP II, GROUP II, GROUP II | −0.06 | 3.31 |
| SEQ 1, SEQ 4, SEQ 4, SEQ 4, SEQ 5 | GROUP I, GROUP II, GROUP II, GROUP II, GROUP II | −0.06 | 3.31 |
| SEQ 1, SEQ 4, SEQ 4, SEQ 5 | GROUP I, GROUP II, GROUP II, GROUP II | −0.06 | 3.31 |
| SEQ 1, SEQ 4, SEQ 4, SEQ 5, SEQ 6 | GROUP I, GROUP II, GROUP II, GROUP II, GROUP II | −0.05 | 3.32 |
| SEQ 1, SEQ 4, SEQ 4, SEQ 4, SEQ 5 | GROUP I, GROUP II, GROUP II, GROUP II, GROUP II | −0.05 | 3.32 |
| SEQ 1, SEQ 4, SEQ 4, SEQ 5, SEQ 6 | GROUP I, GROUP II, GROUP II, GROUP II, GROUP II | −0.05 | 3.32 |
| SEQ 1, SEQ 2, SEQ 3, SEQ 3, SEQ 6 | GROUP I, GROUP I, GROUP I, GROUP I, GROUP II | −0.04 | 2.81 |
| SEQ 3, SEQ 4, SEQ 4, SEQ 4, SEQ 5 | GROUP I, GROUP II, GROUP II, GROUP II, GROUP II | −0.03 | 2.82 |
| SEQ 1, SEQ 4, SEQ 5, SEQ 5 | GROUP I, GROUP II, GROUP II, GROUP II | −0.03 | 3.34 |
| SEQ 1, SEQ 4, SEQ 4, SEQ 13 | GROUP I, GROUP II, GROUP II, GROUP III | −0.02 | 2.88 |

TABLE 2-continued

Synergy scores and terminal pH of exemplary microbial communities

| Sequence IDs | Groups | Synergy (median n = 3 replicates) | Terminal pH (median n = 3 replicates) |
|---|---|---|---|
| SEQ 1, SEQ 5, SEQ 13 | GROUP I, GROUP II, GROUP III | −0.02 | 2.88 |
| SEQ 1, SEQ 4, SEQ 4, SEQ 5, SEQ 6 | GROUP I, GROUP II, GROUP II, GROUP II, GROUP II | −0.02 | 3.35 |
| SEQ 1, SEQ 5, SEQ 6, SEQ 6, SEQ 11 | GROUP I, GROUP II, GROUP II, GROUP II, GROUP III | −0.02 | 3.35 |
| SEQ 2, SEQ 3, SEQ 4, SEQ 6, SEQ 7 | GROUP I, GROUP I, GROUP II, GROUP II, GROUP II | −0.01 | 2.84 |
| SEQ 1, SEQ 4, SEQ 5, SEQ 5 | GROUP I, GROUP II, GROUP II, GROUP II | −0.01 | 3.36 |
| SEQ 1, SEQ 4, SEQ 4, SEQ 5, SEQ 5 | GROUP I, GROUP II, GROUP II, GROUP II, GROUP II | −0.01 | 3.36 |

Furthermore, fermentations using the microbial communities described in Table 1 were scaled up to produce a fermented beverage. Using the fermentation protocol described in Example 1, the microbial communities were fermented at 200 mL scales. At terminal fermentation, various properties of the fermented beverages were measured including total sugar content, acetic acid level, gluconic acid level, and D-/L-lactic acid level, each determined by enzymatic sugar assays.

Table 3 shows data from the fermented beverages corresponding to the mean of technical triplicate measurements. Each of the microbial communities significantly reduced the initial sugar content below the initial 10 g/L level, and the fermented beverages contained high levels of organic acids (e.g., gluconic, lactic acid). In addition, the acetic acid levels in the fermented beverages produced using the microbial communities were significantly lower than fermented beverages such as kombucha produced using conventional methods, which are typically between 4-8 g/L.

TABLE 3

Characteristics of fermented beverages produced using the exemplary microbial communities

| Sequence IDs | Groups | Sucrose (g/L) | D-Glucose (g/L) | D-Fructose (g/L) | Total Sugars (g/L) | Acetic Acid (g/L) | Gluconic Acid (g/L) | D-Lactic/L-Lactic Acid (g/L) | Terminal pH |
|---|---|---|---|---|---|---|---|---|---|
| SEQ 5, SEQ 2, SEQ 6, SEQ 7 | GROUP II, GROUP I, GROUP II, GROUP II | 0.97 | 0.27 | 2.69 | 4.55 | 0.62 | 0.82 | 1.41 | 2.82 |
| SEQ 5, SEQ 2, SEQ 4 | GROUP II, GROUP I, GROUP II | 1.39 | 0.35 | 3.18 | 5.79 | 0.12 | 0.86 | 0.03 | 2.69 |
| SEQ 2, SEQ 1, SEQ 4, SEQ 5, SEQ 6, SEQ 7 | GROUP I, GROUP I, GROUP II, GROUP II, GROUP II, GROUP II | 1.33 | 0.25 | 2.83 | 5.20 | 0.49 | 0.67 | 1.17 | 2.70 |
| SEQ 5, SEQ 2, SEQ 1 | GROUP II, GROUP I, GROUP I | 1.39 | 0.88 | 3.24 | 6.65 | 0.05 | 0.95 | 0.02 | 2.76 |
| SEQ 5, SEQ 2, SEQ 1, SEQ 4, SEQ 7 | GROUP II, GROUP I, GROUP I, GROUP II, GROUP II | 1.34 | 0.31 | 3.43 | 5.92 | 0.53 | 0.86 | 1.08 | 2.72 |
| SEQ 2, SEQ 1, SEQ 4, SEQ 6, SEQ 7 | GROUP I, GROUP I, GROUP II, GROUP II, GROUP II | 1.48 | 0.21 | 2.88 | 5.41 | 0.40 | 0.67 | 1.10 | 2.77 |
| SEQ 5, SEQ 2, SEQ 4, SEQ 7 | GROUP II, GROUP I, GROUP II, GROUP II | 1.56 | 0.19 | 2.65 | 5.27 | 0.53 | 0.56 | 1.09 | 2.73 |
| SEQ 5, SEQ 7, SEQ 9, SEQ 4, SEQ 3 | GROUP II, GROUP II, GROUP III, GROUP II, GROUP I | 0.23 | 0.94 | 3.71 | 5.46 | 0.14 | 1.84 | 1.00 | 2.82 |
| SEQ 7, SEQ 9, SEQ 4, SEQ 3 | GROUP II, GROUP III, GROUP II, GROUP I | 0.44 | 1.19 | 3.57 | 6.01 | 0.14 | 1.89 | 0.92 | 2.86 |

Example 3: Resistance to Contaminating Microorganisms

To assess resilience of fermented beverages containing the microbial communities described herein to contaminating microorganisms, a challenge study was performed. In general, for a challenge study, fermentations are prepared as described in Example 1 containing a microbial community or individual microbial strains. Undesired microorganisms, such as those that may be found commonly in brewery environments (e.g., contaminants, pathogens such as *Brettanomyces* sp. or *Saccharomyces* sp.), are added to the fermentation at initial fermentation or at various time points during fermentation (for example, in the middle of fermentation, e.g., at day 3).

Here, microbial communities were fermented as a community (strains 2, 5, 6, and 7) or an individual strains. For the individual strain fermentations, each strain was inoculated at 4-fold higher concentrations as compared to the combination in the community. The fermentations were performed as described in Example 1 using a 200 mL final volume and a 10 g/L (1%) cane sugar base medium. The initial sugar content was confirmed by enzymatic sugar testing for total sucrose, glucose, and fructose. Four to five independent biological replicates were performed.

Figure 11:
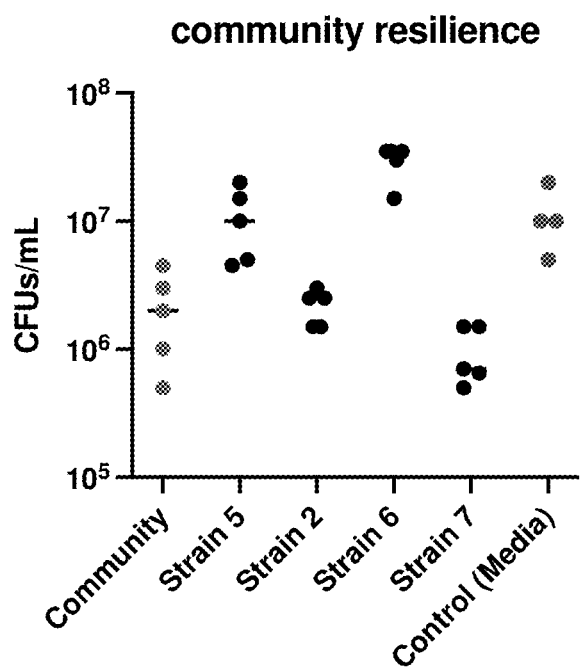
FIG. 11 shows the biomass (CFU/mL) of contaminant strain following inoculation of *Brettanomyces* sp. into fermentation reactions performed using the microbial community ("Community") as compared to the individual strains and a negative control (media alone). Strain 5 corresponds to SEQ ID NO: 5; Strain 2 corresponds to SEQ ID NO: 2; Strain 6 corresponds to SEQ ID NO: 6; and Strain 7 corresponds to SEQ ID NO: 7. Community corresponds to a microbial community containing Strains 5, 2, 6, and 7. The plot shows the mean and individual results of 4 or 5 biological replicates.

The undesired microorganism *Brettanomyces* sp. was introduced at a 1:100 dilution at the initial fermentations. CFUs/mL of the *Brettanomyces* were determined by plating on selective enumeration media. As shown in FIG. 11, the fermentations containing the microbial community displayed significant resilience to invasion as compared to the control and equal to or better than the several of the fermentations containing the individual strains, demonstrating collective resilience conferred by the microbial community.

Example 4: Analysis of Exemplary Fermented Product

A fermented beverage was produced using a community containing Strains 2, 5, 6, and 7, as described in Example 1 using a medium containing 1% sugar and ginger. End organic acid profiles depend on factors such as the starting medium formulation. All assays were enzymatic assays, and the values shown below represent the average of three technical replicates:

1% sugar base with ginger
Acetic acid: 0.62 g/L
Gluconic acid: 0.82 g/L
D- and L-Lactic acid (sum): 1.41 g/L Further fermented beverages were produced using a community containing Strains 2, 4, 5, and 7, as described in Example 1 using a medium containing 1% sugar or 1% fruit juice (corresponding to a 10 g/L initial sugar level). Samples of the fermented beverage were further evaluated using full kombucha profile testing, including sugar profile analysis. See, Tables 4, 5, and 6.

TABLE 4

Results of kombucha profile analysis

| Test | Method | Result | Units |
|---|---|---|---|
| Alcohol by volume by gas chromatograph | AOAC 2016.12 | 0.02 | Percent |
| Total Yeast Count | AOAC 2014.05 | None Detected | CFUs/mL |
| Total Mold Count | AOAC 2014.05 | None Detected | CFUs/mL |
| Total Aerobic Bacteria Count | AOAC 2015.13 | 186,000,000 | CFUs/mL |
| *Staphylococcus aureus* | AOAC 2003.07 | None Detected | CFUs/mL |
| *E. coli* | 3M Petrifilm *E. Coli*/Coliform Count Plates | None Detected | CFUs/mL |
| pH | ASBC Beer-9 | 2.86 | |
| Titratable Acidity (Measured as Acetic Acid) | AOAC 942.15 | 1.14 | g/L |
| Acetic Acid | Enzymatic | 0.74 | g/L |
| Gluconic Acid | Enzymatic | 0.02 | g/L |
| Lactic Acid | Enzymatic | 0.05 | g/L |
| Malic Acid | Enzymatic | 1 | mg/L |

TABLE 5

Sugar profile of a fermented beverage produced using a medium containing 1% sugar

| Analysis Sugar Profile | Result |
|---|---|
| Fructose | 0.25% |
| Glucose | <0.10% |
| Sucrose | <0.10% |
| Lactose | <0.10% |
| Maltose | <0.10% |
| Galactose | <0.10% |
| Total Sugar | 0.25% |

TABLE 6

Sugar profile of a fermented beverage produced using a medium containing 1% fruit juice

| Analysis Sugar Profile | Result |
|---|---|
| Fructose | 0.18% |
| Glucose | 0.13% |
| Sucrose | 0.14% |
| Lactose | <0.10% |
| Maltose | <0.10% |
| Galactose | <0.10% |
| Total Sugar | 0.45% |

ENUMERATED EMBODIMENTS

1. A fermented beverage comprising
a symbiotic microbial community comprising at least one bacterial strain having a 16S rDNA sequence comprising at least 95% sequence identity to a nucleic acid sequence provided by SEQ ID NOs: 1-3, and at least one bacterial strain having a 16S rDNA sequence comprising at least 95% sequence identity to a nucleic acid sequence provided by SEQ ID NOs: 4-7, and at least one additional microbial strain,
a sugar content that is less than 20 grams per liter (g/L), and
an ethanol level that is less than 0.5% alcohol by volume (abv, v/v).

2. The fermented beverage of embodiment 1, wherein the symbiotic microbial community comprises at least two, at least three, or at least four additional microbial strains.

3. The fermented beverage of embodiment 1 or 2, wherein at least one of the additional microbial strains is a bacterial strain.

4. The fermented beverage of any one of embodiments 1-3, wherein each of the additional microbial strains is a bacterial strain.

5. The fermented beverage of any one of embodiments 2-4, wherein the additional bacterial strain belongs to the genus *Lactobacillus, Gluconobacter, Leuconostoc, Acetobacter, Hafnia/Obesumbacterium, Lactococcus, Pediococcus*, or *Bacillus*.

6. The fermented beverage of embodiment 5, wherein the additional bacterial strain belongs to the species *Acetobacter pasteurianus, A. ghanesis, A. orientalis, A. tropicalis, Gluconobacter oxydans, G. roseus, G. japonicus, G. frateurii, Leuconostoc mesenteroides, Lactobacillus senmaizukei, L. brevis, L. parakefiri, L. hilgardii, L. diolivorans, L. rapi, L. kisonesis, L. buchneri, L. fuchuensis, L. plantarum, L. paraplantarum, L. fabifermentans, L. pentosus, L. graminis, L. composti, Bacillus zanthoxyli, B. qingshengii, B. aryabhattai, B. flexus, B. megaterium, Hafnia alvei, Obesumbacterium proteus, Lactococcus taiwanensis, L. lactis, Lactobacillus casei, L. paracasei, Pediococcus claussenii, P. stilesii, P. pentosaceus, P. acidilactici, Gluconacetobacter liquefaciens, Lactobacillus cerevisiae, L. kefiri, L. sunkii, L. otakiensis, L. parabuchneri, Leuconostoc lactis, L. palmae, L. holzapfelii, L. citreum, Lactobacillus nagelii, L. satsumensis, Acetobacter papayae, A. suratthaniensis, A. peroxydans, Gluconacetobacter takamatsuzukensis*, or *G. asukensis*.

7. The fermented beverage of any one of embodiments 1-6, wherein the additional bacterial strain has a 16S rDNA sequence comprising at least 95% sequence identity to a nucleic acid sequence provided by SEQ ID NOs: 8-19.

8. The fermented beverage of any one of embodiments 1-7, wherein the symbiotic microbial community comprises bacterial strains having a 16S rDNA sequence comprising at least 95% sequence identity to a nucleic acid sequence provided by SEQ ID NOs: 2, 4, 5, 6, 7, and 20-24.

9. The fermented beverage of any one of embodiments 1-8, wherein the symbiotic microbial community comprises bacterial strains having a 16S rDNA sequence comprising at least 95% sequence identity to a nucleic acid sequence provided by SEQ ID NOs: 2, 5, 6, and 7.

10. The fermented beverage of any one of embodiments 1-7, wherein the symbiotic microbial community comprises bacterial strains having a 16S rDNA sequence comprising at least 95% sequence identity to a nucleic acid sequence provided by SEQ ID NOs: 2, 4, and 5.

11. The fermented beverage of any one of embodiments 1-9, wherein the symbiotic microbial community consists of bacterial strains having a 16S rDNA sequence comprising at least 95% sequence identity to a nucleic acid sequence provided by SEQ ID NOs: 2, 5, 6, and 7.

12. The fermented beverage of any one of embodiments 1-8 and 10, wherein the symbiotic microbial community consists of bacterial strains having a 16S rDNA sequence comprising at least 95% sequence identity to a nucleic acid sequence provided by SEQ ID NOs: 2, 4, and 5.

13. The fermented beverage of any one of embodiments 1-9, wherein the symbiotic microbial community comprises bacterial strains having a 16S rDNA sequence comprising at least 95% sequence identity to a nucleic acid sequence provided by SEQ ID NOs: 21, 20, 22, and 24.

14. The fermented beverage of any one of embodiments 1-8 and 10, wherein the symbiotic microbial community comprises bacterial strains having a 16S rDNA sequence comprising at least 95% sequence identity to a nucleic acid sequence provided by SEQ ID NOs: 21, 23, and 20.

15. The fermented beverage of any one of embodiments 1-9 and 13, wherein the symbiotic microbial community consists of bacterial strains having a 16S rDNA sequence comprising at least 95% sequence identity to a nucleic acid sequence provided by SEQ ID NOs: 21, 20, 22, and 24.

16. The fermented beverage of any one of embodiments 1-8, 10, and 14, wherein the symbiotic microbial community consists of bacterial strains having a 16S rDNA sequence comprising at least 95% sequence identity to a nucleic acid sequence provided by SEQ ID NOs: 21, 23, and 20.

17. The fermented beverage of any one of embodiments 1-8, wherein the symbiotic microbial community comprises bacterial strains having a 16S rDNA sequence comprising at least 95% sequence identity to a nucleic acid sequence provided by SEQ ID NOs: 2, 4, 5, and 7.

18. The fermented beverage of any one of embodiments 1-8 and 17, wherein the symbiotic microbial community consists of bacterial strains having a 16S rDNA sequence comprising at least 95% sequence identity to a nucleic acid sequence provided by SEQ ID NOs: 2, 4, 5, and 7.

19. The fermented beverage of any one of embodiments 1-8 or 17, wherein the symbiotic microbial community comprises bacterial strains having a 16S rDNA sequence comprising at least 95% sequence identity to a nucleic acid sequence provided by SEQ ID NOs: 21, 23, 20, and 24.

20. The fermented beverage of any one of embodiments 1-8, 17, and 19, wherein the symbiotic microbial community consists of bacterial strains having a 16S rDNA sequence comprising at least 95% sequence identity to a nucleic acid sequence provided by SEQ ID NOs: 21, 23, 20, and 24.

21. The fermented beverage of any one of embodiments 1-20, wherein the symbiotic microbial community does not comprise a yeast strain.

22. The fermented beverage of any one of embodiments 1-21, wherein the symbiotic microbial community comprises at least $2 \times 10^7$ colony forming units of each bacterial strain and each additional microbial strain per milliliter of the fermented beverage.

23. The fermented beverage of any one of embodiments 1-22, comprising a level of acetic acid less than 1 gram per liter (g/L).

24. The fermented beverage of any one of embodiments 1-23, comprising a level of organic acid that is greater than 1 gram per liter (g/L), wherein the organic acid is not acetic acid.

25. The fermented beverage of embodiment 24, wherein the organic acid is lactic acid, gluconic acid, ketogluconic acid, or a combination thereof.

26. The fermented beverage of any one of embodiments 1-25, wherein the fermented beverage is shelf stable for at least 2 weeks at a temperature of about 20° C.

27. The fermented beverage of any one of embodiments 1-26, wherein the fermented beverage is shelf stable for at least 1 week at a temperature of about 40° C.

28. The fermented beverage of any one of embodiments 1-27, wherein the pH of the fermented beverage is less than about 3.5.

29. The fermented beverage of any one of embodiments 1-28, wherein the fermented beverage is kombucha, seltzer, soda, gut shot, water kefir, jun, fruit juice, vegetable juice, ginger beer, a flavored water product, or a probiotic beverage.

30. The fermented beverage of any one of embodiments 1-29, wherein at least one of the microbial strains is derived from a fermented food product.

31. The fermented beverage of any one of embodiments 1-30, wherein each of the microbial strains is derived from a fermented food product.

32. The fermented beverage of any one of embodiments 1-31, wherein the bacterial strains and the additional microbial strains are live in the fermented beverage.

33. The fermented beverage of any one of embodiments 1-32, further comprising one or more additional components.

34. The fermented beverage of embodiment 33, wherein the additional component is a vitamin, mineral, or flavoring additive.

35. The fermented beverage of embodiment 33 or 34, wherein the one or more additional component is selected from the group consisting of black tea, green tea, fruit juice, and vegetable juice.

36. A method of producing a fermented food beverage, comprising
(i) providing a medium comprising a fermentable sugar at an initial sugar level;
(ii) adding a symbiotic microbial community to the medium to produce a culture, wherein the symbiotic microbial community comprises at least one bacterial strain having a 16S rDNA sequence comprising at least 95% sequence identity to a nucleic acid sequence provided by SEQ ID NOs: 1-3, and at least one bacterial strain having a 16S rDNA sequence comprising at least 95% sequence identity to a nucleic acid sequence provided by SEQ ID NOs: 4-7, and at least one additional microbial strain; and
(iii) fermenting the culture under conditions to produce a fermented beverage.

37. The method of embodiment 36, wherein the symbiotic microbial community comprises at least two, at least three, or at least four additional microbial strains.

38. The method of embodiment 36 or 37, wherein at least one of the additional microbial strains is a bacterial strain.

39. The method of any one of embodiments 36-38, wherein each of the additional microbial strains is a bacterial strain.

40. The method of any one of embodiments 36-40, wherein the additional bacterial strain belongs to the genus *Lactobacillus, Gluconobacter, Leuconostoc, Acetobacter, Hafnia/Obesumbacterium, Lactococcus, Pediococcus,* or *Bacillus*.

41. The method of embodiment 40, wherein the additional bacterial strain belongs to the species *Acetobacter pasteurianus, A. ghanesis, A. orientalis, A. tropicalis, Gluconobacter oxydans, G. roseus, G. japonicus, G. frateurii, Lactobacillus senmaizukei, L. brevis, Leuconostoc mesenteroides, Lactobacillus parakefiri, L. hilgardii, L. diolivorans, L. rapi, L. kisonesis, L. buchneri, L. fuchuensis, L. plantarum, L. paraplantarum, L. fabifermentans, L. pentosus, L. graminis, L. composti, Bacillus zanthoxyli, B. qingshengii, B. aryabhattai, B. flexus, B. megaterium, Hafnia alvei, Obesumbacterium proteus, Lactococcus taiwanensis, L. lactis, Lactobacillus casei, L. paracasei, Pediococcus claussenii, P. stilesii, P. pentosaceus, P. acidilactici, Gluconacetobacter liquefaciens, L. cerevisiae, L. kefiri, L. sunkii, L. otakiensis, L. parabuchneri, Leuconostoc lactis, L. palmae, L. holzapfelii, L. citreum, Lactobacillus nagelii, L. satsumensis, Acetobacter papayae, A. suratthaniensis, A. peroxydans, Gluconacetobacter takamatsuzukensis,* or *G. asukensis*.

42. The method of any one of embodiments 36-41, wherein the additional bacterial strain has a 16S rDNA sequence comprising at least 95% sequence identity to a nucleic acid sequence provided by SEQ ID NOs: 8-19.

43. The method of any one of embodiments 36-42, wherein the symbiotic microbial community comprises bacterial strains having a 16S rDNA sequence comprising at least 95% sequence identity to a nucleic acid sequence provided by SEQ ID NOs: 2, 4, 5, 6, 7, and 20-24.

44. The method of any one of embodiments 36-43, wherein the symbiotic microbial community comprises bacterial strains having a 16S rDNA sequence comprising at least 95% sequence identity to a nucleic acid sequence provided by SEQ ID NOs: 2, 5, 6, and 7.

45. The method of any one of embodiments 36-43, wherein the symbiotic microbial community comprises bacterial strains having a 16S rDNA sequence comprising at least 95% sequence identity to a nucleic acid sequence provided by SEQ ID NOs: 2, 4, and 5.

46. The method of any one of embodiments 36-44, wherein the symbiotic microbial community consists of bacterial strains having a 16S rDNA sequence comprising at least 95% sequence identity to a nucleic acid sequence provided by SEQ ID NOs: 2, 5, 6, and 7.

47. The method of any one of embodiments 36-43 and 45, wherein the symbiotic microbial community consists of bacterial strains having a 16S rDNA sequence comprising at least 95% sequence identity to a nucleic acid sequence provided by SEQ ID NOs: 2, 4, and 5.

48. The method of any one of embodiments 36-44, wherein the symbiotic microbial community comprises bacterial strains having a 16S rDNA sequence comprising at least 95% sequence identity to a nucleic acid sequence provided by SEQ ID NOs: 21, 20, 22, and 24.

49. The method of any one of embodiments 36-43 and 45, wherein the symbiotic microbial community comprises bacterial strains having a 16S rDNA sequence comprising at least 95% sequence identity to a nucleic acid sequence provided by SEQ ID NOs: 21, 23, and 20.

50. The method of any one of embodiments 36-44 and 48, wherein the symbiotic microbial community consists of bacterial strains having a 16S rDNA sequence comprising at least 95% sequence identity to a nucleic acid sequence provided by SEQ ID NOs: 21, 20, 22, and 24.

51. The method of any one of embodiments 36-43, 45, and 49, wherein the symbiotic microbial community consists of bacterial strains having a 16S rDNA sequence comprising at least 95% sequence identity to a nucleic acid sequence provided by SEQ ID NOs: 21, 23, and 20.

52. The method of any one of embodiments 36-43, wherein the symbiotic microbial community comprises bacterial strains having a 16S rDNA sequence comprising at least 95% sequence identity to a nucleic acid sequence provided by SEQ ID NOs: 2, 4, 5, and 7.

53. The method of any one of embodiments 36-43 and 52, wherein the symbiotic microbial community consists of bacterial strains having a 16S rDNA sequence comprising at least 95% sequence identity to a nucleic acid sequence provided by SEQ ID NOs: 2, 4, 5, and 7.

54. The method of any one of embodiments 36-43 or 52, wherein the symbiotic microbial community comprises bacterial strains having a 16S rDNA sequence comprising at least 95% sequence identity to a nucleic acid sequence provided by SEQ ID NOs: 21, 23, 20, and 24.

55. The method of any one of embodiments 36-43, 52, and 54, wherein the symbiotic microbial community consists of bacterial strains having a 16S rDNA sequence comprising at least 95% sequence identity to a nucleic acid sequence provided by SEQ ID NOs: 21, 23, 20, and 24.

56. The method of any one of embodiments 36-55, wherein the symbiotic microbial community does not comprise a yeast strain.

57. The method of any one of embodiments 36-56, wherein the symbiotic microbial community comprises at least $2 \times 10^7$ colony forming units of each bacterial strain and each additional microbial strain per milliliter of the fermented beverage.
58. The method of any one of embodiments 36-57, comprising a level of acetic acid less than 1 gram per liter (g/L).
59. The method of any one of embodiments 36-58, comprising a level of organic acid that is greater than 1 gram per liter (g/L), wherein the organic acid is not acetic acid.
60. The method of embodiment 59, wherein the organic acid is lactic acid, gluconic acid, ketogluconic acid, or a combination thereof.
61. The method of any one of embodiments 36-60, wherein the fermented beverage is shelf stable for at least 2 weeks at a temperature of about 20° C.
62. The method of any one of embodiments 36-61, wherein the fermented beverage is shelf stable for at least 1 week at a temperature of about 40° C.
63. The method of any one of embodiments 36-62, wherein the pH of the fermented beverage is less than about 3.5.
64. The method of any one of embodiments 36-63, wherein the fermented beverage is kombucha, seltzer, soda, gut shot, water kefir, jun, fruit juice, vegetable juice, ginger beer, a flavored water product, or a probiotic beverage.
65. The method of any one of embodiments 36-64, wherein at least one of the microbial strains is derived from a fermented food product.
66. The method of any one of embodiments 36-65, wherein each of the microbial strains is derived from a fermented food product.
67. The method of any one of embodiments 36-66, wherein the bacterial strains and the additional microbial strains are live in the fermented beverage.
68. The method of any one of embodiments 36-67, further comprising one or more additional components.
69. The method of embodiment 68, wherein the additional component is a vitamin, mineral, or flavoring additives.
70. The method of embodiment 68 or 69, wherein the one or more additional component is selected from the group consisting of black tea, green tea, fruit juice, and vegetable juice.
71. The method of any one of embodiments 36-70, wherein the fermented beverage has a pH less than about 3.5.
72. The method of any one of embodiments 36-71, wherein the fermenting is performed in a batch reactor.
73. The method of any one of embodiments 36-72, wherein the fermenting is performed at about 18-37° C.
74. The method of any one of embodiments 36-73, wherein the fermenting is performed for at least 6 days at about 20° C.
75. The method of any one of embodiments 36-74, wherein the initial sugar level is 2.5-20 grams per liter (g/L) of a sugar source.
76. The method of any one of embodiments 36-75, wherein the initial sugar level is about 10 grams per liter (g/L) of a sugar source.
76. The method of embodiment 76, wherein the sugar source is a cane sugar, palm sugar, maple syrup, fruit juice, vegetable juice, brown sugar, molasses, agave nectar, honey, date syrup, date paste, date sugar, coconut sugar, or coconut water.
77. The method of any one of claims 36-76, wherein the bacterial strains and the additional microbial strain(s) replicate faster when in the symbiotic microbial community compared to when not in the symbiotic microbial community.
78. The method of any one of embodiments 36-77, wherein the bacterial strains and the additional microbial strain(s) grow to a higher biomass when in the symbiotic microbial community compared to when not in the symbiotic microbial community.
79. The method of any one of embodiments 36-78, wherein the symbiotic microbial community comprises at least $2 \times 10^5$ colony forming units.
80. The method of any one of embodiments 36-79, wherein the biomass of the symbiotic microbial community is stable over at least 60 days.
81. The method of any one of embodiments 36-80, wherein the symbiotic microbial community reduces or prevents growth of undesired microbial strains.
82. The method of any one of embodiments 36-81, further comprising carbonating the fermented beverage to produce a carbonated fermented beverage.
83. A fermented beverage obtained or obtainable by the method of any one of embodiments 36-82.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or"

should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A fermented beverage comprising
a symbiotic microbial community comprising a bacterial strain having a 16S rDNA sequence having at least 95% sequence identity to a nucleic acid sequence provided by SEQ ID NO: 2, a bacterial strain having a 16S rDNA sequence having at least 95% sequence identity to a nucleic acid sequence provided by SEQ ID NO: 4 or SEQ ID NO: 5, and an additional microbial strain,
a sugar content that is less than 20 grams per liter (g/L),
an ethanol level that is less than 0.5% alcohol by volume (abv, v/v), and
an acetic acid level that is less than 1 g/L.

2. The fermented beverage of claim 1, wherein the symbiotic microbial community comprises a bacterial strain having a 16S rDNA sequence having at least 95% sequence identity to a nucleic acid sequence provided by SEQ ID NO: 2, a bacterial strain having a 16S rDNA sequence having at least 95% sequence identity to a nucleic acid sequence provided by SEQ ID NO: 4, and an additional microbial strain.

3. The fermented beverage of claim 1, wherein the symbiotic microbial community comprises a bacterial strain having a 16S rDNA sequence having at least 95% sequence identity to a nucleic acid sequence provided by SEQ ID NO: 2, a bacterial strain having a 16S rDNA sequence having at least 95% sequence identity to a nucleic acid sequence provided by SEQ ID NO: 5, and an additional microbial strain.

4. The fermented beverage of claim 1, wherein the symbiotic microbial community comprises three bacterial strains having 16S rDNA sequences of at least 95% sequence identity to a nucleic acid sequence provided by SEQ ID NOs: 2, 4 and 5.

5. The fermented beverage of claim 1, wherein the symbiotic microbial community consists of a bacterial strain having a 16S rDNA sequence having at least 95% sequence identity to a nucleic acid sequence provided by SEQ ID NO: 2, a bacterial strain having a 16S rDNA sequence having at least 95% sequence identity to a nucleic acid sequence provided by SEQ ID NO: 4 or SEQ ID NO: 5, and an additional microbial strain.

6. The fermented beverage of claim 1, wherein the symbiotic microbial community consists of a bacterial strain having a 16S rDNA sequence having at least 95% sequence identity to a nucleic acid sequence provided by SEQ ID NO: 2, a bacterial strain having a 16S rDNA sequence having at least 95% sequence identity to a nucleic acid sequence provided by SEQ ID NO: 4, and an additional microbial strain.

7. The fermented beverage of claim 1, wherein the symbiotic microbial community consists of a bacterial strain having a 16S rDNA sequence having at least 95% sequence identity to a nucleic acid sequence provided by SEQ ID NO: 2, a bacterial strain having a 16S rDNA sequence having at least 95% sequence identity to a nucleic acid sequence provided by SEQ ID NO: 5, and an additional microbial strain.

8. The fermented beverage of claim 1, wherein the symbiotic microbial community comprises three bacterial strains having 16S rDNA sequences of at least 95% sequence identity to a nucleic acid sequence provided by SEQ ID NOs: 2, 4 and 5.

9. The fermented beverage of claim 1, wherein the symbiotic microbial community comprises a bacterial strain having a 16S rDNA sequence having at least 97% sequence identity to a nucleic acid sequence provided by SEQ ID NO: 2, a bacterial strain having a 16S rDNA sequence having at least 97% sequence identity to a nucleic acid sequence provided by SEQ ID NO: 4 or SEQ ID NO: 5, and an additional microbial strain.

10. The fermented beverage of claim 1, wherein the symbiotic microbial community comprises a bacterial strain having a 16S rDNA sequence having at least 97% sequence identity to a nucleic acid sequence provided by SEQ ID NO: 2, a bacterial strain having a 16S rDNA sequence having at least 97% sequence identity to a nucleic acid sequence provided by SEQ ID NO: 4, and an additional microbial strain.

11. The fermented beverage of claim 1, wherein the symbiotic microbial community comprises a bacterial strain having a 16S rDNA sequence having at least 97% sequence identity to a nucleic acid sequence provided by SEQ ID NO: 2, a bacterial strain having a 16S rDNA sequence having at least 97% sequence identity to a nucleic acid sequence provided by SEQ ID NO: 5, and an additional microbial strain.

12. The fermented beverage of claim 1, wherein the symbiotic microbial community comprises a bacterial strain having a 16S rDNA sequence having at least 99% sequence identity to a nucleic acid sequence provided by SEQ ID NO: 2, a bacterial strain having a 16S rDNA sequence having at least 99% sequence identity to a nucleic acid sequence provided by SEQ ID NO: 4 or SEQ ID NO: 5, and an additional microbial strain.

13. The fermented beverage of claim 1, wherein the symbiotic microbial community comprises a bacterial strain having a 16S rDNA sequence having at least 99% sequence identity to a nucleic acid sequence provided by SEQ ID NO: 2, a bacterial strain having a 16S rDNA sequence having at least 99% sequence identity to a nucleic acid sequence provided by SEQ ID NO: 4, and an additional microbial strain.

14. The fermented beverage of claim 1, wherein the symbiotic microbial community comprises a bacterial strain having a 16S rDNA sequence having at least 99% sequence identity to a nucleic acid sequence provided by SEQ ID NO: 2, a bacterial strain having a 16S rDNA sequence having at least 99% sequence identity to a nucleic acid sequence provided by SEQ ID NO: 5, and an additional microbial strain.

15. The fermented beverage of claim 1, wherein the fermented beverage does not comprise a yeast strain.

16. The fermented beverage of claim 1, wherein in the pH of the fermented beverage is less than about 4.5.

17. The fermented beverage of claim 1, wherein the fermented beverage is a seltzer, soda, flavored water product, or a probiotic beverage.

18. The fermented beverage of claim 1, wherein at least one of the bacterial strains is derived from a fermented food product.

19. The fermented beverage of claim 1, wherein each of the bacterial strains is derived from a fermented food product.

20. The fermented beverage of claim 1, wherein each of the bacterial strains is live in the fermented beverage.

21. The fermented beverage of claim 1, comprising between $3 \times 10^6$ and $3 \times 10^8$ colony forming units (CFUs) per bacterial strain per milliliter of fermented beverage.

22. The fermented beverage of claim 1, comprising between $1.5 \times 10^7$ and $1.5 \times 10^9$ total CFU per milliliter of fermented beverage.

23. The fermented beverage of claim 1, further comprising one or more additional components selected from the group consisting of a nutritive component, a flavoring component, a sweetening component and combinations thereof.

24. The fermented beverage of claim 23, wherein the nutritive component is a vitamin or a mineral; and/or
wherein the flavoring component is a natural fruit flavoring, a naturally derived fruit flavoring, or a synthetic fruit flavoring.

25. The fermented beverage of claim 1, wherein the fermented beverage is shelf-stable, for at least two weeks, at a temperature of about 20° C. to about 22° C., wherein shelf-stability is assessed by viability of bacterial strains and/or flavor profile.

26. The fermented beverage of claim 1, wherein the fermented beverage comprises a biomass that decreases by less than 10% over a period of 60 days at a temperature of about 20° C.-22° C.

27. The fermented beverage of claim 1, wherein the fermented beverage further comprises lactic acid, gluconic acid, ketogluconic acid, or a combination thereof.

28. The fermented beverage of claim 1, wherein the symbiotic microbial community reduces or prevents growth of one or more undesired microbial strains.

29. The fermented beverage of claim 1, wherein the fermented beverage is produced by a method comprising
(i) providing a medium comprising a fermentable sugar at an initial sugar level;
(ii) adding the symbiotic microbial community to the medium to produce a culture; and
(iii) fermenting the culture under conditions to produce a fermented beverage.

30. A method of producing the fermented beverage of claim 1, comprising
(i) providing a medium comprising a fermentable sugar at an initial sugar level;
(ii) adding a symbiotic microbial community to the medium to produce a culture, wherein the symbiotic microbial community comprises a bacterial strain having a 16S rDNA sequence having at least 95% sequence identity to a nucleic acid sequence provided by SEQ ID NO: 2, a bacterial strain having a 16S rDNA sequence having at least 95% sequence identity to a nucleic acid sequence provided by SEQ ID NO: 4 or SEQ ID NO: 5, and an additional microbial strain; and
(iii) fermenting the culture under conditions to produce a fermented beverage.

* * * * *